US006884770B1

(12) United States Patent
Galdes et al.

(10) Patent No.: US 6,884,770 B1
(45) Date of Patent: Apr. 26, 2005

(54) METHODS AND COMPOSITIONS FOR TREATING OR PREVENTING PERIPHERAL NEUROPATHIES

(75) Inventors: Alphonse Galdes, Lexington, MA (US); Nagesh Mahanthappa, Cambridge, MA (US)

(73) Assignee: Curis, Inc., Cambridge, MA (US)

( * ) Notice: Subject to any disclaimer, the term of this patent is extended or adjusted under 35 U.S.C. 154(b) by 0 days.

(21) Appl. No.: 09/569,386

(22) Filed: May 11, 2000

Related U.S. Application Data

(63) Continuation-in-part of application No. 09/435,733, filed on Nov. 8, 1999, which is a continuation-in-part of application No. 09/187,387, filed on Nov. 6, 1998.

(51) Int. Cl.[7] .......................... C07K 1/00; C07H 21/04; C12N 1/20; C12P 21/06; G01N 33/567
(52) U.S. Cl. .......................... 514/2; 530/300; 530/350; 536/23.5; 435/7.1; 435/7.21; 435/69.5; 436/501
(58) Field of Search .............................. 514/2; 530/300, 530/350; 536/23.5; 435/7.1, 7.21, 69.5; 436/501

(56) References Cited

U.S. PATENT DOCUMENTS

| | | | |
|---|---|---|---|
| 4,456,687 A | 6/1984 | Green | 435/241 |
| 5,223,408 A | 6/1993 | Goeddel et al. | 435/69.3 |
| 5,585,087 A | 12/1996 | Lustig et al. | 424/9.2 |
| 5,643,915 A | 7/1997 | Andrulis, Jr. et al. | 514/279 |
| 5,747,507 A | 5/1998 | Ikegaki et al. | 514/312 |
| 5,759,811 A | 6/1998 | Epstein et al. | 435/69.1 |
| 5,789,543 A | 8/1998 | Ingham et al. | 530/350 |
| 5,837,538 A | 11/1998 | Scott et al. | 435/325 |
| 5,844,079 A | 12/1998 | Ingham et al. | 530/350 |

FOREIGN PATENT DOCUMENTS

| | | |
|---|---|---|
| EP | 0187 371 A2 | 7/1986 |
| EP | 0249 873 A2 | 6/1987 |
| EP | 0874048 A2 | 10/1998 |
| EP | 0879888 A2 | 11/1998 |
| JP | 63 08 81 12 | 4/1988 |
| JP | 02 27 36 10 | 11/1990 |
| JP | 04 30 55 28 | 10/1992 |
| WO | WO 90/02809 | 3/1990 |
| WO | WO 92/15679 | 9/1992 |
| WO | WO 94/28016 | 12/1994 |
| WO | WO 95/18856 | * 7/1995 |
| WO | WO 95/23223 | 8/1995 |
| WO | WO 96/ 09806 | 4/1996 |
| WO | WO 96/11260 | 4/1996 |
| WO | WO 96/16668 | 6/1996 |
| WO | WO 96/17924 | 6/1996 |
| WO | WO 96/29342 | * 9/1996 |
| WO | WO 97/11095 | 3/1997 |
| WO | WO 97/45541 | 12/1997 |
| WO | WO 98/12326 | 3/1998 |
| WO | WO 98/14475 | 4/1998 |
| WO | WO 98/21227 | 5/1998 |
| WO | WO 98/30234 | 7/1998 |
| WO | WO 98/30576 | 7/1998 |
| WO | WO 98/35020 | 8/1998 |
| WO | WO 99/00117 | 1/1999 |
| WO | WO 99/00403 | 1/1999 |
| WO | WO 99/01468 | 1/1999 |
| WO | WO 99/04775 | 2/1999 |
| WO | WO 99/10004 | 3/1999 |
| WO | WO 99/ 29854 | 6/1999 |

OTHER PUBLICATIONS

Bowie et al., 1990, Science 247:1306–1310.*
Miao et al., J. Neuroscience 17(15)5891–5899, 1997.*
Lahana R., Drug Discovery Today, 4(10)447–448, 1999.*
Horrobin, DF, British Med. Journal, 322(7280)239, Jul. 2003.*
Porter JA et al., Science 274(255–259)1996.*
Pepinsky RB et al., J. Biol. Chem. 273(22)14037–14045, 1996.*
Stull and Iacovitti, Experimental Neurobiology 169(1)36–43, 2001.*
Welty et al., Soc. Neurosci. Abs. 27(2)pp2621, 2001.*
Engber et al., Soc. Neurosci. Abs. 26(1–2)Abs No. 792.14, 2000.*
Oppenhiem et al. Mol. Cell Neuroscience 13(348–361)1999.*
International Search report, PCT/US99/26334, filed Aug. 11, 1999.
Miao, N. et al. Sonic Hedgehog Promotes the Survival of Specific CNS Neuron Polulations and Protects These Cells from Toxic Insult In Vitro. J. Neurosci. 17, 5891–5899 (Aug. 1, 1997).
Wang, Q–c. et al. Polyethylene Glycol–modified Chimeric Toxin Composed of Transforming Growth Factor alpha and Pseudomonas Exotoxin. Cancer Res. 53, 4588–4594 (Oct. 1, 1993).

(Continued)

Primary Examiner—Janet Andres
Assistant Examiner—Michael Brannock
(74) Attorney, Agent, or Firm—Ropes & Gray LLP

(57) ABSTRACT

The present application is directed to the discovery that hedgehog gene products are able to protect peripheral nerve cells under conditions which otherwise result in peripheral neuropathy. Certain aspects of the invention are directed to preparations of hedgehog polypeptides, or other molecules which regulate patched or smoothened signalling, and their uses as protective agents against both acquired and hereditary neuropathies. As used herein, "peripheral neuropathy" refers to a disorder affecting a segment of the peripheral nervous system. For instance, the method of the present invention can be used as part of a treatment program in the management of neuropathies associated with systemic disease, e.g., viral infections, diabetes, inflamation; as well as genetically acquired (hereditary) neuropathies, e.g., Charcot-Marie-Tooth disease; and neuropathies caused by a toxic agent, e.g., a chemotherapeutic agent such as vincristine.

15 Claims, 24 Drawing Sheets

OTHER PUBLICATIONS

Anderson, R. et al., "Maintenance of ZPA signaling in cultred mouse limb bud cells", *Devel.* 117:1421–1433 (1993).

Angier, N., "Biologists find key genes that shape patterning of embryos", *New York Times,* Jan. 11, 1994, C–1.

Apfel, S. et al.;"Nerve Growth Factor Prevents Toxic Neuropathy in Mice", *Ann. Neurol.* , 29 : 87–90 (1991).

Apfel, S. et al.; "Nerve Growth Factor Prevents Experimental Cisplatin Neuropathy", *Ann. Neurol.* 31 : 76–80 (1992).

Basler, K. and G. Struhl, "Compartment boundaries and the control of *Drosophila* limb pattern by Hedgehog protein" *Nature* 368:208–214 (1994).

Basler, K. et al., "Control of cell pattern in the neural tube: Regulation of cell differntiation by dorsalin–1, a novel TGFβ family member", *Cell* 73:687–702 (1993).

Bass, S. et al., "Hormone phage: An enrichment method for variant proteins with altered binding properties", *Proteins: Structure, Function, and Genetics* 8:309–314 (1990).

Bejsovec, A. and E. Wieschaus, "Segment polarity gene interactions modulate epidermal patterning in *Drosophila* embryos", *Development* 119:501–517 (1993).

Beinz, M., "Homeotic genes and positional signalling in the *Drosophila viscera*", *TIG* 10:22–26 (Jan. 1994).

Bitgood, M. and A. McMahon, "Hedgehog and Bmp genes are coexpressed at many diverse sites of cell–cell cnteraction in the mouse embryo", *Dev. Biol.* 172(1):126–138 (1995).

Blair, S. S., "Hedghog digs up an old friend", *Nature,* 373:656–657 (Feb. 23, 1995).

Brand–Saberi, B. et al., "The ventralizing effect of the notochord on somite differentiation in chick embryos",*Anat. Embryol.* 188:239–245 (1993).

Brockes, J., "We may not have a morphogen" *Nature 350*:15 (1991).

Bumcrot, D. A. et al., "Proteolytic processing yeilds two secreted forms of sonic hedgehog", *Mol. Cell. Biol.* 15(4):2294–2303 (Apr. 1995).

Bumcrot, D. A. and A. McMahon, "Sonic hedgehog: Making the gradient", *Chem. Biol.* 3(1):13–16 (Jan. 1996).

Bumcrot, D. A. and A. McMahon, "Somite differentiation. Sonic signals somites", *Curr. Biol.* 5(6):612–614 (Jun. 1995).

Charité, J. et al., "Ectopic expression of Hoxb–8 causes duplication of the ZPA in the forelimb and homeotic transformation of axial strcutures", *Cell* 78:589–601 (1994).

Coffman, et al., "Xotch, the Xe is homolog of *Drosophila* notch", *Science* 249:1400 (1990).

Concordet, J. and P. Ingham, "Developmetal biology Patterning goes sonic", *Nature* 375(6529):279–280 (May 1995).

Curry et al., "Sequence analysis reveals homology between two proteins of the flagellar radial spoke", *Mol. Cell. Biol.* 12:3967–3970 (1992).

Davidson, E. H., "How embryos work: a comparative view verse modes of cell fate specification", *Develop.* 108:365–389 (1990).

Davis, A. P. and M. R. Capecchi, "Axial homeosis and appendicular skeleton defects in mice with a targeted disruption of hoxd–1", *Devel.* 120:2187–2198 (1994).

Dickinson W., "Molecules and morphology: Where's the homology", *TIG* 11(4):119–120 (1995).

Dingemanse, M. A. et al., "The expression of liver–specific genes within rat embryonic hepatocytes is a discontinous process", *Differentiation* 56:153–162 (1994).

Dollé, P. et al., "Coordinate expression of the murine Hox–5 complex homeobox–containing genes during limb pattern formation", *Nature* 342:767–772 (1989).

Dollé, P. et al., "Disruption of the Hoxd–13 gene induces localized heterochrony leading to mice with neotenic limbs", *Cell* 75:431–441 (1993).

Echelard, Y. et al., "Sonic hedgehog, a member of a family of putative signaling molecules, is implicated in the regulation of CNS polarity", *Cell* 751417–1430 (1993).

Ekker, S. et al., "Distinct expresion and shared activities of members of the hedgehog gene family of *xenopus laevis"*, *Devel.* 121(8):2337–2347 (Aug. 1995).

Ericson, J. et al., "Sonic hedgehog induces the differentiation of ventral forebrain neurons: a common signal for ventral patterning within the neural tube", *Cell* 81(5):747–756 (Jun. 1995).

Ettelaie, C. et al., "The effect of lipid peroxidation and lipolysis on the ability of lipoproteins to influence thromboplastin activity", *Biochim. Biophys. Acta.* 1257(1):25–30 (Jun. 1995).

Fahmer, K. et al., "Transcription of H–2 and Qa genes in embryonic and adult mice", *EMBO J.* 6:1265–1271 (1987).

Fallon, J. F. et al., "FGF–2: Apical ectodermal ridge growth signal for chick limb development", *Science* 264:104–107 (1994).

Fan, C. et al., "Long–range sclerotome induction by sonic hedgehog: Direct role of the amino–terminal cleavage product and modulation by the cyclic AMP signaling pathway", *Cell* 81:457–465 (May 5, 1995).

Fietz, M. et al., "The hedgehog gene family in *Drosophila* and vertebrate development", *Devel. (Suppl.)*:43–51 (1994).

Forbes, A. J. et al., "Genetic analysis of hedgehog signaling in the *Drosophila* embryo", *Devel.* 119 *(Suppl.)*:115–124 (1993).

Francis, P.H. et al., "Bone morphogenetic proteins and a signaling pathway that controls patterning in the developing chick limb", *Devel.* 120:209–218 (1994).

Gallop, M. et al., "Applications of combinatorial technologies to drug discovery. 1. Background and peptide combinatorial libraries", *J. Med. Chem.* 37(9):1233–1251 (1994).

Gao, W. et al.; "Neurotrophin–3 Reserves Experimental Cisplatin–induced Peripheral Sensory Neuropathy", *Ann. Neurol.* 38(1) : 30–37 (Jul. 1995).

Gérard, M. et al., "Structure and activity of regulatory elements involved in the activation of the Hoxd–11 gene during late gastrulation", *EMBO J.* 12:3539–3550 (1993).

Gurdon, J. B., "The generation of diversity and pattern in animal development", *Cell* 68:185–199 (1992).

Gustin, et al., "Characterization of the Role of Individual Protein Binding Motifs Within the Hepatitis B Virus Enhancer 1 on X Promoter Activity Using Linker Scanning Mutagenesis", *Virology* 193 : 653–660 (1993).

Hall, T. et al., "A potential catalytic site revealed by the 1.7—A crystal structure of the amino– terminal signaling domain of sonic hedgehog", *Nature* 378 (6553):212–216 (Nov. 1995).

Halpern, M. E. "Induction of Mu Pioneers and Floor Plate Is Distinguished by the Z no tail Mutation", *Cell* 75: 99–111 (1993).

Hamburger, V. and H. L. Hamilton, "A series of normal stages in the development of the chick embryo", *J. Morph.* 88:49–92 (1951).

Hamers, F. et al.; "Cisplatin–induced Neuropathy in Mature Rats: Effects of the Melanocortin–derived Peptide ORG 2766", Cancer Chemother. Pharmacol. 32 : 162–166 (1993).

Hammerschmidt, M. et al., "The world according to hedgehog", *TIG* 13(1);14–21 (1997).

Haramis, A. et al., "The limb deformity mutation disrupts the SHH/ FGF–4 feedback loop and regulation of 5' D genes during limb pattern formation", *Devel.* 121(12):4161–4170 (Dec. 1995).

Hardy, A. et al., "Gene expression, polarising activity and skeletal patterning in reaggregated hind limb mesenchyme", *Devel.* 121(12):4329–4337 (Dec. 1995).

Harmon, C. S. et al., "Evidence that activation of protein kinase A inhibits human hair fillicle growth and hair fibre production in organ culture and DNA synthesis in human and mouse hair follicle organ culture", *British J. Dermatol.* 136:853–858 (1997).

Hatta, K. et al., "The cyclops mutation blocks specification of the floor plate of the zebrafish central nervous system", *Nature* 350:339–341 (1991).

Heberlein, U. et al., "The TGBβ homolog dpp and the segment polarity gene hedgehog are required for propagation of a morphogenetic wave in the *Drosophila* retina", *Cell* 75:913–926 (1993).

Heemskerk, J. and S. DiNardo, "*Drosophila* hedgehog acts as a morphogen in cellular patterning", *Cell* 76:449–460 (1994).

Hidalgo, A. and P. Ingham, "Cell patterning in the *Drosophila* segment: spatial regulation of the segment polarity gene patched", *Devel.* 110:291–301 (1990).

Hooper, J. and M. Scott, "The *Drosophila* patched gene encodes a putative membrane protein required for segmental patterning", *Cell* 59:751–765 (1989).

Hynes, R. O., "Integrins: A family of cell surface receptors", *Cell* 48:549–554 (1987).

Ingham, P. W., "Signaling by hedgehog family proteins in *Drosophila* and verterbrate development", *Curr. Opin. Genet. Dev.* 5(4):478–484 (Aug. 1995).

Ingham, P. W., "Hedgehog points the way", *Current Biology* 4(4):347–350 (1994).

Ingham, P. W., "Localized Hedgehog activity controls spatial limits of wingless transcription in the *Drosophila* embryo", *Nature* 366:560–562 (1993).

Ingham, P. W. and A. Hidalgo, "Regulation of wingless transcription in the *Drosophila* embryo", *Devel.* 117:283–291 (1993).

Ingham, P. W. et al., "Role of the *Drosophila* patched gene in postional signaling", *Nature* 353:184–187 (1991).

Izpisúa– Belmonte, J. –C. et al., "Expression of the homeobox Hox–4 genes and the specification of position in chick wing development", *Nature* 350:585–589 (1991).

Izpisúa– Belmonte, J. –C. et al., "Expression of Hox–4 genes in the chick wings links pattern formation to the epithelial– mesenchymal interaction that mediate growth", *EMBO J.* 11:1451–1457 (1992).

Jiang, J. and G. Struhl, "Protein kinase A and hedgehog signaling in *Drosophila* limb development", *Cell* 80(4):563–572 (Feb. 1995).

Jessel, T. M. and D. A. Melton, "Diffusible factors in vertebrate embryonic induction", *Cell* 68:257–270 (1992).

Johnson, R. L. and C. Tabin, "The long and short of hedgehog signaling", *Cell* 81:313–315 (May 5, 1995).

Johnson, R. L. et al., "Patched overexpression alters wing disc size and pattern: transcriptional and post–transcriptional effects on hedgehog targets", *Devel.* 121(12):4237–4245 (Dec. 1995).

Johnson, R. L. et al., "Ectopic expression of sonic hedgehog alters dorsal–ventral patterning of somites", *Cell* 79(7):1165–1173 (Dec. 1994).

Johnson, R. L. et al., "Mechanism of limb patterning", *Curr. Opin. Genet. Dev.* 4(4):50–54 (Aug. 1994).

Johnson, R. L. et al., "Sonic hedgehog: a key mediator of anterior–posterior patterning of the limb and dorso–ventral patterning of axial embryonic structures" *Biochem. Soc. Trans.* 22(3):569–574 (Aug. 1994).

Jones, M. et al., "Involvement of bone morphogenetic protein–4 (BMP–4) and Vgr–1 in morphogenesis and neurogenesis in the mouse", Devel. 111:531–542 (1991).

Kalderon, D., "Morphogenetic signalling. Responses to hedgehog" *Curr. Biol.* 5(6):580–582 (Jun. 1995).

Koonin, E., "A protein splice–junction motif in hedgehog family proteins", *Trends Biochem. Sci.* 20(4):141–147 (Apr. 1995).

Kornblihtt, A. R. et al., "Primary structure of human fibronectin: diferential splicing may generate at least 10 polypeptides from a single gene", *EMBO J.* 41755–1759 (1985).

Kornfeld, R. and S. Kornfeld, "Assembly of asparagine–linked oligosaccharides", *Ann. Rev. Biochem.* 54:631–664 (1985).

Krauss, S. et al., "Expression of the zebrafish paired box gene pax[zf–b] during early neurogenesis", *Devel.* 113:1193–1206 (1991).

Krauss, S. et al., "A functionally conserved homolog of the *Drosophila* Segment polarity gene hh is expressed in tissues with polarizing activity in zebrafish embryos", *Cell* 75:1431–1444 (1993).

Lai, C. et al., "Patterning of the neural ectoderm of *Xenopus laevis* by the amino–terminal product of hedgehog autoproteolytic cleavage", *Devel.* 121:2349–2360 (1995).

Laufer, E. et al., "Sonic hedgehog and Fgf–4 act through a signaling cascade and feedback loop to integrate growth and patterning of the developing limb bud", *Cell* 79:993–1003 (Dec. 16, 1994).

Lee, J. J. et al., "Secretion and localized transcription suggest a role in positional signaling for products of the segmentation gene hedgehog", *Cell* 71:33–50 (1992).

Lee, J. J. et al., "Autoproteolysis in hedgehog protein biogenesis", *Science* 266(5190):1528–1537 (Dec. 1994).

Lee, S. J. "Expression of growth/ differentiation factor1 in the nervous system: Conservation of a bicistronic structure", *Proc. Natl. Acad. Sci. USA* 88:4250–4254 (Year).

Levin, M. et al., "A molecular pathway determining left–right asymmetry in chick embryogenesis", *Cell* 82(5):803–814 (Sep. 8, 1995).

Li, W. et al., "Function of protein kinase in hedgehog signal transduction and *drosophila* imaginal disc development", *Cell* 80(4):553–562(Feb. 1995).

Lipton, R. et al.; "Taxol Produces a Predominantly Sensory Neuropathy", Neurology 39 : 368–373; (Mar., 1989).

Lopez–Martinez, A. et al., "Limb–patterning activity and restricted posterior localization of the amino–terminal product of sonic hedgehog cleavage", *Curr. Biol.* 5(7):791–796 (Jul. 1995).

Lumsden, A. and A. Graham, "Neural patterning: A forward role for hedgehog", *Curr. Biol.* 5(12):1347–1350 (Dec. 1995).

Ma, C. et al.,"Molecular cloning and characterization of rKlk10, a cDNA encoding T–kininogenase from rat submandibular gland and kidney", *Biochem.* 31(44):10922–10928 (1992).

Ma, C. et al., "The segment polarity gene hedgehog is required for the progression of the morphogenetic furrow in the developing *Drosophila* eye", *Cell* 75:927–938 (1993).

Ma, C. and K. Moses, "Wingless and patched are negative regulators of the morphogenetic furrow and can affect tissue polarity in the developing *Drosophila* compound eye", *Devel.* 121(8):2279–2289 (Aug. 1995).

Marigo, V. et al., "Biochemical evidence that patched is the hedgehog receptor", *Nature* 384:176–179 (1996).

Maccabe, J. A. and B. W. Parker, "The target tissue of limb–bud polarizing activity in the induction of supernumerary structures", *J. Embryol. Exp. Morph.* 53:67–73 (1979).

Maiese, K. et al., "Protein kinases modulate the sensitivity of hippocampal neurons to nitric oxide toxicity and anoxia", *J. Neurosci. Res.* 3677–87 (1993).

Marti, E. et al., "Distribution of hedgehog peptides in the developing chick and the embryo", *Devel.* 121(8):2537–2547 (Aug. 1995).

Marti, E. et al., "Requirement of 19K form of Sonic hedgehog for induction of distinct ventral cell types in CNS explants", *Nature* 375(6529):322–325 (May 1995).

Matise, M. et al.; "Gli2 is Required for Induction of Floor Plate and Adjacent Cells, But Not Most Ventral Neurons in the Mouse Central Nervous System", Development 125 : 2759–2770 (1998).

Mavillio, F. et al, "Activation of four homeobox gene clusters in human embryonal carcimona cells induced to differentiate by retinoic acid", *Differentiation* 37:73–79 (1988).

McGinnis, W. and R. Krumlauf, "Homeobox genes and axial patterning", *Cell* 68:283–302 (1992).

Mohler, J., "Requirements for hedgehog, a segmental polarity gene, in patterning larval and adult cuti of *drosophila*", *Genetics* 120:1061–1072 (1988).

Mohler, J. and K. Vani, "Molecular organization and embryonic expression of the hedgehog gene involved in cell–cell communication in segmental patterning of *Drosophila*", *Devel.* 115957–971 (1992).

Morgan, B. A. et al., "Targeted misexpression of Hox–4.6 in the avian limb bud causes apparent homeotic transformations", *Nature* 358:236–239 (1992).

Moliman, J. , " Cisplatin Neurotoxicity", The New England Journal of Medicine, 322 (2): 126–127 (Jan. 11, 1990).

Nakano, Y. et al., "A protein with several possible membrane–spanning domains encoded by the *Drosophila* segment polarity gene patched", *Nature* 341:508–513 (1989).

Ngo, J. et al., "Computational Complexity Protein", Merz and LeGrand, ed. @ Birkhause Boston (1994).

Niswander, L. and G. R. Martin, "FGF–4 and BMP–2 have opposite effects on limb growth", *Nature* 361:68–71(1993).

Niswander, L. et al., "A positive feedback loop coordinates growth and patterning in the vertebrate limb", *Nature,* 371:609–612 (Oct. 13, 1994).

Nohno, T. et al., "Involement of the Chox–4 Chicken Homeobox Genes in Determination of Anteroposterior Axial Polarity during Limb Development", *Cell,* vol. 64: 1197–1205 (Mar. 22, 1991).

Nohno, T. et al., "Involvement of the Sonic hedgehog gene in chick feather formation", *Biochem. Biophys. Res. Comm.* 206(1): 33–39 (Jan. 1995).

O'Farrell, P. H., "Unanimity waits in the wings", *Nature* 368:188–189 (1994).

Parisi, M. J. et al., "The role of the hedgehog/patched signaling pathway in epithelial stem cell proliferation: From fly to human", *Cell Res.* 8:15–21 (1998).

Parr, B. A. et al., "Mouse Wnt genes exhibit discrete domains of expression in the early embryonic CNS and limb buds", *Development* 119:247–261 (1993).

Patel, N. H. et al., "The role of segment polarity genes during *Drosophila* neurogenesis", *Genes & Devel.* 3:890–904 (1989).

Peifer, M., "The two faces of hedgehog", *Science* 266(5190):1492–1493 (Dec. 1994).

Perrimon, N. et al., "Generating lineage–specific markers to study *Drosophila* development", *Develop. Genet.,* 12:238–252 (1991).

Perrimon, N., "Hedgehog and beyond", *Cell* 80517–520 (Feb. 24, 1995).

Pharm, A. et al., "The Suppressor of fused gene encodes a novel PEST protein involved in *Drosophila* segment polarity establishment"*Genetics* 140(2):587–598 (Jun. 1995).

Phillis, J. W. and M. H. O'Regan, "Mechanism of glutamate and aspartate release in the ischemic rat cerebral cortex", *Brain Res.* 730:150–164 (1996).

Placzek, M. et al., "Induction of floor plate differentiation by contact–dependent, homeogenetic signals", *Development* 117: 205 218 (1993).

Placzek, M. et al., " Orientation Commissural Axons in vitro in response to a floor chemoattractant", *Develop.* 110:19–30 (1990).

Pollock, R. A. et al., "Altering the boundaries of Hox3.1 expression: Evidence for antipodal gene regulation", *Cell* 71:911–923 (1992).

Porter, J. et al., "The product of hedgehog autoproteolytic cleavage active in local and long–range signalling", *Nature* 374(6520):363–366 (Mar. 23, 1995).

Reeck, et al., "'Homology' in proteins and nucleic acids: A terminology muddle and a way out of it", *Cell* 50:667 (Aug. 28, 1987).

Rennie, J., "Super Sonic", *Sci. Amer.*p.20, (Apr. 1994).

Riddle, R. D. et al. "Induction of the LIM homeobox gene L by WNT7a establishes dorsoventral pattern in the verterbrate limb", *Cell* 83:631–640 (Nov. 17, 1995).

Riddle, R. et al.; " Sonic Hedgehog Mediates the Polarizing Activity of the ZPA", Cell, 75 :1401–1416 (Dec. 31, 1993).

Riley, B. B. et al., "Retroviral expression of FGF–2 (bFGF) affects patterning in chick limb bud", *Develop.* 118:95–104 (1993).

Roberts, D. et al., "Sonic hedgehog is an endodermal signal inducing Bmp–4 and Hox genes during induction and regionalization of the chick hindgut", *Develop.* 121(10):3163–3174 (Oct. 1995).

Roelink, H. et al., "Floor plate and motor neuron induction vhh–1, a vertebrate homolog of hedgehog expressed by the notochord", *Cell* 76:761–775 (Feb. 25, 1994).

Roelink, H. et al.; "Floor Plate and Motor Neuron Induction By Different Concentrations of the Amino–Terminal Cleavage Product of Sonic Hedgehog Autoproteolysis ", Cell, 81 : 445–455 (May 5, 1995).
Sachiko, I. et al., "Sonic hedgehog is expressed in epithelial cells during development of whisker, hair and tooth", Biochem. Biophys. Res. Commun. 218688–693 (1996).
Satoh, S. et al., "Neuroprotective properties of a protein kinase inhibitor against ischaemia–induced neuronal damage in rats and gerbils", Br. J. Pharmacol. 118:1592–1596 (1996).
St. Jacques, B. et al., "Sonic hedgehog signaling is essential for hair development", Curr. Biol. 8:1058–1068 (1998).
Sasaki, H. and B. L. M. Hogan, "Differential expression of multiple fork head related genes during gastrulation and axial pattern formation in the mouse embryo", Develop. 118:47–59 (1993).
Savage, M. et al., "Distribution of FGF– 2 suggests it has role in chick limb bud growth", Devel. Dynamics 198:159–170 (1993).
Schuske, K. et al., "Patched overexpression causes loss of wingless expression in drosophila embryos", Devel. Biol. 164 : 300– 311 (1994).
Smith, J. C., "Hedgehog, the floor plate, and the zone of polarizing activity", Cell 76:193–196 (1994).
Stachel, S. E. et al., "Lithium perturbation and goosecoid expression identify a dorsal specification pathway in the pregastrula zebrafish", Develop. 117:1261–1274 (1993).
Stolow, M. and Shi, Y., "Xenopus sonic hedgehog as a potential morphogen during embryogenesis and thyroid hormone–dependent metamorphosis", Nucl. Acids Res. 23(13):2555–2562 (1995).
Tabata, T. and T. B. Kornberg, "Hedgehog is a signaling protein with a key role in patterning drosophila imaginal discs", Cell 76: 89–102 (1994).
Tabata, T. et al., "The Drosophila hedgehog gene is expressed specifically in posterior compartment cells and is a target of engrailed regulation", Genes & Develop. 6:2635–2645 (1992).
Tabin, C. J., "Retinoids homeoboxes, and growth factors: Toward molecular models for limb development", Cell 66:199–217 (Jul. 26, 1991).
Tanabe, Y. et al., "Induction of motor neurons by sonic hedgehog is independent of floor plate differentiation", Curr. Biol. 5(6):651–658 (Jun. 1995).
Tanaka, E. and A. Gann, "Limb development: The budding role of FGF", Curr. Biol. 5(6):594–597 (Jun. 1995).
Tashiro, S. et al., "Structure and expression of hedgehog, a Drosophila segment–pola required for cell–cell communication", Gene 124:183–189 (1993).
Taylor, A. M. et al., "Contrasting distributions of patched and hedgehog proteins in the Drosophila embryo", Mech. Develop. 42: 89–96 (1993).

Thaller, C. and G. Eichele, " Identification and spatial distribution of retinoids in the developing chick limb bud", Nature 327 : 625–628(1987).
Thummel, et al., "Vectors for Drosophila P–element–mediated transformation and tissue culture transfection", Gene 74445–456 (1988).
Tickle, C. et al., "A quantitative analysis of the effect of all–trans–retinoic acid on the pattern of chick wing development", Develop. Biol. 109:82–95 (1985).
Tickle, C. et al., "Vertebrate limb development", Curr. Opin. Genet. Dev. 5(4):478–484 (1995).
Tickle, C. and G. Eichie, "Vertebrate limb development", Ann. Rev. Cell Biol. 10:121–152(1994).
Tilson, H. et al.; "Neurobehavioral Techniques to Assess the Effects of Chemical on Nervous System ", Ann. Rev. Pharmacol. Toxicol. 24 : 425–450 (1984).
Traiffort, E. et al., "Regional Distribution of Sonic Hedgehog, Patched, and Smoothened mRNA in the Adult Rat Brain", Journal of Neurochemistry 70(3): 1327–1330 (1998).
Van Straaten, H. W. M. et al., "Effect of the notochord on the differentiation of a floor plate area in the neural tube of the chick embryo", Anat. Embryol. 177:317–324 (1988).
Vogel, A. and C. Tickle, "FGF–4 maintains polarizing activity of posterior limb but cells in vivo and in vitro", Develop. 119:199– 206 (1993).
Wallace, et al., "Oligonucleotide probes for the screening of recombinant DNA libraries", Methods in Enzymol. 152:432–443 (1987).
Wanek, N. et al., "Conversion by retinoic acid of anterior cells into ZPA cells in the chick wing bud", Nature 350:81–83 (Mar. 7, 1991).
Yamada, T. et al., "Control of cell pattern in the developing nervous system: Polarizing activity of the floor plate and notochord", Cell, 64:635–647, (Feb. 8, 1991).
Yang, Y. and L. Niswander, "Interaction between the signaling molecules WNTZ7a and SHH during vertebrate limb development: dorsal signals regulate anteroposterior patterning", Cell 80:939–947 (Mar. 24, 1995).
Yun–Bo Shi, "Cell–cell and cell ECM interactions in epithelial apoptosis and cell renewal during frog intestinal development", Cell Biochem. Biophys.27:179–202 (1995).
Zappavigna, et al., "Hog4 genes encode transcription factors with potential auto– and cross–regulatory capacities ", EMBO J. 10(13):4177–4187 (1991).
Zardoya, et al., "Evolution and orthology of hedgehog genes", TIG 12(12):496–497 (1996).
Zecca, M. et al., "Sequential organizing activities of engrailed, hedgehog and decapentaplegic in the Drosophila wing", Dev. 121:2265–2278 (Aug. 1995).

\* cited by examiner

- DISSOCIATE P4 SCIATIC NERVE
- PLATE CELLS OVERNIGHT
- ADD Hh's AND BrdU
- FIX 18-24 HOURS LATER
- SCORE CELLS

METHODS AND COMPOSITIONS FOR TREATING OR PREVENTING PERIPHERAL NEUROPATHIES

REFERENCE TO RELATED APPLICATION

The present application is a continuation-in-part of U.S. Ser. No. 09/435,733, filed 8 Nov. 1999, the specification of which is incorporated by reference herein. U.S. Ser. No. 09/435,733 is a contiuation-in-part of U.S. Ser. No. 09/187,387, filed 6 Nov. 1998, the specification of which is also incorporated by reference herein.

BACKGROUND OF THE INVENTION

Conditions that affect components of a motor unit (motor neuron cells of the spinal cord, nerve, neuromuscular junction, and muscle fibers), sensory and autonomic nerves or their supportive structures are included in the broad category of "neuromuscular disorders", and include peripheral neuropathies.

Motor nerves are responsible for voluntary movement. Their cell bodies lie within the spinal cord, and their processes transmit signals outward to specialized motor receptors on the skeletal muscles. Sensory nerves allow the sensation of pain, vibrations or touch, and sense where limbs are positioned in space. Their cell bodies are grouped in specialized structures called sensory "ganglia" next to the spinal cord. And they transmit signals from sensory receptors in the skin and other organs inward to the central nervous system (CNS). Autonomic nerves control involuntary functions like breathing, heartbeat, blood pressure, digestion and sexual function. Their cell bodies, clustered in autonomic ganglia, are spread throughout the body.

Neuropathy is a generic term used to describe diseases of the peripheral nervous system. There are about 200 known different causes of peripheral neuropathies. Although most neuropathies affect all three types of nerve fibers, to varying degrees, some diseases involve only one or two, and are thus said to be purely or predominantly motor, sensory, or autonomic neuropathies.

For instance, Guillain-Barré syndrome is an acute illness involving the peripheral nervous system that usually occurs two to three weeks after a flu-like disease or other infections. It is mostly a motor neuropathy, meaning that its symptoms are largely related to the involvement of the motor nerves. Despite the primarily motor nature of the disease, the earliest symptoms may be numbness and tingling felt in the lower extremities followed shortly by weakness of the distal muscles of the lower extremities. The common early symptoms reported by patients are those of tripping on the toes that later results in a footdrop. The weakness usually ascends to involve the entire lower extremities and later the upper extremities. The danger occurs when the weakness involves the muscles of respiration.

The diagnosis of Guillain-Barré syndrome is suggested when the patient presents with a history of ascending weakness and a physical examination consistent with a primarily motor neuropathy. The diagnosis is confirmed with the performance of a spinal tap, which usually shows elevation of the protein level in the spinal fluid without an increase in the number of white cells and by an electromyogram. All other conditions resembling Guillain-Barré syndrome must also be excluded.

Although Guillain-Barré syndrome is usually a self-limiting illness, intensive therapeutic intervention is often needed.

CIDP or chronic inflammatory demyelinating polyneuropathy is an immune-mediated neuropathy that affects the peripheral motor and sensory nerves. The symptoms are of a slowly progressive numbness and tingling that usually starts in the feet, but later spreads to the legs and hands. The patients also complain of some weakness, again usually starting in the lower extremities, but soon involving the upper extremities. With further involvement of the sensory system, other modalities of sensations, such as balance, are affected and the patients complain of inability to walk or maintain balance in the dark.

The diagnosis of CIDP is suspected with a history of progressive sensorimotor neuropathy. Physical examination consistent with distal sensory loss in the upper and lower extremities, in conjunction with motor weakness that can be more proximal than distal supports the clinical diagnosis. The spinal tap usually shows a significant rise in the protein level of the spinal fluid. Electromyography with nerve conduction studies also supports the diagnosis. Usually the main picture is that of slowing of the conduction velocities of the peripheral nerves. The final diagnostic step would be the performance of a nerve biopsy. Finding of inflammation on the nerve biopsy, although rare, definitely confirms the diagnosis. However, the absence of inflammation does not entirely rule it out. Findings of predominant demyelination on the nerve biopsy can be used in conjunction with the other studies and the clinical presentation to suggest a diagnosis of CIDP. Once the diagnosis is secured, treatment with immunosuppressive medications can be initiated. The first line of treatment remains high-dose steroids that are initiated orally every day and then slowly tapered over time depending on the patient's improved symptomatology. Steroid failure or intolerance to steroids necessitates the use of other immunosuppressing agents. However, better therapeutic intervention for CIDP is still a desired objective of the present invention.

Peripheral neuropathy is one of the many complications of long-standing diabetes. Usually neuropathy occurs about 8 to 10 years after the onset of diabetes. However, it is not uncommon to see patients presenting with neuropathic symptoms that have their diabetes diagnosed at that time or patients with 20 or more years of diabetes with little or no evidence of neuropathy. The symptoms of diabetic neuropathy consist of a slow and insidious numbness and tingling of the lower extremities that can progress to become a painful neuropathy. The pain is usually described as a burning sensation in the feet. Occasionally, the pain is described as a sensation of sharp, electric jolts traveling down the lower extremities. As it worsens, the pain acquires a deep bony nature. It tends to be worse at night commonly preventing or awakening the patients from sleep. As the neuropathy worsens, it affects the upper extremities and may involve the motor nerves with the complaint of weakness in the distal muscles of the legs and arms. The neuropathy of diabetes can also involve the autonomic nervous system causing problems with sweating, blood pressure, and sexual function.

Diabetic neuropathy is suspected when the patient's history and physical examination are compatible with the clinical picture in a setting of diabetes. In the absence of the history of diabetes, diagnostic tests to rule out diabetes is required. The workup is completed by the performance of an electromyogram with nerve conduction studies to quantitate the extent of involvement of the peripheral nervous system.

Diabetic neuropathy, unfortunately, has no effective treatment at this point in the art. Adequate control of the patient's blood sugar, however, has been shown to slow the progression of the symptoms. Symptomatic treatment with various medications that suppress neuropathic pain, including Elavil, Tegretol and more recently Ultram, have been successful. Thus, a more effective treatment for diabetic neuropathy is an objective of the present invention.

Other common causes of neuropathy such include alcoholism or medication induced neuropathies, neuropathies resulting from trauma, such as crushed nerves, as well as inherited forms of such disorders.

SUMMARY OF THE INVENTION

One aspect of the present application relates to a method for treating or alleviating all or a portion of the symptoms attendent neuromuscular disorders, and in particular, in the treatment of peripheral neuropathies. Briefly, the subject method comprises contacting the afflicted tissue with a hedgehog therapeutic or ptc therapeutic (defined infra) in an amount effective to alter the growth state of the treated cells, e.g., relative to the absence of administeration of the hedgehog therapeutic or ptc therapeutic.

Wherein the subject method is carried out using a hedgehog therapeutic, the hedgehog therapeutic preferably a polypeptide including a hedgehog portion comprising at least a bioactive extracellular portion of a hedgehog protein. e.g., the hedgehog portion includes at least 50, 100 or 150 (contiguous) amino acid residues of an N-terminal half of a hedgehog protein. In preferred embodiments, the hedgehog portion includes at least a portion of the hedgehog protein corresponding to a 19 kd fragment of the extracellular domain of a hedgehog protein.

In preferred embodiments, the hedgehog portion has an amino acid sequence at least 60, 75, 85, or 95 percent identical with a hedgehog protein of any of SEQ ID Nos. 10–18 or 20, though sequences identical to those sequence listing entries are also contemplated as useful in the present method. The hedgehog portion can be encoded by a nucleic acid which hybridizes under stringent conditions to a nucleic acid sequence of any of SEQ ID Nos. 1–9 or 19, e.g., the hedgehog portion can be encoded by a vertebrate hedgehog gene, especially a human hedgehog gene.

In other embodiments, the subject method can be carried out by administering a gene activation construct, wherein the gene activation construct is deigned to recombine with a genomic hedgehog gene of the patient to provide a heterologous transcriptional regulatory sequence operatively linked to a coding sequence of the hedgehog gene.

In still other embodiments, the subject method can be practiced with the administration of a gene therapy construct encoding a hedgehog polypeptide. For instance, the gene therapy construct can be provided in a composition selected from a group consisting of a recombinant viral particle, a liposome, and a poly-cationic nucleic acid binding agent, In yet other embodiments, the subject method can be carried out using a ptc therapeutic. An exemplary ptc therapeutic is a small organic molecule which binds to a patched protein and derepresses patched-mediated inhibition of mitosis, e.g., a molecule which binds to patched and mimics hedgehog-mediated patched signal transduction, which binds to patched and regulates patched-dependent gene expression. For instance, the binding of the ptc therapeutic to patched may result in upregulation of patched and/or gli expression.

In a more generic sense, the ptc therapeutic can be a small organic molecule which interacts with MK cells to induce hedgehog-mediated patched signal transduction, such as by altering the localization, protein-protein binding and/or enzymatic activity of an intracellular protein involved in a patched signal pathway. For instance, the ptc therapeutic may alter the level of expression of a hedgehog protein, a patched protein or a protein involved in the intracellular signal transduction pathway of patched.

In certain embodiments, the ptc therapeutic is an antisense construct which inhibits the expression of a protein which is involved in the signal transduction pathway of patched and the expression of which antagonizes hedgehog-mediated signals. The antisense construct is perferably an oligonucleotide of about 20–30 nucleotides in length and having a GC content of at least 50 percent.

In other embodiments, the ptc therapeutic is an inhibitor of protein kinase A (PKA), such as a 5-isoquinolinesulfonamide. The PKA inhibitor can be a cyclic AMP analog. Exemplary PKA inhibitors include N-[2-((p-bromocinnamyl)amino)ethyl]-5-isoquinolinesulfonamide, 1-(5-isoquinoline-sulfonyl)-2-methylpiperazine, KT5720, 8-bromo-cAMP, dibutyryl-cAMP and PKA Heat Stable Inhibitor isoform α. Another exemplary PKA inhibitor is represented in the general formula:

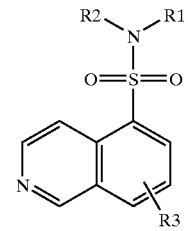

wherein, $R_1$ and $R_2$ each can independently represent hydrogen, and as valence and stability permit a lower alkyl, a lower alkenyl, a lower alkynyl, a carbonyl (such as a carboxyl, an ester, a formate, or a ketone), a thiocarbonyl (such as a thioester, a thioacetate, or a thioformate), an amino, an acylamino, an amido, a cyano, a nitro, an azido, a sulfate, a sulfonate, a sulfonamido, —$(CH_2)_m$—$R_8$, —$(CH_2)_m$—OH, —$(CH_2)_m$—O-lower alkyl, —$(CH_2)_m$—O-lower alkenyl, —$(CH_2)_n$—O—$(CH_2)_m$—$R_8$, —$(CH_2)_m$—SH, —$(CH_2)_m$—S-lower alkyl, —$(CH_2)_m$—S-lower alkenyl, —$(CH_2)_n$—$S_{(CH2)}$—$R_8$, or $R_1$ and $R_2$ taken together with N form a heterocycle (substituted or unsubstituted);

$R_3$ is absent or represents one or more substitutions to the isoquinoline ring such as a lower alkyl, a lower alkenyl, a lower alkynyl, a carbonyl (such as a carboxyl, an ester, a formate, or a ketone), a thiocarbonyl (such as a thioester, a thioacetate, or a thioformate), an amino, an acylamino, an amido, a cyano, a nitro, an azido, a sulfate, a sulfonate, a sulfonamido, —$CH)_m$—$R_8$, —$(CH_2)_m$—OH, —$(CH_2)_m$—O-lower alkyl, —$(CH_2)_m$—O-lower alkenyl, —$(CH_2)_n$—O—$(CH_2)_m$—$R_8$, —$(CH_2)_m$—SH, —$(CH_2)_m$—S-lower alkyl, —$(CH_2)_m$—S-lower alkenyl, —$(CH_2)_n$—$S_{(CH2)}$—$R_8$;

$R_8$ represents a substituted or unsubstituted aryl, aralkyl, cycloalkyl, cycloalkenyl, or heterocycle; and n and m are independently for each occurrence zero or an integer in the range of 1 to 6.

SHH500=animals treated with 500 ug/kg SHH and cisplatin; SHH50=animals treated with 50 ug/kg SHH and cisplatin. The compounds were administered 3 times per week subcutaneously. The weights are expressed in grams, as means±SEM. Post-hoc comparison to vehicle group was performed with Fisher test; *:significantly different at p<0.05; :significantly different at p<0.01; *;significantly different at p<0.001.

Figure 2:
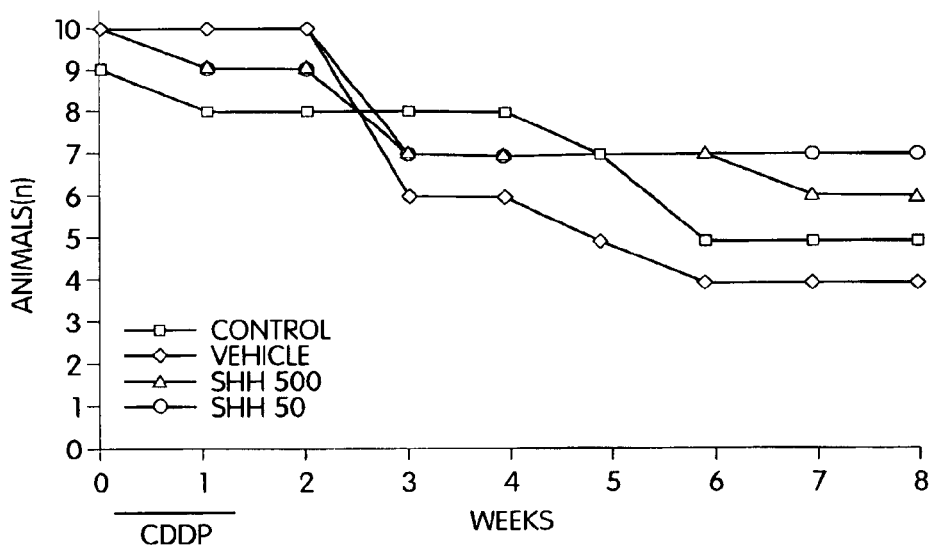

FIG. 2. Number of animals present throughout the study in treated or control mice. The number of animals in each group was compared by repeated Anova test and was not found to be significantly different between groups.

Figure 3:
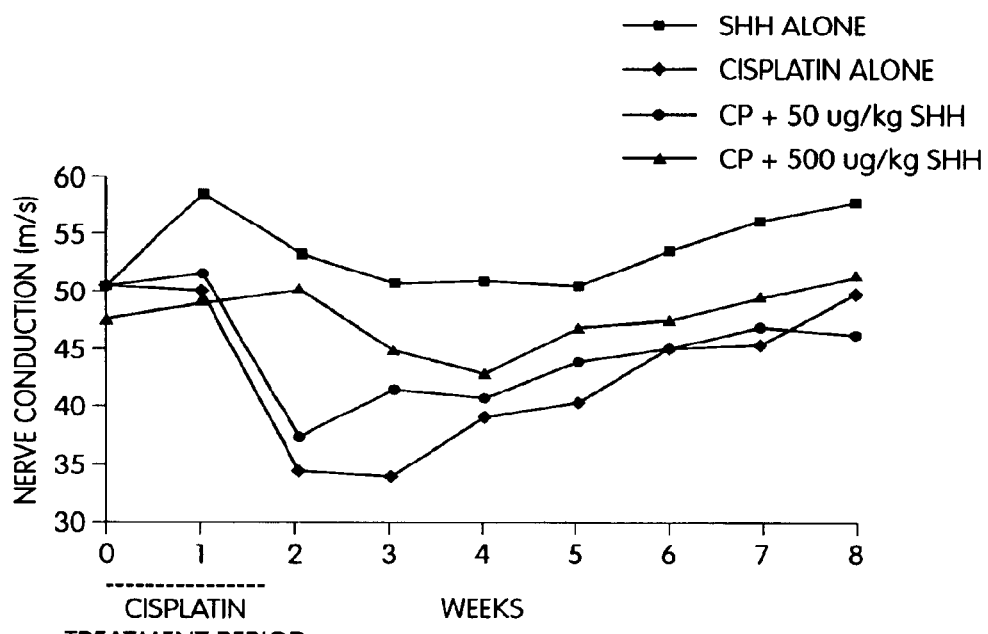

FIG. 3. Time course of sensory nerve conduction velocity (SNCV) measured in treated or control mice. Results are expressed in m/sec, as means±SEM. Post-hoc comparison to vehicle group was performed with Fisher test; *:significantly different at p<0.05; :significantly different at p<0.01; *:significantly different at p<0.001.

Figure 4:
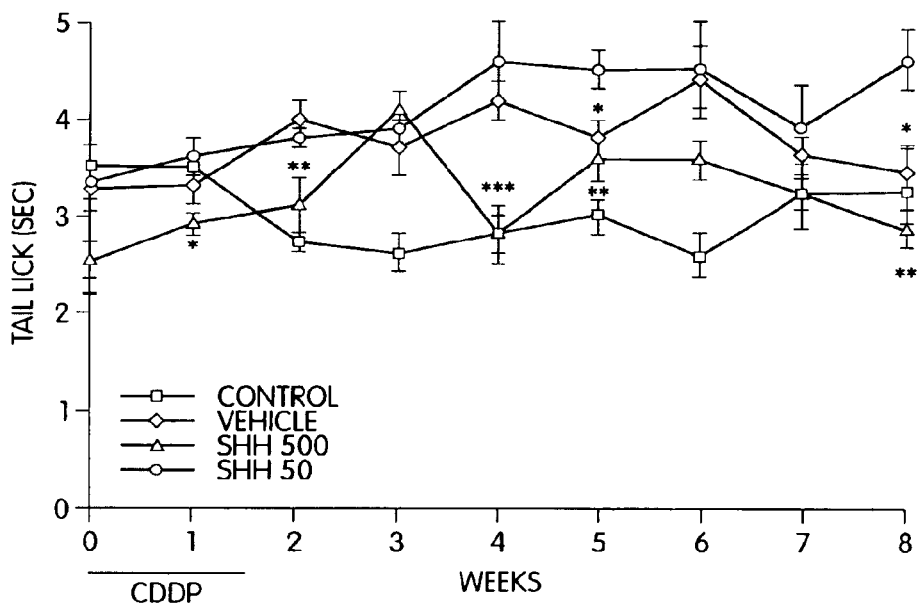

FIG. 4. Tail flick latency measured in treated or control mice. Results are expressed in sec, as means±SEM. Post-hoc comparison to vehicle group was performed with Fisher test; *:significantly different at p<0.05; :significantly different at p<0.01; *:significantly different at p<0.001.

Figure 5:
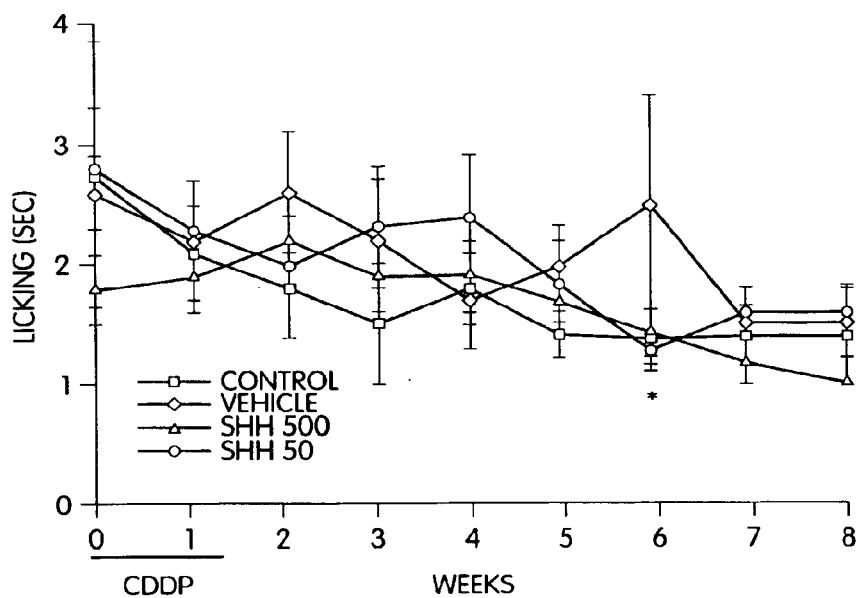

FIG. 5. Latency to lick the paw measured in treated or control mice. Results are expressed in sec as means±SEM. Post-hoc comparison to vehicle group was performed with Fisher test.

Figure 6:
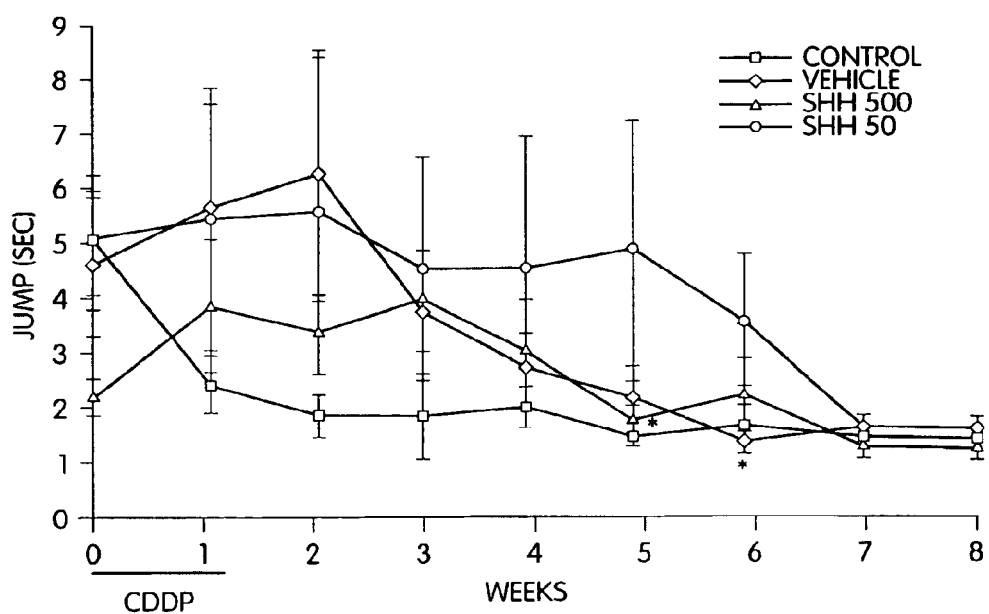

FIG. 6. Latency before first jump measured in treated or control mice. Results are expressed in sec, as means±SEM. Post-hoc comparison to vehicle group was performed with Fisher test; *:significantly different at p<0.05.

Figure 7:
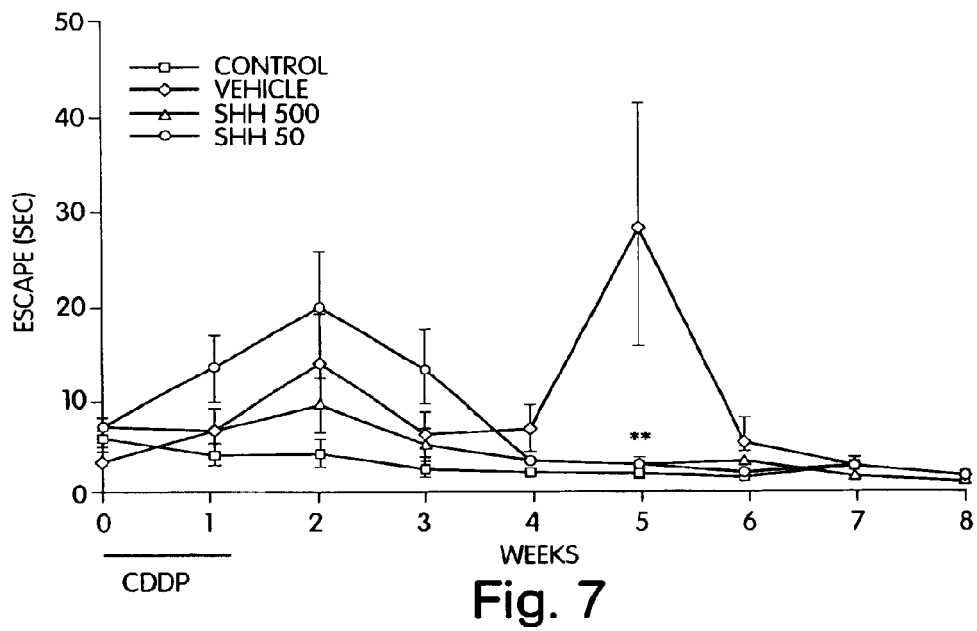

FIG. 7. Latency before adjusted jump measured in treated or control mice. Results are expressed in sec, as means±SEM. Post-hoc comparison to vehicle group was performed with Fisher test.

Figure 8:
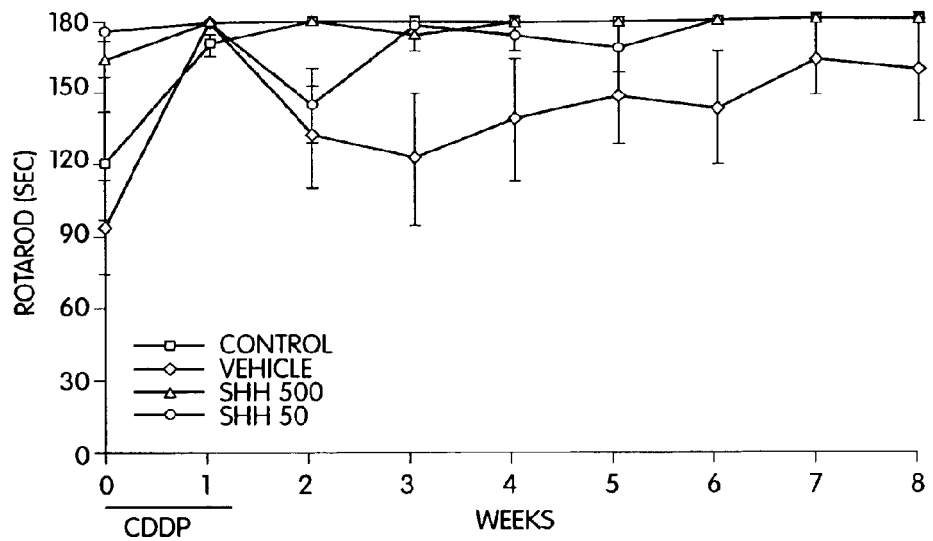

FIG. 8. Ability to stay on rotarod measured in treated or control mice.

Figure 9:
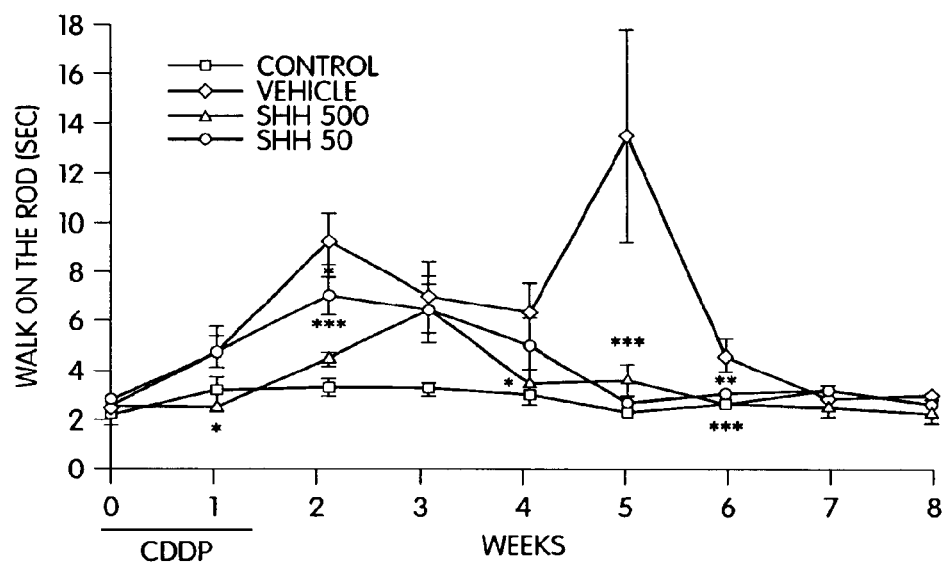

FIG. 9. Duration of the walk on a rod needed to reach the platform, measured in treated or control mice. Results are expressed in sec, as means+SEM. Post-hoc comparison to vehicle group was performed with Fisher test; *:significantly different at p<0.05; :significantly different at p<0.01; *: significantly different at p<0.001.

Figure 10A:
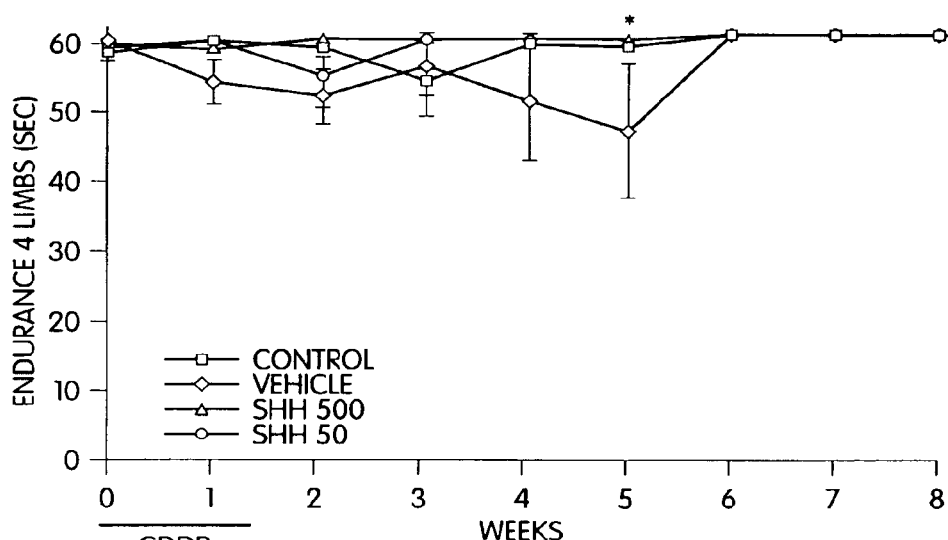
Figure 10B:
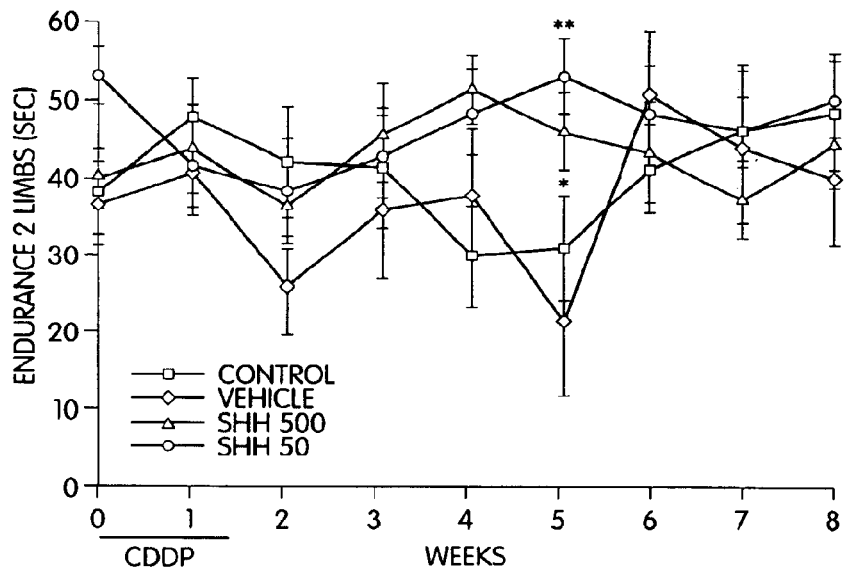

FIGS. 10A and 10B. Ability to hold a weight with four limbs (10a) or only forelimbs (10b) measured in treated or control mice. Results are expressed in sec, as means+SEM. Post-hoc comparison to vehicle group was performed with Fisher test; *:significantly different at p<0.05; **:significantly different at p<0.01.

Figure 11A:
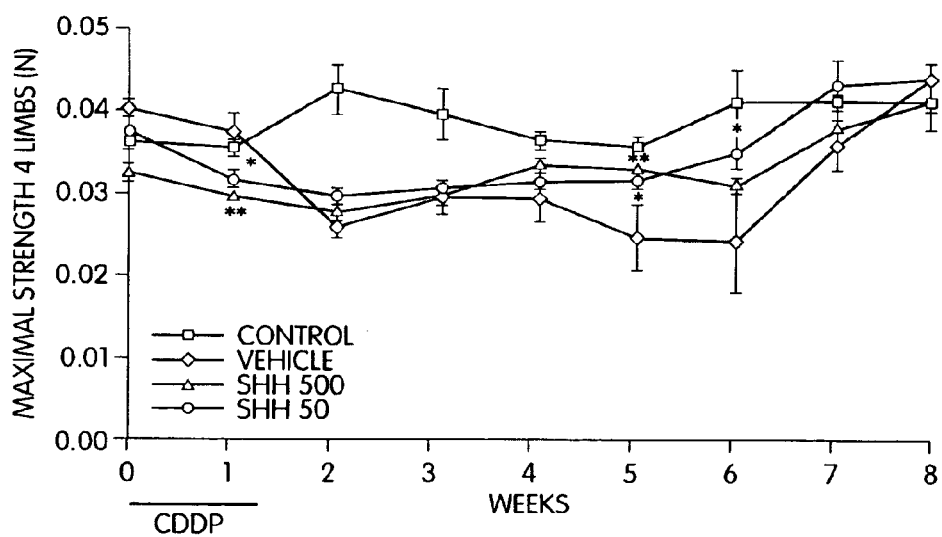
Figure 11B:
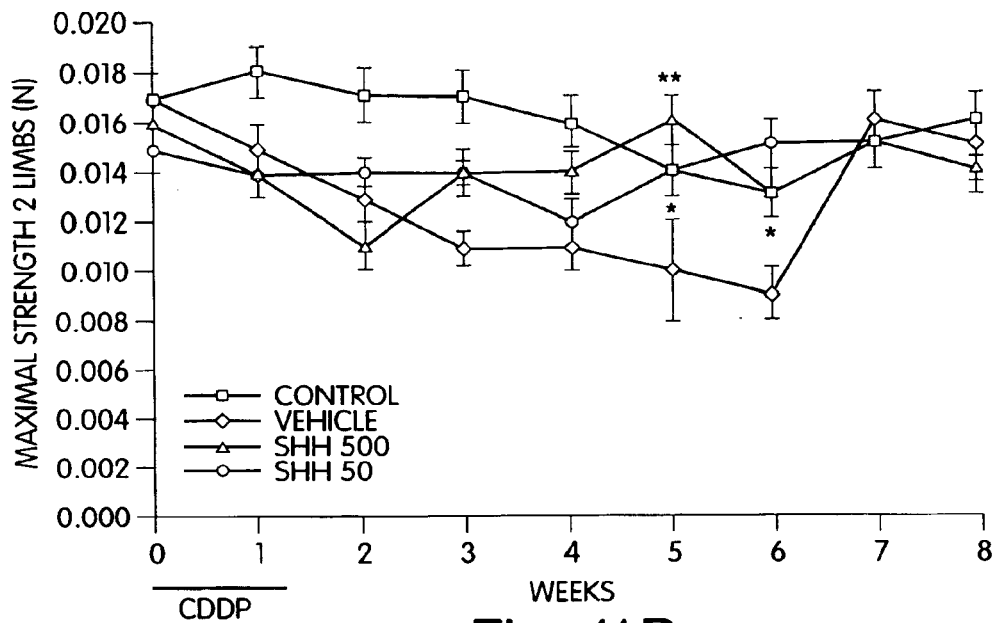

FIGS. 11A and 11B. Maximal strength exercised with four limbs (11a) or only forelimbs (11b) measured in treated or control mice. Results are expressed in sec, as means±SEM. Post-hoc comparison to vehicle group was performed with Fisher test; *:significantly different at p<0.05; :significantly different at p<0.01; *:significantly different at p<0.001.

Figure 12:
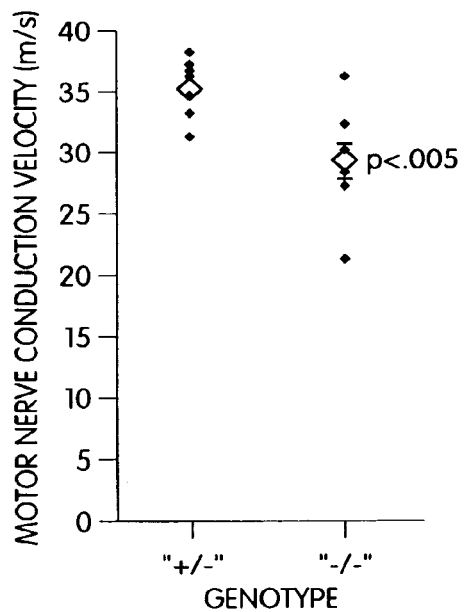

FIG. 12. Graph of motor neuron velocity in normal and Dhh$^{-/-}$ mice

Figure 13A:
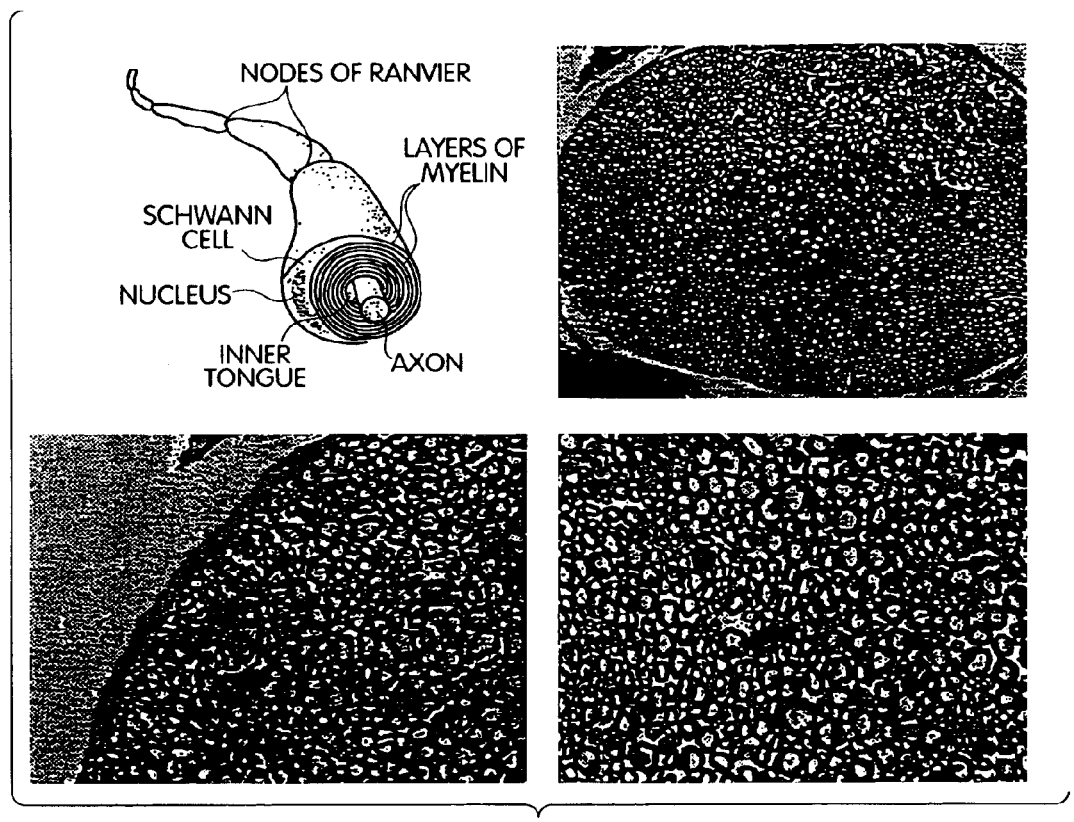
Figure 13B:
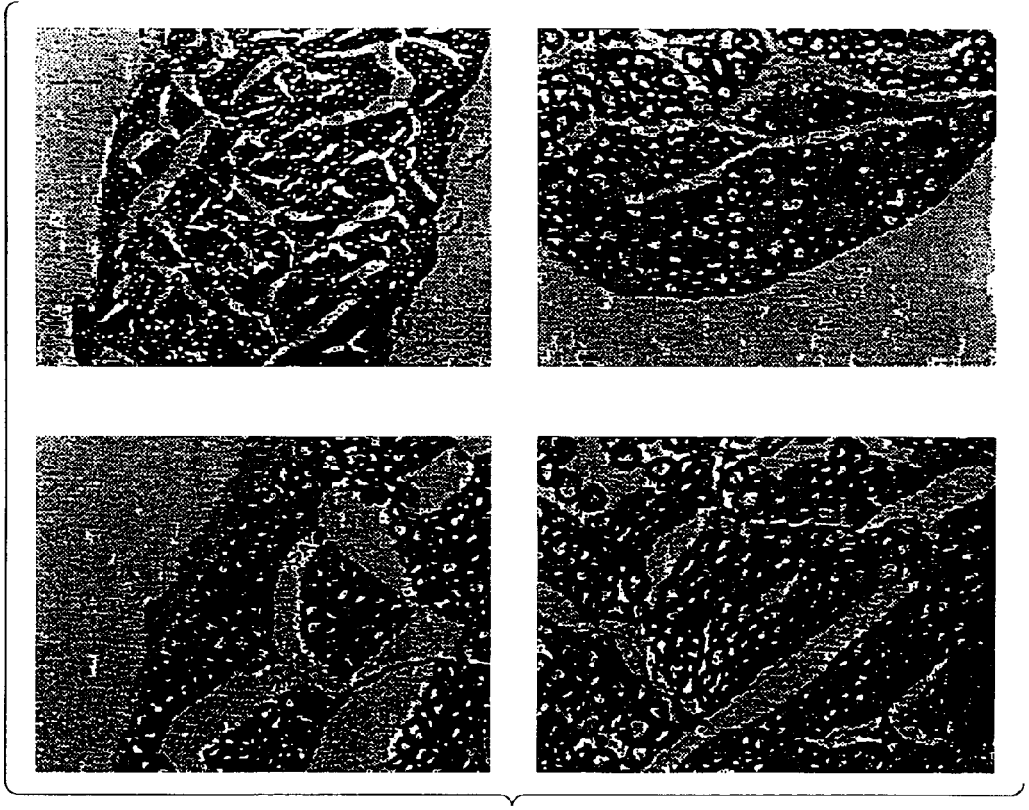

FIGS. 13A and 13B. Micrographs of peripheral nerve cells in normal and Dhh$^{-/-}$ mice.

Figure 14A:
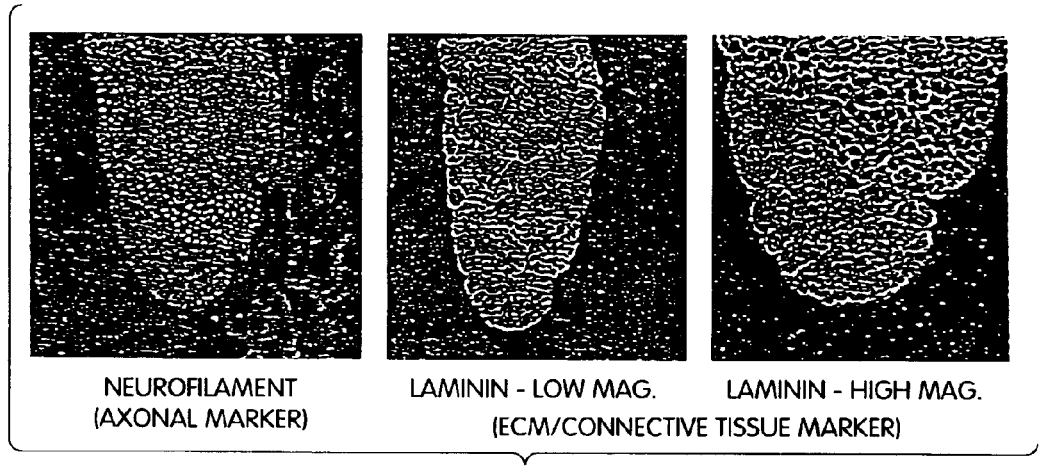
Figure 14B:
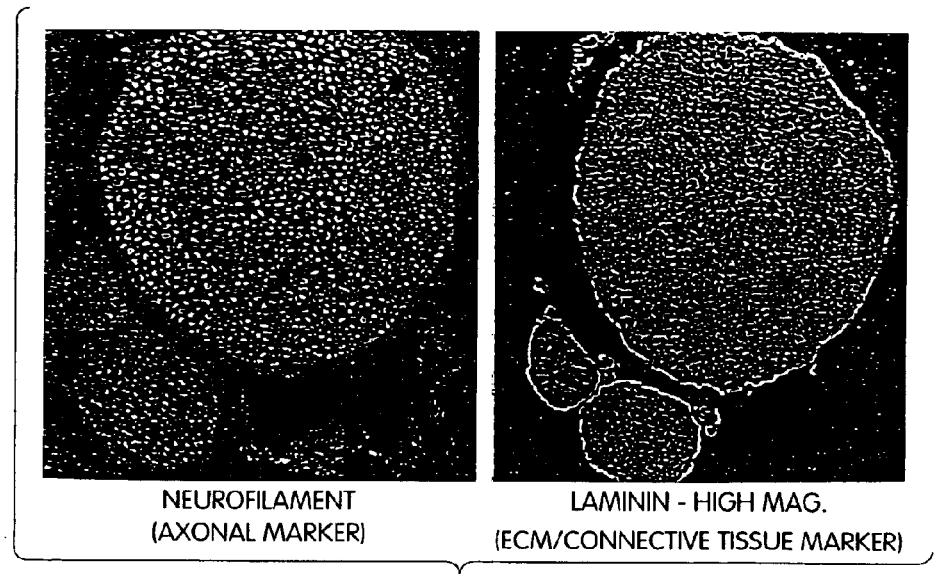

FIGS. 14A and 14B. Immunohistochemical stains of peripheral nerves using antibodies for neurofilament (an axonal marker) and Laminin (and ECM/connective tissue marker).

Figure 15:
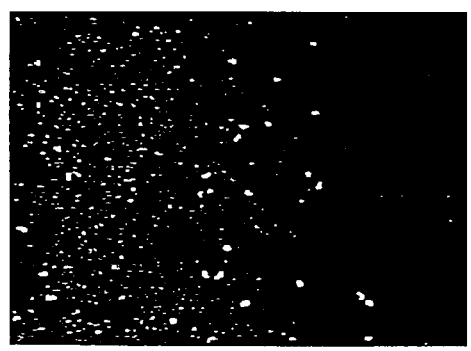
Figure 15:
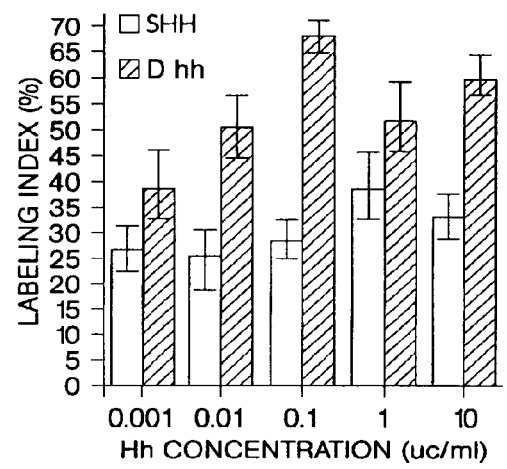

FIG. 15. Effects of hedgehog on perineural cell proliferation.

Figure 16:
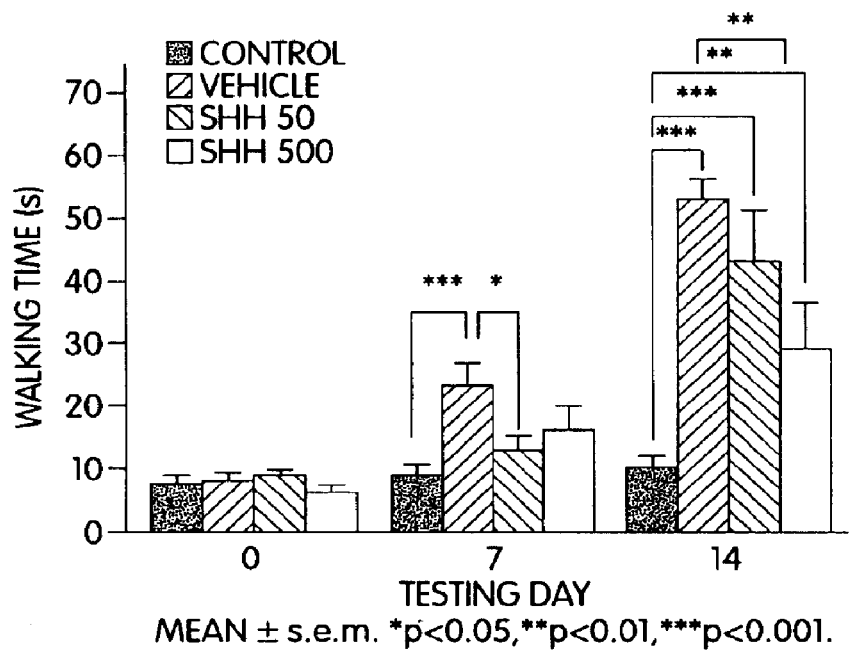

FIG. 16. Running time (walking test) in control and treated mice.

Figure 17:
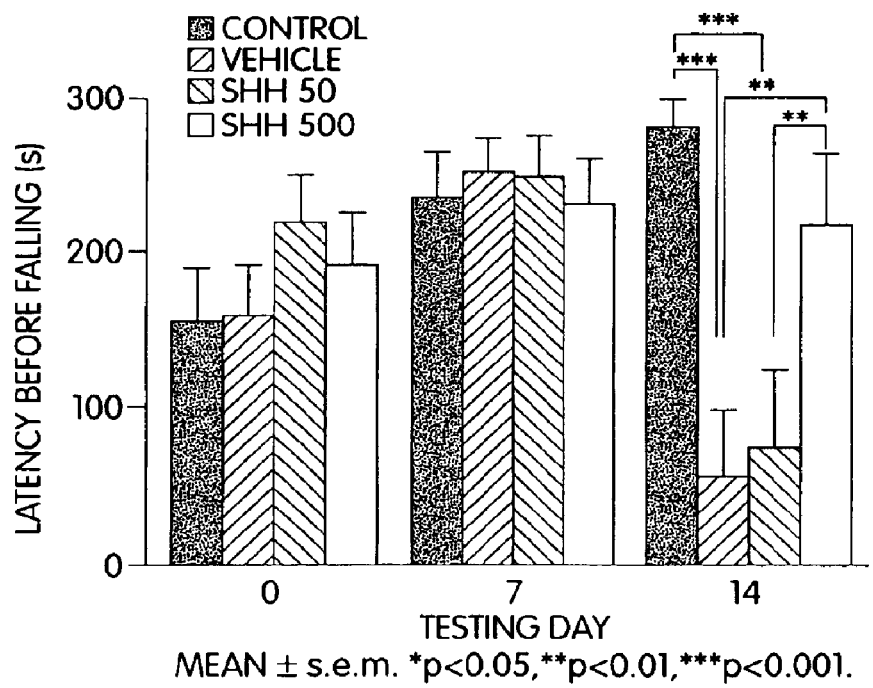

FIG. 17. Time before falling from the rotarod in control and treated mice.

Figure 18:
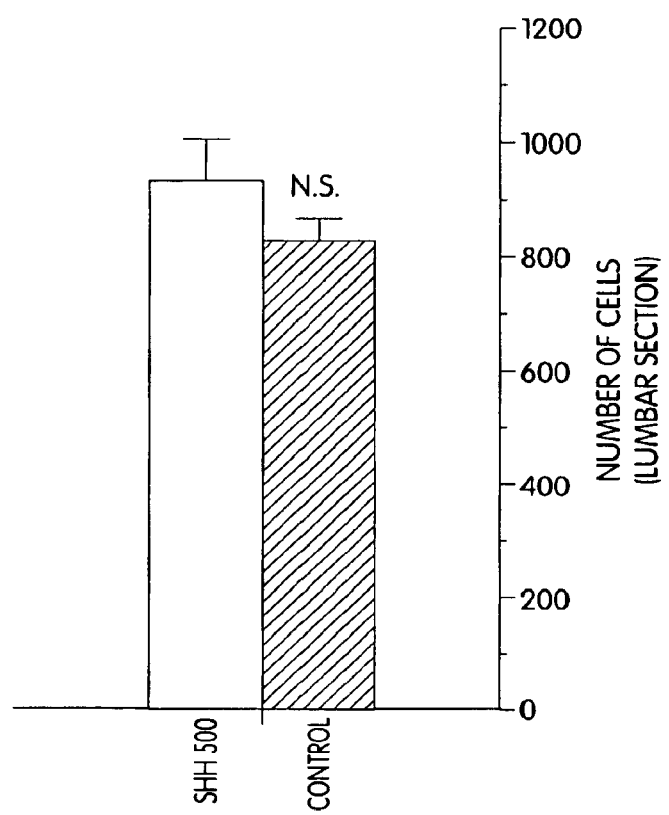

FIG. 18. Histological study of SOD mice treated with 500 µg/kg SHH. Motoneurons were counted in ventral horns of lumbar spinal cord sections originating from 100 day-old hSOD mice, after cresyl violet staining.

Figure 19:
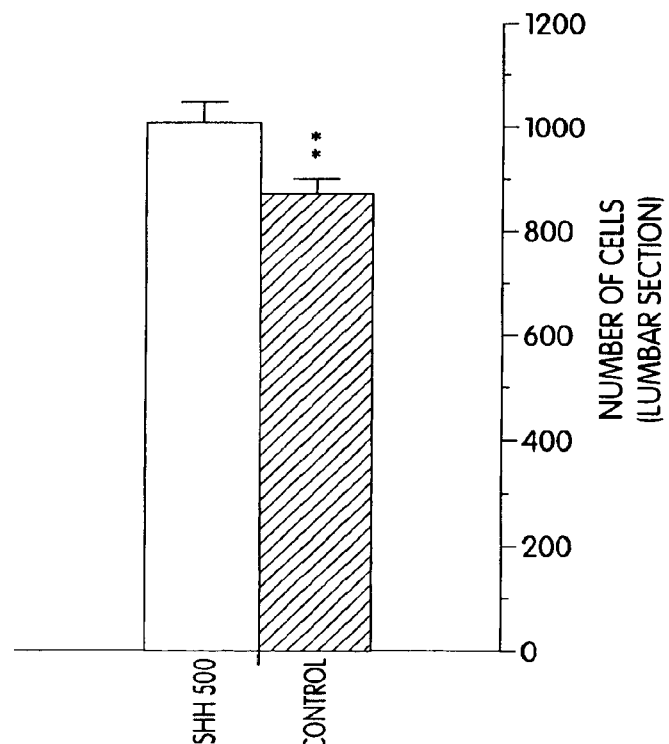

FIG. 19. Histological study of SOD mice treated with 500 µg/kg SHH (without Y0 littermate).

Figure 20:
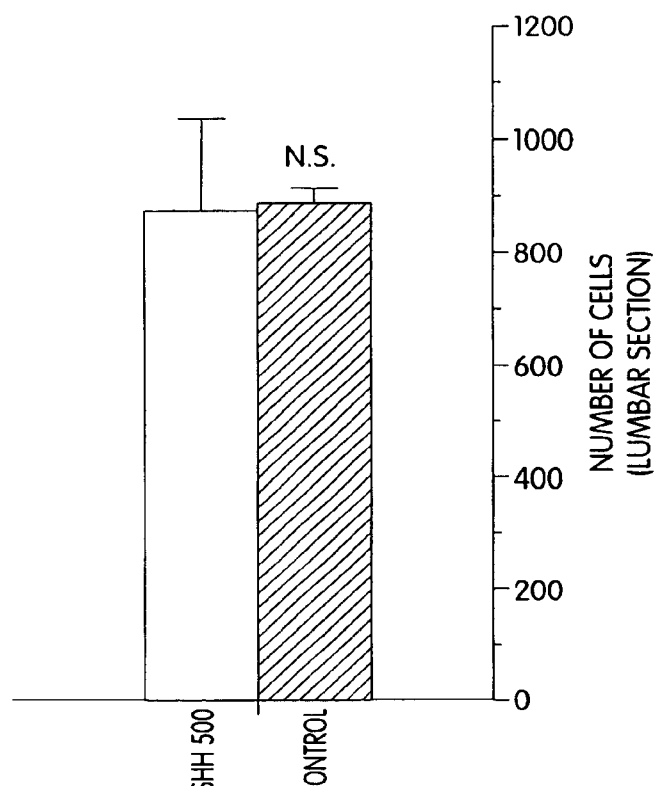

FIG. 20. Histological study of male SOD mice treated with 500 µg/kg SHH.

Figure 21:
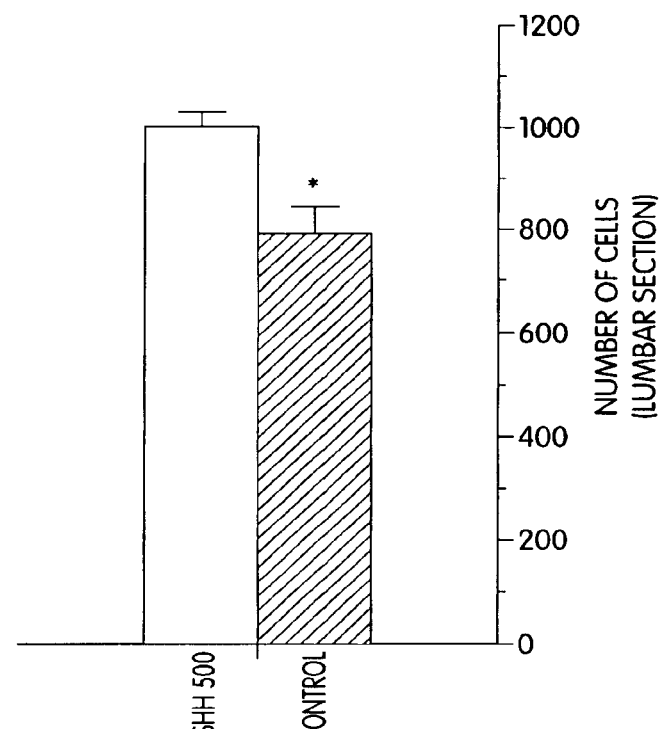

FIG. 21. Histological study of female SOD mice treated with 500 µg/kg SHH

Figure 22:
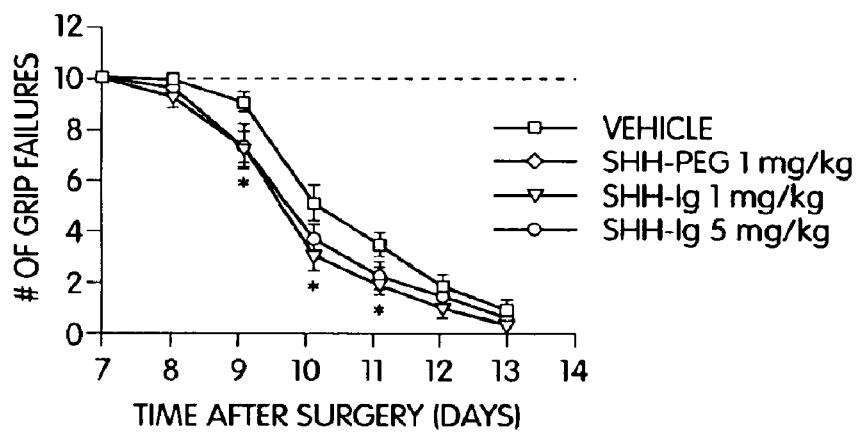

FIG. 22. Evaluating the effect of Hedgehog proteins on ability to grip following sciatic nerve crush injury.

Figure 23:
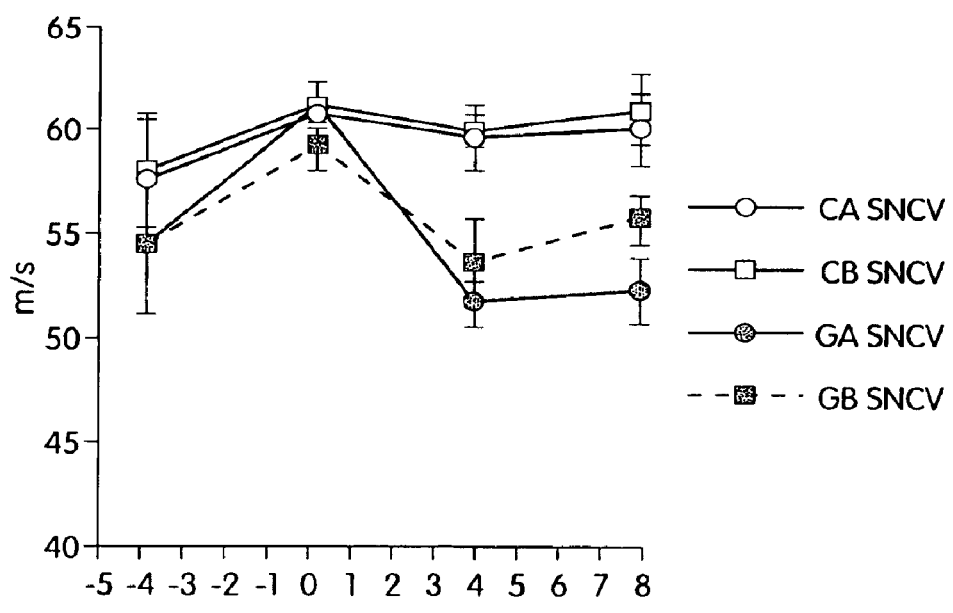

FIG. 23. Evaluating the effect of Hedgehog protein on sensory nerve conduction velocity in galactose intoxication-mediated neuropathies. CA=normal animal treated with control; CB=normal animal treated with Shh; GA=galactose intoxicated animal treated with vehicle; and GB=galactose intoxicated animal treated with Shh.

Figure 24:
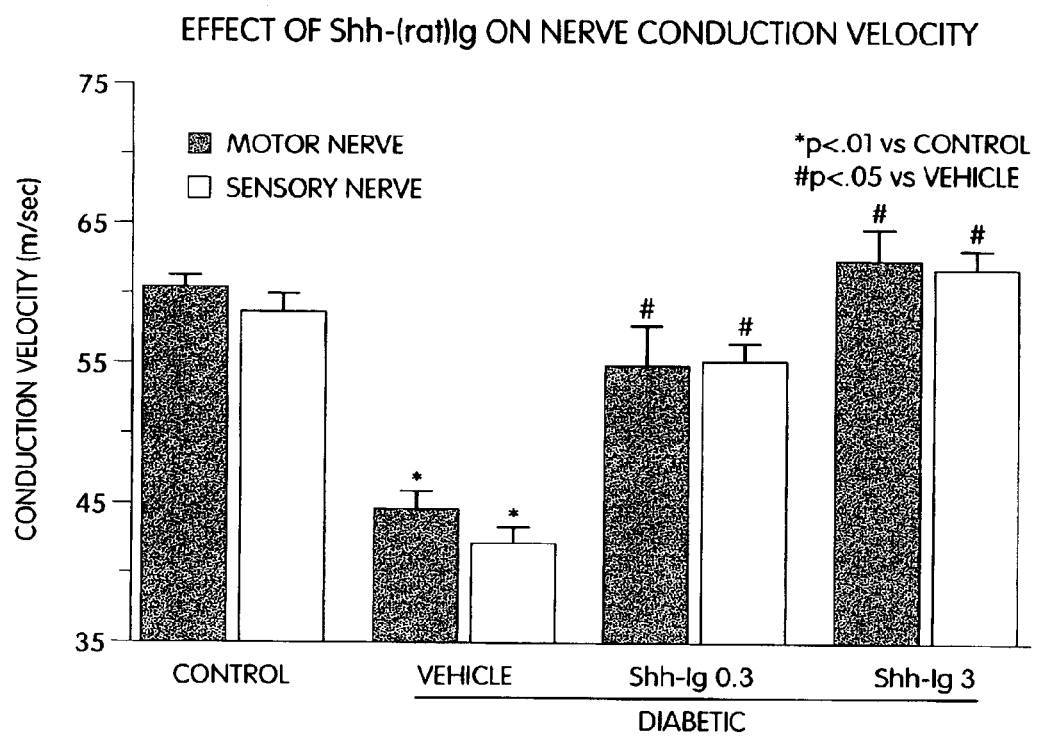

FIG. 24. Effects of Shh-(rat)Ig on nerve conduction velocity in streptozotocin-treated rats.

Figure 25:
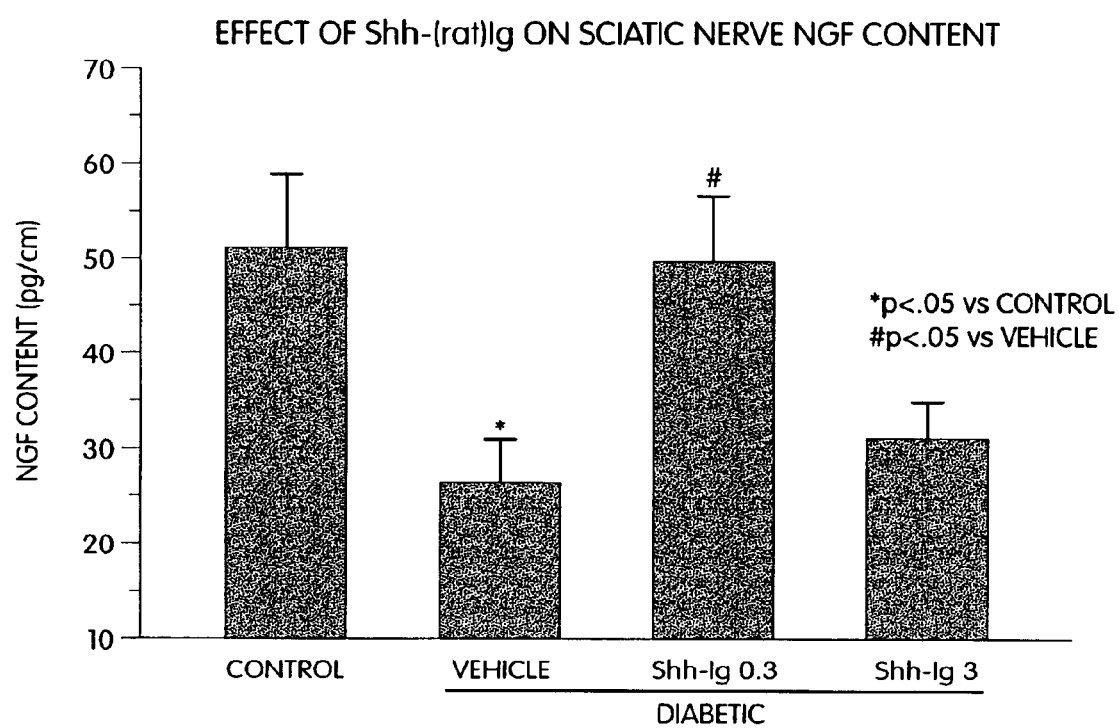

FIG. 25. Effect of Shh-(rat)Ig on sciatic nerve NGF content in streptozotocin-treated rats.

Figure 26:
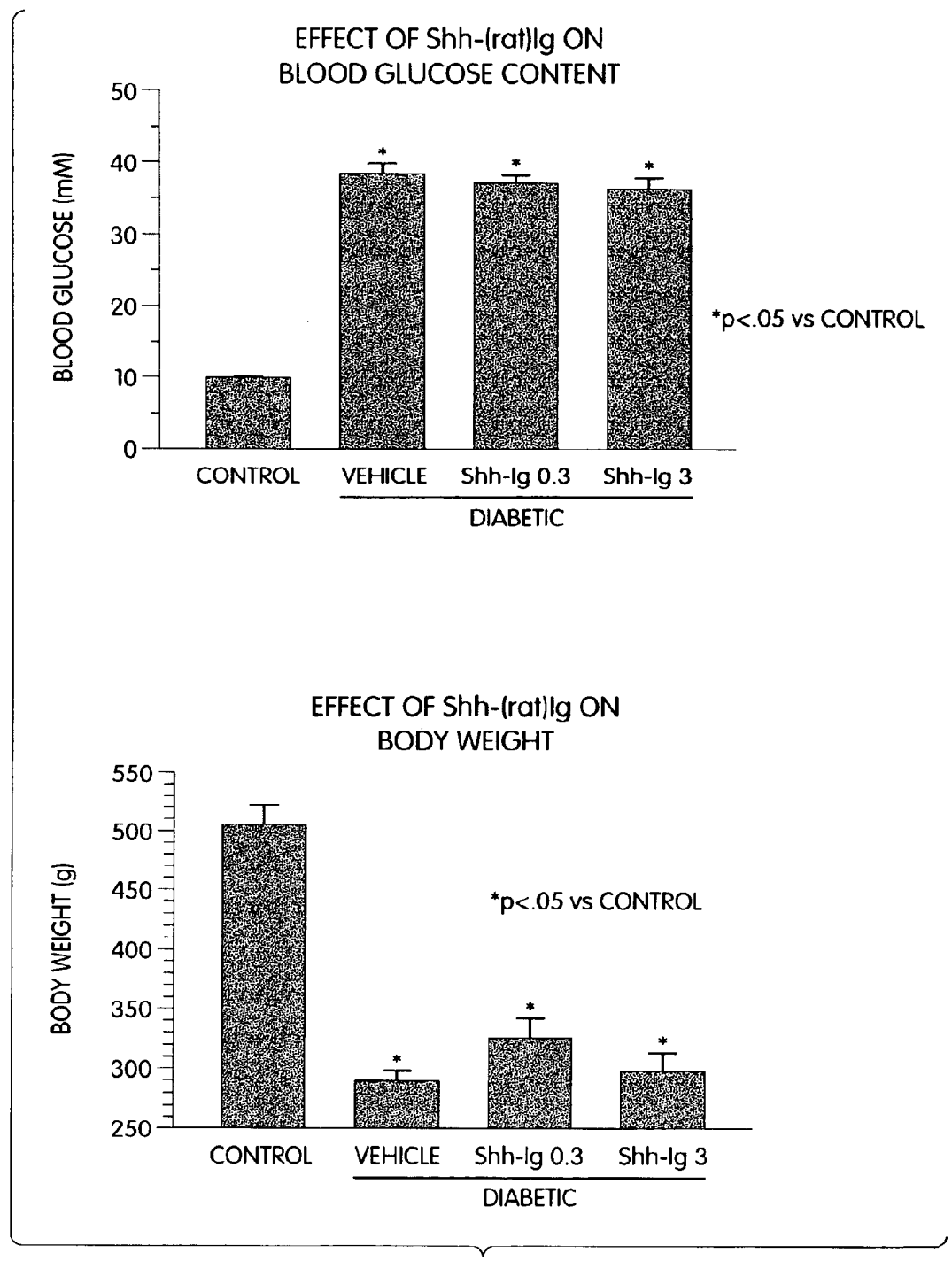

FIG. 26. Effect of Shh-(rat)Ig on blood glucose content and body weight in streptozotocin-treated rats.

Figure 27:
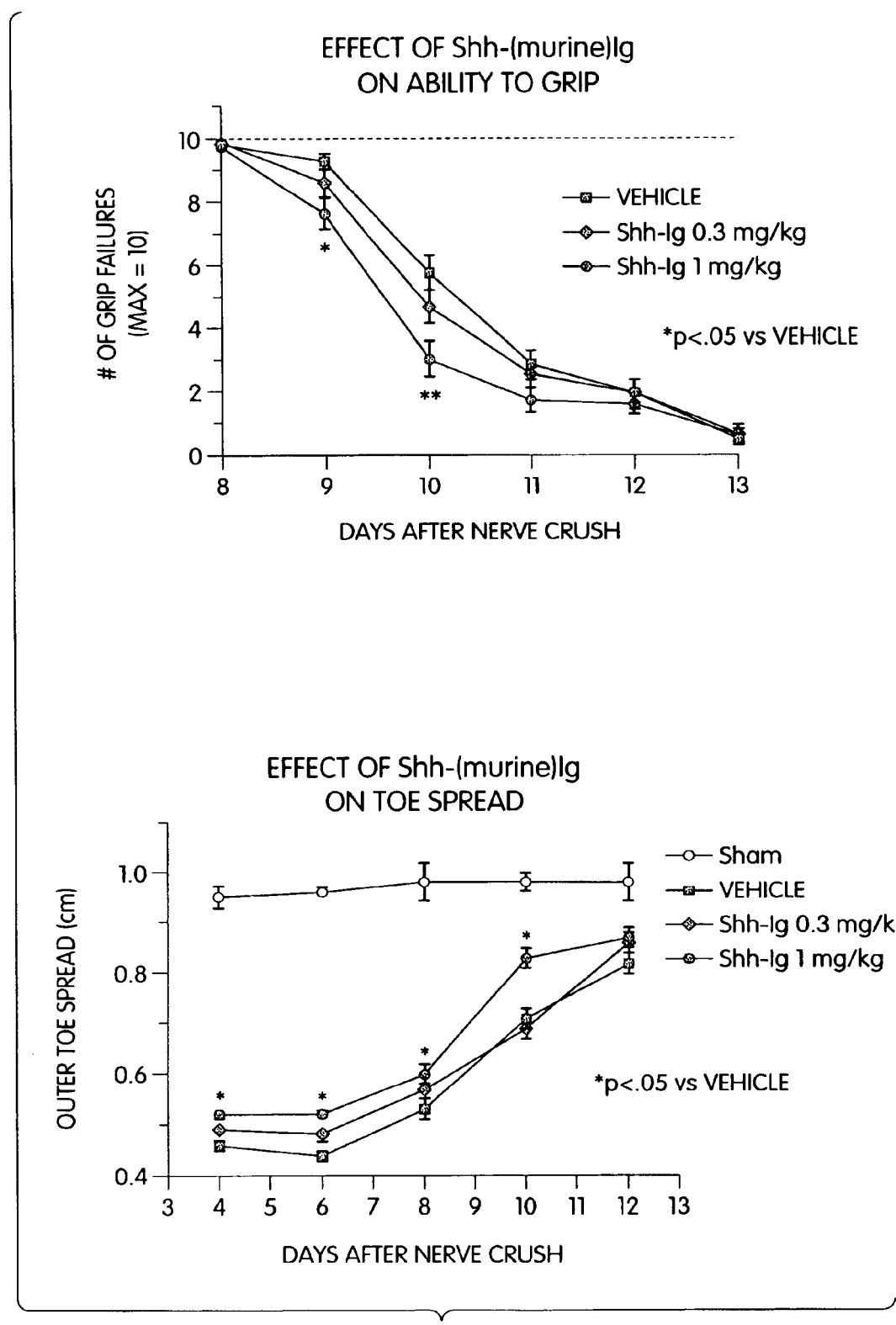

FIG. 27. Effect of Shh-(murine)Ig on nerve crush regeneration.

Figure 28:
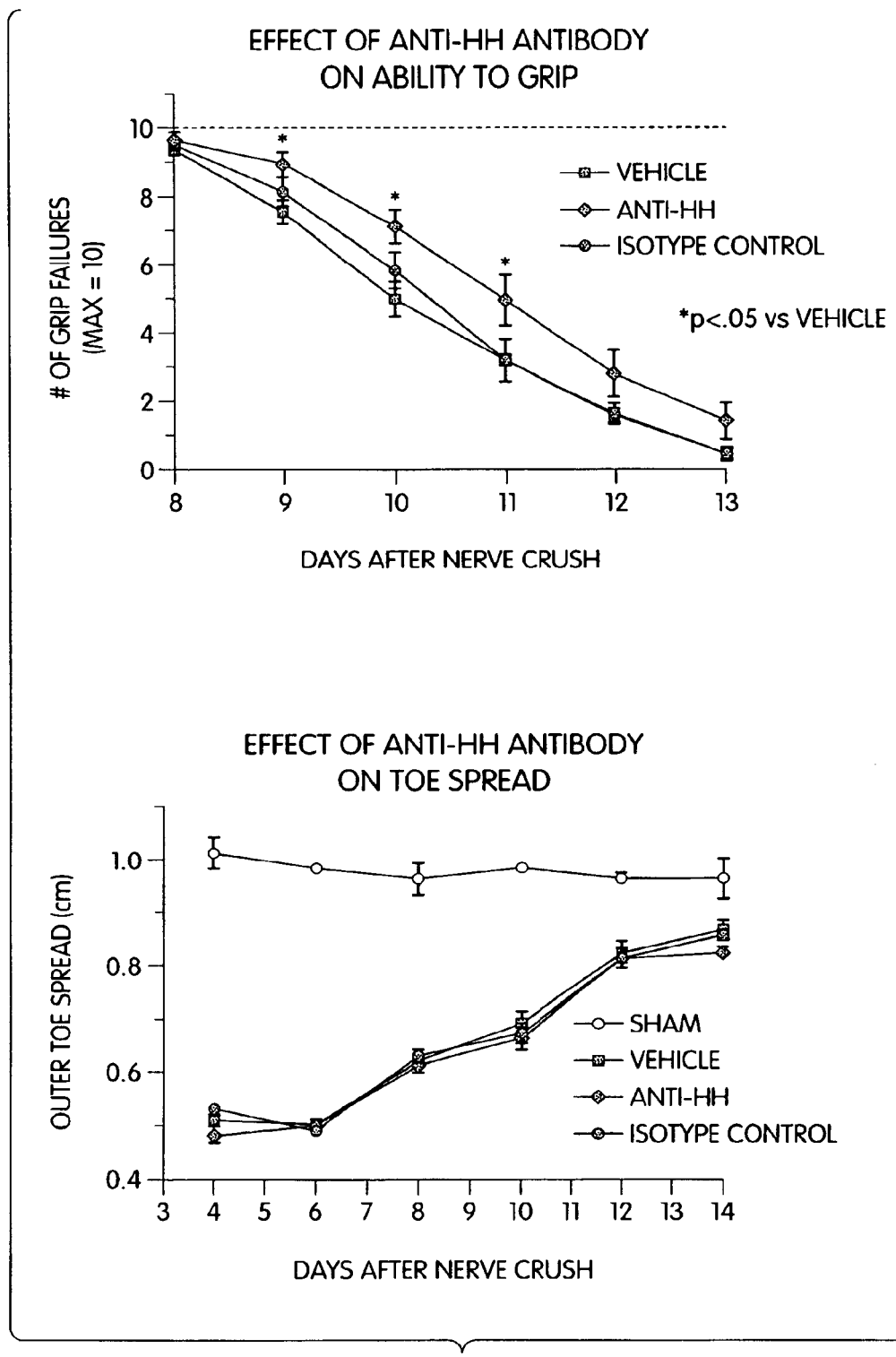

FIG. 28. Effect of anti-hedgehog antibody on nerve crush regeneration.

Figure 29:
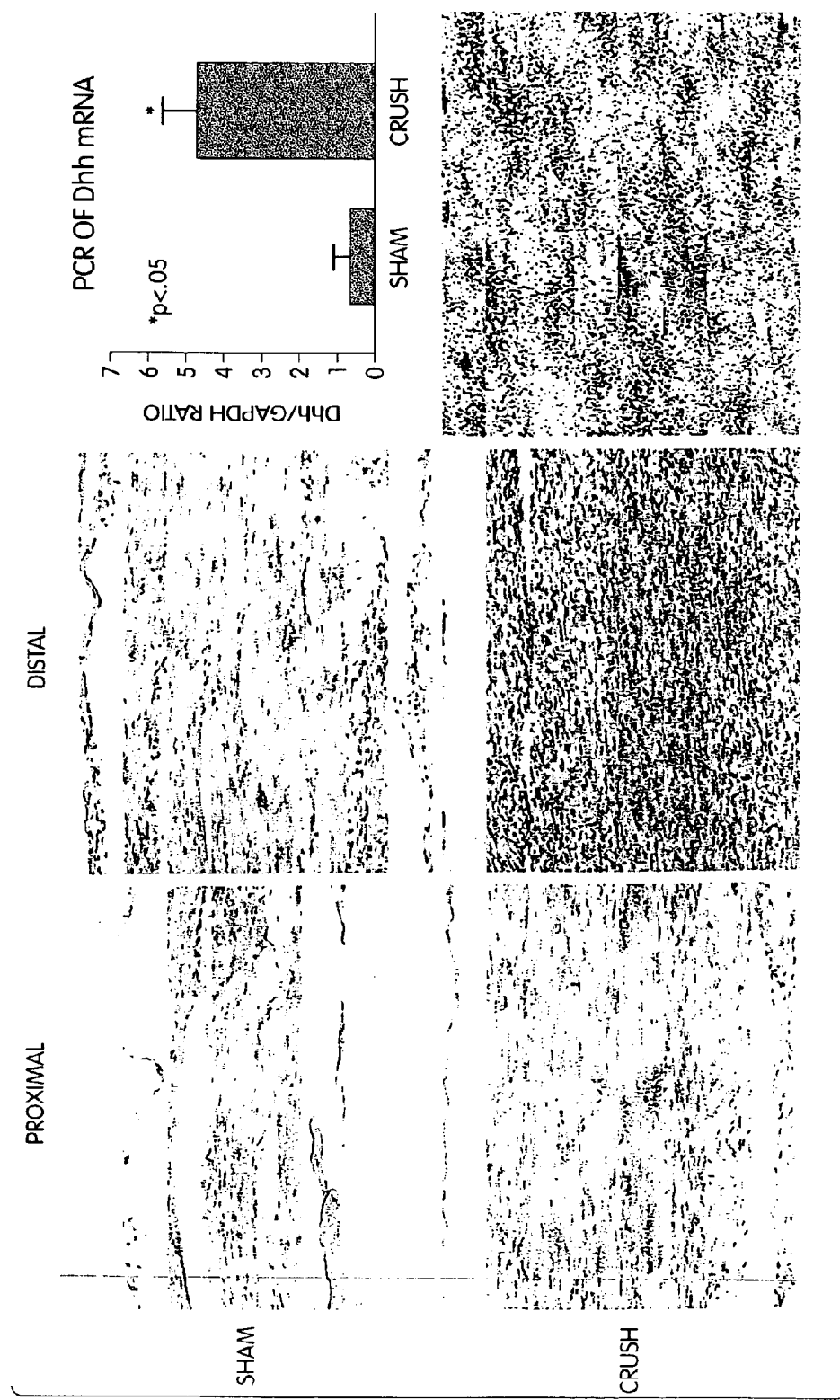

FIG. 29. Hedgehog pathway expression after sciatic nerve crush—Dhh at 13 days

Figure 30:
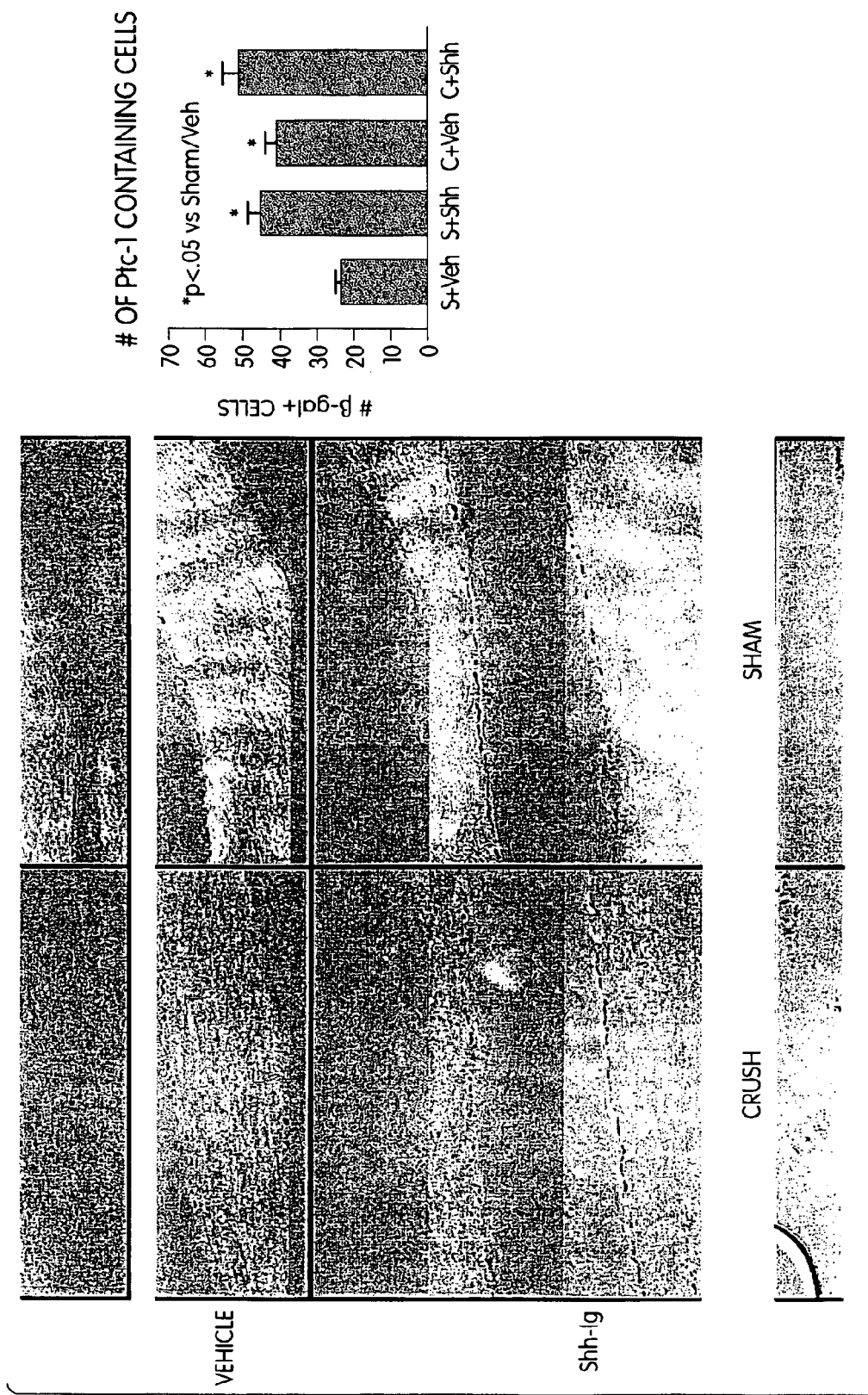

FIG. 30. Hedgehog pathway expression after sciatic nerve crush—Ptc-1 at 13 days

Figure 31:
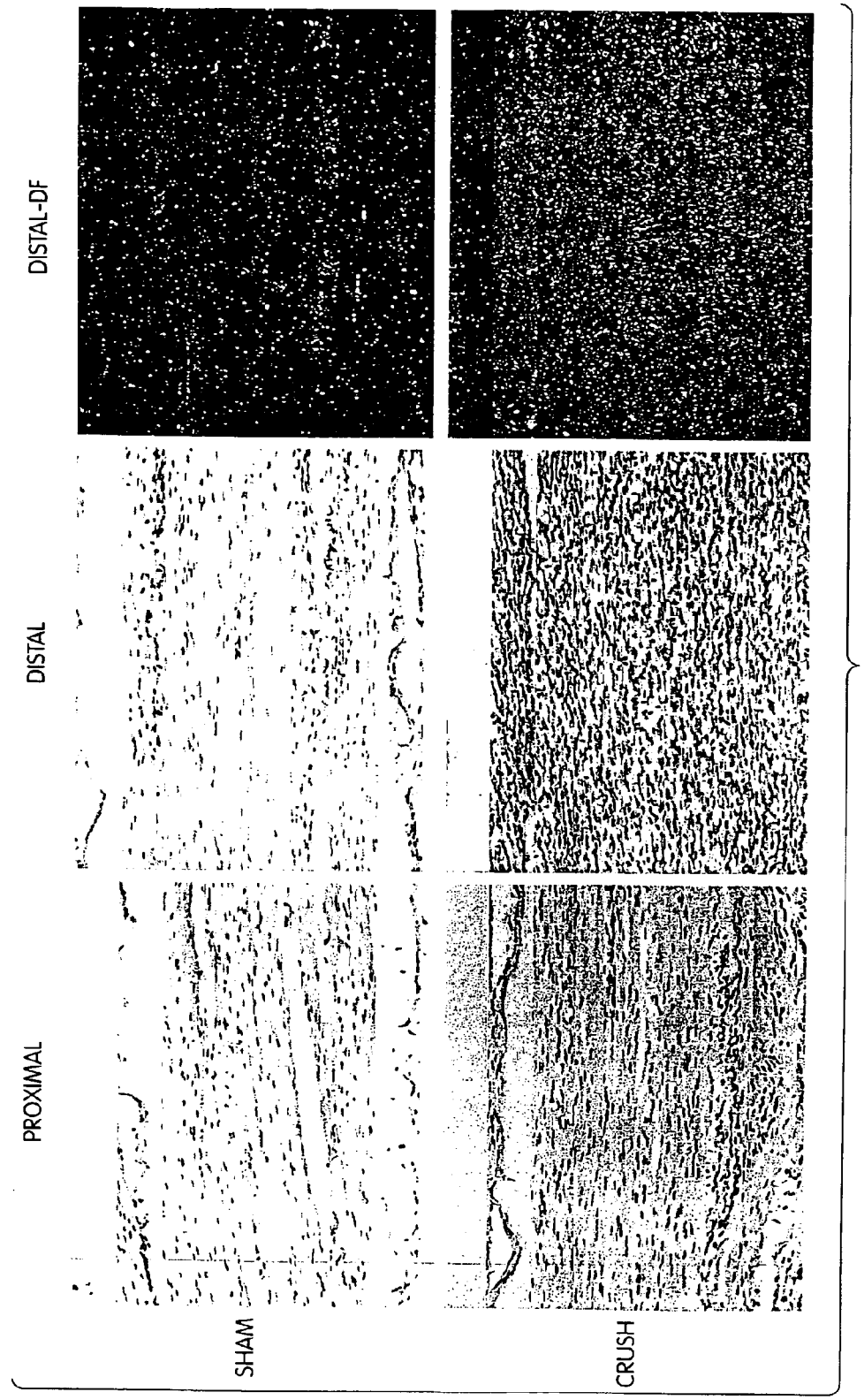

FIG. 31. Hedgehog pathway expression after sciatic nerve crush—Ptc-2 at 13 days

Figure 32:
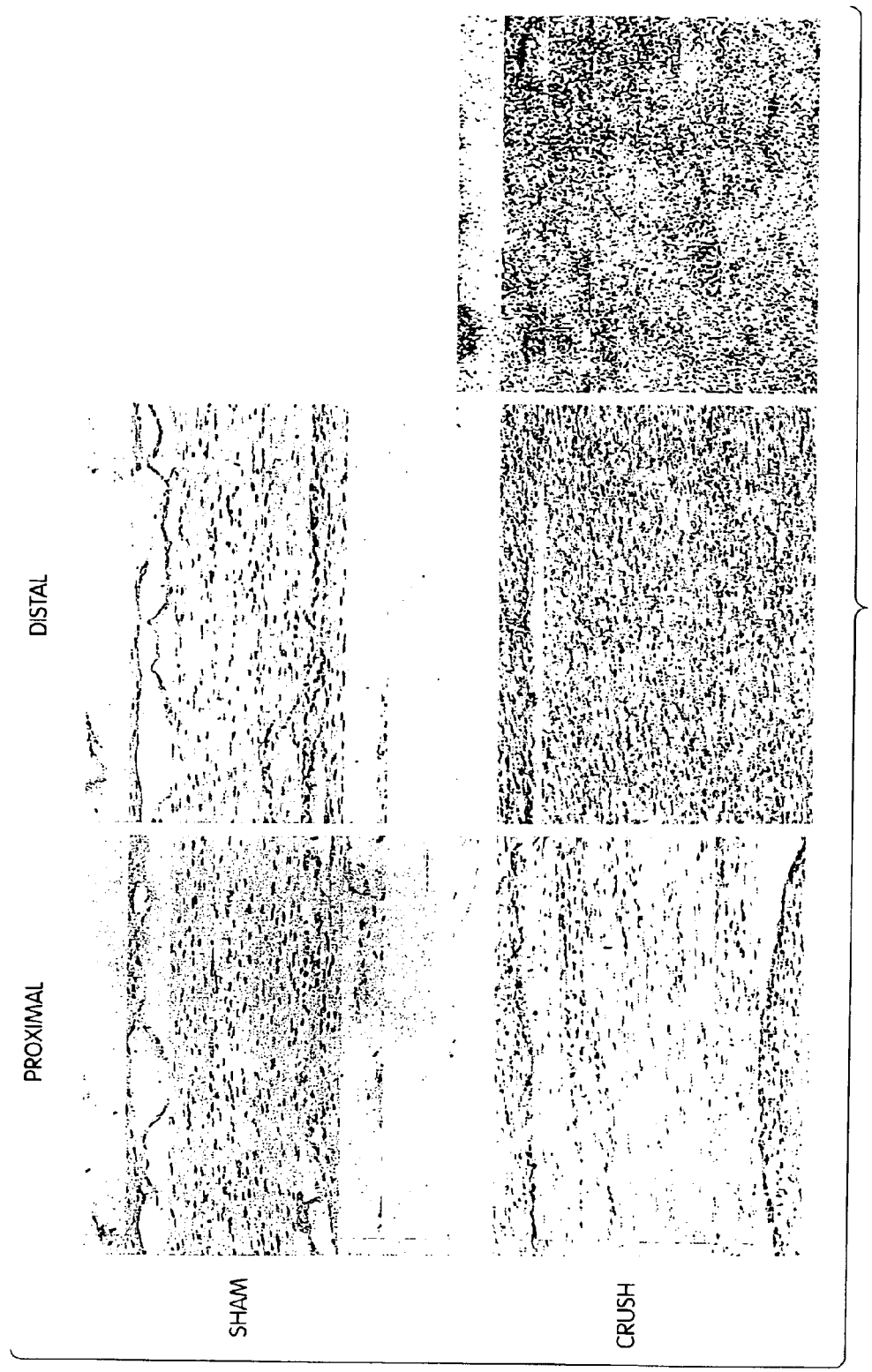

FIG. 32. Hedgehog pathway expression after sciatic nerve crush—Gli-1 at 13 days

DETAILED DESCRIPTION OF THE INVENTION

The Peripheral Nervous System is one of the two main divisions of the body's nervous system. The other is the Central Nervous System, which includes the brain and spinal cord. "Peripheral" means away from the center: and this system contains the nerves that connect the Central Nervous System to the muscles, skin and internal organs.

Peripheral Neuropathy is the term used to describe disorders resulting from injury (e.g., mechanical, chemical, viral, bacterial or genetic) to the peripheral nerves. It can be caused by diseases that affect only the peripheral nerves or by conditions that affect other parts of the body as well. Symptoms almost always involve weakness, numbness or pain—usually in the arms and legs. It will be helpful for you to know a few basics of nerve biology to understand how neuropathy gets started.

I. Overview

The present application is directed to the discovery that hedgehog gene products are able to protect peripheral nerve cells under conditions which otherwise result in peripheral neuropathy. Certain aspects of the invention are directed to preparations of hedgehog polypeptides, or other molecules which regulate patched or smoothened signalling, and their uses as protective agents against both acquired and hereditary neuropathies. As used herein, "peripheral neuropathy" refers to a disorder affecting a segment of the peripheral nervous system. For instance, the method of the present invention can be used as part of a treatment program in the management of neuropathies associated with systemic disease, e.g., viral infections, diabetes, inflamation; as well as genetically acquired (hereditary) neuropathies, e.g., Charcot-Marie-Tooth disease; and neuropathies caused by a toxic agent, e.g., a chemotherapeutic agent such as vincristine; and neuropathies caused by trauma, such as crushed nerves.

To further illustrate, the subject method can be used in the treatment of such acquired neuropathies as diabetic neuropathies; immune-mediated neuropathies such as Guillain-Barre syndrome (GBS) and variants, chronic inflammatory demyelinating polyneuropathy (CIDP), chronic polyneuropathies with antibodies to peripheral nerves, neuropathies associated with vasculitis or inflammation of the blood vessels in peripheral nerve, brachial or lumbosacral plexitis, and neuropathies associated with monoclonal gammopathies; neuropathies associated with tumors or neoplasms such as sensory neuropathy associated with lung cancer, neuropathy associated with multiple myeloma, neuropathy associated with waldenstrom's macroglobulemia, chronic lymphocytic leukemia, or B-cell lymphoma; neuropathy associated with amyloidosis; neuropathies caused by infections; neuropathies caused by nutritional imbalance; neuropathy in kidney disease; hypothyroid neuropathy; neuropathy caused by alcohol and toxins; neuropathies caused by drugs; neuropathy resulting from local irradiation; neuropathies caused by trauma or compression; idiopathic neuropathies Likewise, the subject method can be used in the treatment of such hereditary neuropathies as Charcot-Marie Tooth Disease (CMT); Familial Amyloidotic Neuropathy and other Hereditary Neuropathies; and Hereditary Porphyria.

In another embodiment, the subject method can be used to inhibit or otherwise slow neurodegenerative events associated with age-related neuropathology.

As described in the appended examples, hedgehog proteins are neuroprotective under conditions which promote chemical lesioning of peripheral nerves. Indeed, hedgehog proteins showed a significant protective effective that was similar to the reported effect of NGF. Based upon its neurotrophic and neuroprotective activities, the administration of hedgehog or ptc therapeutics is suggested herein as a treatment for several types of neurodegenerative diseases including neuropathies. In general, the method of the present invention comprises administering to animal, or to cultured peripheral nerves in vitro, an amount of a hedgehog or ptc therapeutic (defined infra) which produces a non-toxic response by the cell of resistance to degeneration, e.g., marked by loss of differentiation, apoptosis and/or necrosis. The subject method can be carried out on cells which may be either dispersed in culture or a part of an intact tissue or organ. Moreover, the method can be performed on cells which are provided in culture (in vitro), or on cells in a whole animal (in vivo).

In one aspect, the present invention provides pharmaceutical preparations and methods for treating or preventing neuropathies utilizing, as an active ingredient, a hedgehog polypeptide or a mimetic thereof The invention also relates to methods of controlling the functional performance of peripheral nerve cells by use of the pharmaceutical preparations of the invention.

The subject hedgehog treatments are effective on both human and animal subjects afflicted with these conditions. Animal subjects to which the invention is applicable extend to both domestic animals and livestock, raised either as pets or for commercial purposes. Examples are dogs, cats, cattle, horses, sheep, hogs and goats.

Without wishing to be bound by any particular theory, the neuroprotective effect of hedgehog treatemtn may be due at least in part to the ability of these proteins to antagonize (directly or indirectly) patched-mediated regulation of gene expression and other physiological effects mediated by that protein. The patched gene product, a cell surface protein, is understood to signal through a pathway which causes transcriptional repression of members of the Wnt and Dpp/BMP families of morphogens, proteins which impart positional information. In development of the CNS and patterning of limbs in vertebrates, the introduction of hedgehog relieves (derepresses) this inhibition conferred by patched, allowing expression of particular gene programs.

Recently, it has been reported that mutations in the human version of patched, a gene first identified in a fruit fly developmental pathway, cause a hereditary skin cancer and may contribute to sporadic skin cancers. See, for example, Hahn et al. (1996) *Cell* 86:841–851; and Johnson et al. (1996) *Science* 272:1668–1671. The demonstraction that nevoid basal-cell carcinoma (NBCC) results from mutations in the human patched gene provided an example of the roles patched plays in post-embryonic deveolpment. These observations have led the art to understand one activity of patched to be a tumor suppressor gene, which may act by inhibiting proliferative signals from hedgehog. Our observations set forth below reveal potential new roles for the hedgehog/patched pathway in maintenance of peripheral nerve cells. Accordingly, the present invention contemplates the use of other agents which are capable of mimicking the effect of the hedgehog protein on patched signalling, e.g., as may be identified from the drug screening assays described below.

In still other embodiments, antagonists of the hedgehog signaling can be used in the selective ablation of sensory neurons, for example, in the treatment of chronic pain syndromes.

II. Definitions

For convience, certain terms employed in the specfication, examples, and appended claims are collected here.

The term "hedgehog therapeutic" refers to various forms of hedgehog polypeptides, as well as peptidomimetics, which can modulate the proliferation/differentiation state of periperhal nerve cells by, as will be clear from the context of individual examples, mimicing or potentiating (agonizing) or inhibiting (antagonizing) the effects of a naturally-occurring hedgehog protein. A hedgehog therapeutic which mimics or potentiates the activity of a wild-type hedgehog protein is a "hedgehog agonist". Conversely, a hedgehog therapeutic which inhibits the activity of a wild-type hedgehog protein is a "hedgehog antagonist".

In particular, the term "hedgehog polypeptide" encompasses preparations of hedgehog proteins and peptidyl fragments thereof, both agonist and antagonist forms as the specific context will make clear.

As used herein the term "bioactive fragment of a hedgehog protein" refers to a fragment of a full-length hedgehog polypeptide, wherein the fragment specifically agonizes or antagonizes inductive events mediated by wild-type hedgehog proteins. The hedgehog biactive fragment preferably is a soluble extracellular portion of a hedgehog protein, where solubility is with reference to physiologically compatible solutions. Exemplary bioactive fragments are described in PCT publications WO 95/18856 and WO 96/17924.

The term "ptc therapeutic" refers to agents which either (i) mimic the effect of hedgehog proteins on patched signalling, e.g., which antagonize the cell-cycle inhibitory activity of patched, or (ii) activate or potentiate patched signalling. In other embodiments, the ptc therapeutic can be a hedgehog antagonist. The ptc therapeutic can be, e.g., a peptide, a nucleic acid, a carbohydrate, a small organic molecule, or natural product extract (or fraction thereof).

An "effective amount" of, e.g., a hedgehog therapeutic, with respect to the subject method of treatment, refers to an amount of, e.g., a hedgehog polypeptide in a preparation which, when applied as part of a desired dosage regimen brings enhances the survival of peripheral nerves, relative to the absence of the hedgehog therapeutic, according to clinically acceptable standards for the disorder to be treated.

A "patient" or "subject" to be treated by the subject method can mean either a human or non-human animal.

The "growth state" of a cell refers to the rate of proliferation of the cell and the state of differentiation of the cell.

"Homology" and "identity" each refer to sequence similarity between two polypeptide sequences, with identity being a more strict comparison. Homology and identity can each be determined by comparing a position in each sequence which may be aligned for purposes of comparison. When a position in the compared sequence is occupied by the same amino acid residue, then the polypeptides can be referred to as identical at that position; when the equivalent site is occupied by the same amino acid (e.g., identical) or a similar amino acid (e.g., similar in steric and/or electronic nature), then the molecules can be refered to as homologous at that position. A percentage of homology or identity between sequences is a function of the number of matching or homologous positions shared by the sequences. An "unrelated" or "non-homologous" sequence shares less than 40 percent identity, though preferably less than 25 percent identity, with an hedgeog sequence of the present invention.

The term "corresponds to", when referring to a particular polypeptide or nucleic acid sequence is meant to indicate that the sequence of interest is identical or homologous to the reference sequence to which it is said to correspond.

The terms "recombinant protein", "heterologous protein" and "exogenous protein" are used interchangeably throughout the specification and refer to a polypeptide which is produced by recombinant DNA techniques, wherein generally, DNA encoding the polypeptide is inserted into a suitable expression construct which is in turn used to transform a host cell to produce the heterologous protein. That is, the polypeptide is expressed from a heterologous nucleic acid.

A "chimeric protein" or "fusion protein" is a fusion of a first amino acid sequence encoding a hedgehog polypeptide with a second amino acid sequence defining a domain foreign to and not substantially homologous with any domain of hh protein. A chimeric protein may present a foreign domain which is found (albeit in a different protein) in an organism which also expresses the first protein, or it may be an "interspecies", "intergenic", etc. fusion of protein structures expressed by different kinds of organisms. In general, a fusion protein can be represented by the general formula $(X)_n$-$(hh)_m$-$(Y)_n$, wherein hh represents all or a portion of the hedgehog protein, X and Y each independently represent an amino acid sequences which are not naturally found as a polypeptide chain contiguous with the hedgehog sequence, m is an integer greater than or equal to 1, and each occurrence of n is, independently, 0 or an integer greater than or equal to 1 (n and m are preferably no greater than 5 or 10).

III. Exemplary Applications of Method and Compositions

The subject method has wide applicability to the treatment or prophylaxis of disorders affecting the regulation of peripheral nerves, including peripheral ganglionic neurons, sympathetic, sensory neurons, and motor neurons. In general, the method can be characterized as including a step of administering to an animal an amount of a ptc or hedgehog therapeutic effective to alter the proliferative and/or differentiation state of treated peripheral nerve cells. Such therapeutic compositions may be useful in treatments designed to rescue, for example, retinal ganglia, inner ear and accoustical nerves, and motomeurons, from lesion-induced death as well as guiding reprojection of these neurons after such damage. Such diseases and conditions include, but are not limited to, chemical or mechanical trauma, infection (such as viral infection with *varicella-zoster*), metabolic disease such as diabetes, nutritional deficiency, toxic agents (such as cisplatin treatment). The goals of treatment in each case can be twofold: (1) to eliminate the cause of the disease and (2) to relieve its symptoms.

Peripheral neuropathy is a condition involving nerve-ending damage in the hands and feet. Peripheral neuropathy generally refers to a disorder that affects the peripheral nerves, most often manifested as one or a combination of motor, sensory, sensorimotor, or autonomic neural dysfunction. The wide variety of morphologies exhibited by peripheral neuropathies can each be uniquely attributed to an equally wide variety of causes. For instance, peripheral neuropathies can be genetically acquired, can result from a systemic disease, or can be induced by a toxic agent. Some toxic agents that cause neurotoxicities are therapeutic drugs, antineoplastic agents, contaminants in foods or medicinals, and environmental and industrial pollutants.

In particular, chemotherapeutic agents known to cause sensory and/or motor neuropathies include vincristine, an antineoplastic drug used to treat haematological malignancies and sarcomas, as well as cisplatin, taxol and others. The neurotoxicity is dose-related, and exhibits as reduced intestinal motility and peripheral neuropathy, especially in the distal muscles of the hands and feet, postural hypotension, and atony of the urinary bladder. Similar problems have been documented with taxol and cisplatin (Mollman, J. E., 1990, New Eng Jour Med. 322:126–127), although cisplatin-related neurotoxicity can be alleviated with nerve growth factor (NGF) (Apfel, S. C. et al, 1992, Annals of Neurology 31:76–80). Although the neurotoxicity is sometimes reversible after removal of the neurotoxic agent, recovery can be a very slow process (Legha, S., 1986, Medical Toxicology 1:421–427; Olesen, et al., 1991, Drug Safety 6:302–314).

There are a number of inherited peripheral neuropathies, including: Refsum's disease, Abetalipoproteinemia, Tangier disease, Krabbe's disease, Metachromatic leukodystrophy, Fabry's disease, Dejerine-Sottas syndrome, and others. Of all the inherited neuropathies, the most common by far is Charcot-Marie-Tooth Disease.

Charcot-Marie-Tooth (CMT) Disease (also known as Peroneal Muscular Atrophy, or Hereditary Motor Sensory Neuropathy (HMSN)) is the most common hereditary neurological disorder. It is characterized by weakness and atrophy, primarily of the peroneal muscles, due to segmental demyclination of peripheral nerves and associated degeneration of axons and anterior horn cells. Autosomal dominant inheritance is usual, and associated degenerative CNS disorders, such as Friedreich's ataxia, are common.

In one aspect, the method of the present invention can be used in the treatment and maintenance of hereditary neuropathies. This group of neuropathies are now becoming increasingly recognized due to the dramatic advances in molecular genetics. The symptoms of the various hereditary neuropathies are wide ranging. A common denominator is usually the early onset of mild numbness and tingling in the feet that slowly progresses to involve the legs and the hands and later the rest of the upper extremities. Most of the hereditary neuropathies do have a motor component consisting of distal weakness in the lower and upper extremities. A majority of patients with hereditary neuropathies have high arches in their feet or other bony deformities. The symptoms are very slowly progressive and the majority of the patients are still walking two decades after the onset of their symptoms.

The diagnosis of a hereditary neuropathy is usually suggested with the early onset of neuropathic symptoms, especially when a positive family history is also present. Prior to the recent genetic advances, the diagnosis was supported by typical findings of marked slowing of the nerve conduction studies on electromyography and a nerve biopsy. Typical findings on a nerve biopsy include the presence of so-called onion-bulbs, indicating a recurring demyelinating and remyelinating of the nerve fibers. With the most recent genetic advances, two major hereditary neuropathies known as "Charcot-Marie-Tooth disease" and "hereditary neuropathy with liability to pressure palsies" can be diagnosed with a simple blood test that identifies the different mutations responsible for these two entities.

Hereditary neuropathies are caused by genetic abnormalities which are transmitted from generation to generation. For several of these, the genetic defect is known, and tests are available for diagnosis and prenatal counseling.

As set foth above, the subject method can be used as part of a therapeutic regimen in the treatment of Charcot-Marie Tooth Disease (CMT). This is a general term given to the hereditary sensorimotor neuropathies. CMT type 1 (CMT 1) is associated with demyelination or breakdown of the myelin sheaths. Several different abnormalities have been identified. CMT Type 1A is most commonly caused by duplication of a gene encoding a myelin protein called PMP-22, and CMT type 1B is caused by a mutation in a myelin protein called the Po glycoprotein. CMTX is a hereditary sensorimotor neuropathy which affects only men. It is caused by a mutation in a gene encoding a protein called Connexin 32 on the X-chromosome.

In certain embodiments, the subject method can be used to treat, or at least reduce the severity of, Amyotrophic lateral sclerosis (ALS). According the subject invention, a trophic amount of a hedgehog or ptc therapeutic can be administered to an animal suffering from, or at risk of developing, ALS.

In another embodiment, the subject method can be used in the treatment of Familial Amyloidotic Neuropathy and other related hereditary neuropathies. Amyloidotic neuropathy usually presents with pain, sensory loss and autonomic dysfunction. It is caused by a mutation in a protein called Transthyretin, resulting in deposition of the protein as amyloid in the peripheral nerves.

The subject method can be used in the treatment of hereditary porphyria, which can have components of peripheral neuropathy.

Still another hereditary neuropathy for which the subject methods can be used for treatment is hereditary sensory neuropathy Type II (HSN II).

The methods and compositions of the present invetion can also be used in the treatment and maintenance of acquired neuropathies.

For example, hedgehog and ptc therapeutics can be used to prevent diabetic neuropathies. Diabetes is the most common known cause of neuropathy. It produces symptoms in approximately 10% of people with diabetes. In most cases, the neuropathy is predominantly sensory, with pain and sensory loss in the hands and feet. But some diabetics have mononeuritis or mononeuritis multiplex which causes weakness in one or more nerves, or lumbosacral plexopathy or amyotrophy which causes weakness in the legs.

The instant method can also be used in the treatment of immune-mediated neuropathies. The main function of the immune system is to protect the body against infectious organisms which enter from outside. In some cases, however the immune system turns against the body and causes autoimmune disease. The immune system consists of several types of white blood cells, including T-lymphocytes, which also regulate the immune response; and B-lymphocytes or plasma cells, which secrete specialized proteins called "antibodies" Sometimes, for unknown reasons, the immune system mistakenly attacks parts of the body such as the peripheral nenes. This is "autoimmune" Peripheral Neuropathy. There are several different types, depending on the part of the peripheral nerve which is attacked and the type ofthe immune reaction. The following are brief descriptions of the neuropathies which are mediated by the immune system.

For instance, a hedgehog or ptc therapeutic can be used to treat Guillain-Barre Syndrome (GBS). An acute neuropathy because it comes on suddenly or rapidly. Guillain-Barre Syndrome can progress to paralysis and respiratory failure within days or weeks. after onset. The neuropathy is caused when the immune system destroys the myelin sheaths of the motor and sensory nerves. It is often preceded by infection, vaccination or trauma, and that is thought to be what triggers the autoimmune reaction. The disease is self-limiting, with spontaneous recovery within six to eight weeks. But the recovery is often incomplete.

Other neuropathies which begin acutely, and which can be treated by the method of the present invention, include Acute Motor Neuropathy, Acute Sensory Neuropathy, and Acute Autonomic Neuropathy, in which there is an immune attack against the motor, sensory or autonomic nerves, respectively. The Miller-Fisher Syndrome is another variant in which there is paralysis of eye gaze, incoordination, and unsteady gait.

Still another acquired neuropathy which is may be treated by the subject method is Chronic Inflammatory Demyelinating Polyneuropathy (CIDP). CIDP is thought to be a chronic and more indolent form of the Guillain-Barre Syndrome. The disease progresses either with repeated attacks, called relapses, or in a stepwise or steady fashion. As in GBS, there appears to be destruction of the myelin sheath by antibodies and T-lymphocytes. But since there is no specific test for CIDP, the diagnosis is based on the clinical and laboratory characteristics.

Chronic Polyneuropathies with antibodies to peripheral nerves is still another peripheral neuropathy for which the subject methods can be employed to treat or prevent. In some types of chronic neuropathies, antibodies to specific components of nerve have been identified. These include demyelinating neuropathy associated with antibodies to the Myelin Associated Glycoprotein (MAG), motor neuropathy associated with antibodies to the gangliosides GM1b or GD1a, and sensory neuropathy associated with anti-sulfatide or GD1b ganglioside antibodies. The antibodies in these cases bind to oligosaccharide or sugar like molecules, which are linked to proteins (glycoproteins) or lipids (glycolipids or gangliosides) in the nerves. It is suspected that these antibodies may be responsible for the neuropathies.

The subject method can also be used as part of a therapeutic plan for treating neuropathies associated with vasculitis or inflammation of the blood vessels in peripheral nerves. Neuropathy can also be caused by Vasculitis—an inflammation of the blood vessels in peripheral nerve. It produces small "strokes" along the course of the peripheral nerves, and may be restricted to the nerves or it may be generalized, include a skin rash, or involve other organs. Several rheumatological diseases like Rheumatoid Arthritis, Lupus, Periarteritis Nodosa, or Sjogren's Syndrome, are associated with generalized Vasculitis, which can also involve the peripheral nerves. Vasculitis can cause Polyneuritis, Mononeuritis, or Mononeuritis Multiplex, depending on the distribution and severity of the lesions.

In still another embodiment, the method of the present invention can be used for treatment of brachial or lumbosacral plexitis. The brachial plexus, which lies under the armpit, contains the nerves to the arm and hand. Brachial Plexitis is the result of inflamation of that nerve bundle, and produces weakness and pain in one or both arms. Lumbosacral Plexitis, which occurs in the pelvis, causes weakness and pain in the legs.

Hedgehog and ptc therapeutics mayu also be suitable for use in the treatment of neuropathies associated with monoclonal gammopathies. In Monoclonal Gammopathy, single clones of B-cells or plasma cells in the bone marrow or Iymphoid organs expand to form benign or malignant tumors and secrete antibodies. "Monoclonal" is because there are single clones of antibodies. And "Gammopathy" stands for gammaglobulins, which is another name for antibodies. In some cases, the antibodies react with nerve components; in others, fragments of the antibodies form amyloid deposits.

Yet another aspect of the present invention relates to the use of the subject method in the treatment of neuropathies associated with tumors or neoplasms. Neuropathy can be due to direct infiltration of nerves by tumor cells or to indirect effect of the tumor. The latter is called Paraneoplastic Neuropathy. Several types have been described. For instance, the subject methods can be used to manage sensory neuropathy associated with lung cancer. This neuropathy is associated with antibodies to a protein called Hu, which is present in the sensory neurons of the peripheral nerves. Likewise, the subject method can be used to treat neuropathies associated with multiple myeloma. Multiple myeloma is a bony tumor which is caused by antibody-secreting plasma cells in the bone marrow. The tumor is made up of a single clone of plasma cells, and the antibodies they produce are identical or monoclonal. Some people with multiple myeloma develop a Sensorimotor Polyneuropathy with degeneration of axons in the peripheral nerves. In other embodiments, the subject method can be used to treat neuropathies associated with Waldenstrom's Macroglobulemia, Chronic Lymphocytic Leukemia, or B-cell Lymphoma. These are tumors caused by antibody-secreting B-lymphocytes in the spleen, bone marrow or lymph nodes. These antibodies are monoclonal and frequently react with peripheral nerve components such as MAG, GM1, or sulfatide. In still other embodiments, the the hedgehog and ptc therapeutics of the present invention can be used as part of therapeutic protocol for the treatment of patients with cancers where neuropathy is a consequence of local irradiation or be caused by medications such as vincristine and cisplatinum.

The present invention also contemplates the use of hedgehog and ptc therapeutics for the treatment of neuropathies associated with amyloidosis. Amyloid is a substance which is deposited in the peripheral nerves and interferes with their operation: the disorder is Amyloidosis. There are two main types: Primary Amyloidosis, in which the deposits contain fragments of monoclonal antibodies (see the Monoclonal Gammopathy paragraph above); and Hereditary Amyloidosis in which the deposits contain a mutated protein called Transthyretin. Primary Amyloidosis is usually associated with Monoclonal Gammopathies or myeloma (See above.)

Still another aspect of the present invention provides the subject method as a means for treating neuropathies caused by infections. Peripheral neuropathies can be caused by infection of the peripheral nerves. Viruses that cause peripheral neuropathies include the AIDS virus, HIV-I, which causes slowly progressive sensory neuropathy, Cytomegalo virus which causes a rapidly progressive paralytic neuropathy, Herpes Zoster which cause Shingles, and Poliovirus which causes a motor neuropathy. Hepatitis B or C infections are sometimes associated with vasculitic neuropathy.

Bacterial infections that cause neuropathy include Leprosy which causes a patchy sensory neuropathy, and Diphtheria which can cause a rapidly progressive paralytic neuropathy. Other infectious diseases that cause neuropathy include Lyme disease which is caused by a spirochete, and Trypanosomiasis which is caused by a parasite. Both commonly present with a multifocal neuropathy Neuropathies caused by nutritional imbalance are also candidate disorders for treatment by the subject method. Deficiencies of Vitamins B12, B1 (thiamine), B6 (pyridoxine), or E, for example, can produce polyneuropathies with degeneration of peripheral nerve axons. This can be due to poor diet, or inability to absorb the nutrients from the stomach or gut.

Moreoverm megadoses of Vitamin B6 can also cause a peripheral neuropathy, and the subject method can be used as part of a de-toxification program in such cases.

Yet another use of the subject method is in the treatment of neuropathies arising in kidney diseases. Chronic renal failure can cause a predominantly sensory peripheral neuropathy with degeneration of peripheral nerve axons.

Another aspect of the present invention provides a method for treating hypothyroid neuropathies. Hypothyroidism is sometimes associated with a painful sensory polyneuropathy with axonal degeneration. Mononeuropathy or Mononeuropathy Multiplex can also occur due to compression of the peripheral nerves by swollen tissues.

The subject method can also be used in the treatment of neuropathies caused by Alcohol and Toxins. Certain toxins can cause Peripheral Neuropathy. Lead toxicity is associated with a motor neuropathy; arsenic or mercury cause a sensory neuropathy, Thalium can cause a sensory and autonomic neuropathy. several of the organic solvents and insecticides can also cause polyneuropathy. Alcohol is directly toxic to nerves and alcohol abuse is a major cause of neuropathy. The subject method can be used, in certain embodiments, as part of a broader detoxification program.

In still another embodiment, the methods and compositions of the present invention can be used for the treatment of neuropathies caused by drugs. Several drugs are known to cause neuropathy. They include, among others, vincristine and cisplatinum in cancer, nitrofurantoin, which is used in pyelonephritis, amiodarone in cardiac arrhythmias, disulfiram in alcoholism, ddC and ddI in AIDS, and dapsone which is used to treat Leprosy. As above, the subject method can be used, in certain embodiments, as part of a broader detoxification program.

The method of the present invention can also be used in the treatment of neuropathies caused by trauma or compression. Localized neuropathies can result from compression of nerves by external pressure or overlying tendons and other tissues. The best known of these are the Carpal Tunnel Syndrome which results from compression at the wrist, and cervical or lumbar radiculopathies (Sciatica) which result from compression of nerve roots as they exit the spine. Other common areas of nerve compression include the elbows, armpits, and the back of the knees.

The subject method is also useful in variety of idiopathic neuropathies. The term "idiopathic" is used whenever the cause of the neuropathy cannot be found. In these cases, the neuropathy is classified according to its manifestations, i.e., sensory, motor, or sensorimotor idiopathic polyneuropathy.

Another aspect of the invention provides a conjoint therapy wherein one or more other therapeutic agents are administered with the hedgehog or ptc therapeutic agent. Such conjoint treatment may be achieved by way of the simultaneous, sequential or separate dosing of the individual components of the treatment. For example, the subject method can be carried out conjointly with other neuroprotective agents. The dosages recited herein would be adjusted to compensate for such additional components in the therapeutic composition. Progress of the treated patient can be monitored by conventional methods.

IV Exemplary Hedgehog Therapeutic Compounds.

The hedgehog therapeutic compositions of the subject method can be generated by any of a variety of techniques, including purification of naturally occurring proteins, recombinantly produced proteins and synthetic chemistry. Polypeptide forms of the hedgehog therapeutics are preferably derived from vertebrate hedgehog proteins, e.g., have sequences corresponding to naturally occurring hedgehog proteins, or fragments thereof, from vertebrate organisms. However, it will be appreciated that the hedgehog polypeptide can correspond to a hedgehog protein (or fragment thereof) which occurs in any metazoan organism.

The various naturally-occurring hedgehog proteins from which the subject therapeutics can be derived are characterized by a signal peptide, a highly conserved N-terminal region, and a more divergent C-terminal domain. In addition to signal sequence cleavage in the secretory pathway (Lee, J. J. et al (1992) Cell 71:33–50; Tabata, T. et al. (1992) Genes Dev. 2635–2645; Chang, D. E. et al. (1994) Development 120:3339–3353), hedgehog precursor proteins naturally undergo an internal autoproteolytic cleavage which depends on conserved sequences in the C-terminal portion (Lee et al (1994) Science 266:1528–1537; Porter et al. (1995) Nature 374:363–366). This autocleavage leads to a 19 kD N-terminal peptide and a C-terminal peptide of 26–28 kD (Lee et al. (1992) supra; Tabata et al (1992) supra; Chang et al. (1994) Supra; Lee et al. (1994) supra; Bumcrot, D. A., et al. (1995) Mol. Cell. Biol. 15:2294–2303; Porter et al. (1995) supra; Ekker, S. C. et al (1995) Curr. Biol. 5:944–955; Lai, C. J. et al. (1995) Development 121:2349–2360). The N-terminal peptide stays tightly associated with the surface of cells in which it was synthesized, while the C-terminal peptide is freely diffusible both in vitro and in vivo (Lee et al. (1994) supra; Bumcrot et al. (1995) supra; Mart', E. et al. (1995) Development 121:2537–2547; Roelink, H. et al (1995) Cell 81:445–455). Cell surface retention of the N-terminal peptide is dependent on autocleavage, as a truncated form of hedgehog encoded by an RNA which terminates precisely at the normal position of internal cleavage is diffusible in vitro (Porter et al. (1995) supra) and in vivo (Porter, J. A. et al. (1996) Cell 86, 21–34). Biochemical studies have shown that the autoproteolytic cleavage of the hedgehog precursor protein proceeds through an internal thioester intermediate which subsequently is cleaved in a nucleophilic substitution. It is suggested that the nucleophile is a small lipophilic molecule, more particularly cholesterol, which becomes covalently bound to the C-terminal end of the N-peptide (Porter et al. (1996) supra), tethering it to the cell surface.

The vertebrate family of hedgehog genes includes at least four members, e.g., paralogs of the single drosophila hedgehog gene (SEQ ID No. 19). Three of these members, herein referred to as Desert hedgehog (Dhh), Sonic hedgehog (Shh) and Indian hedgehog (Ihh), apparently exist in all vertebrates, including fish, birds, and mammals. A fourth member, herein referred to as tiggie-winkle hedgehog (Thh), appears specific to fish. According to the appended sequence listing, (see also Table 1) a chicken Shh polypeptide is encoded by SEQ ID No:1; a mouse Dhh polypeptide is encoded by SEQ ID No:2; a mouse Ihh polypeptide is encoded by SEQ ID No:3; a mouse Shh polypeptide is encoded by SEQ ID No:4 a zebrafish Shh polypeptide is encoded by SEQ ID No:5; a human Shh polypeptide is encoded by SEQ ID No:6; a human Ihh polypeptide is encoded by SEQ ID No:7; a human Dhh polypeptide is encoded by SEQ ID No. 8; and a zebrafish Thh is encoded by SEQ ID No. 9.

TABLE 1

Guide to hedgehog sequences in Sequence Listing

| | Nucleotide | Amino Acid |
|---|---|---|
| Chicken Shh | SEQ ID No. 1 | SEQ ID No. 10 |
| Mouse Dhh | SEQ ID No. 2 | SEQ ID No. 11 |
| Mouse Ihh | SEQ ID No. 3 | SEQ ID No. 12 |
| Mouse Shh | SEQ ID No. 4 | SEQ ID No. 13 |
| Zebrafish Shh | SEQ ID No. 5 | SEQ ID No. 14 |
| Human Shh | SEQ ID No. 6 | SEQ ID No. 15 |
| Human Ihh | SEQ ID No. 7 | SEQ ID No. 16 |
| Human Dhh | SEQ ID No. 8 | SEQ ID No. 17 |
| Zebrafish Thh | SEQ ID No. 9 | SEQ ID No. 18 |
| Drosophila HH | SEQ ID No. 19 | SEQ ID No. 20 |

In addition to the sequence variation between the various hedgehog homologs, the hedgehog proteins are apparently present naturally in a number of different forms, including a pro-form, a full-length mature form, and several processed fragments thereof. The pro-form includes an N-terminal signal peptide for directed secretion of the extracellular domain, while the full-length mature form lacks this signal sequence.

As described above, further processing of the mature form occurs in some instances to yield biologically active fragments of the protein. For instance, sonic hedgehog undergoes additional proteolytic processing to yield two peptides of approximately 19 kDa and 27 kDa, the 19 kDa fragment corresponding to an proteolytic N-terminal portion of the mature protein.

In addition to proteolytic fragmentation, the vertebrate hedgehog proteins can also be modified post-translationally, such as by glycosylation and/or addition of lipophilic moieties, such as stents, fatty acids, etc., though bacterially produced (e.g. unmodified) forms of the proteins still maintain certain of the bioactivities of the native protein. Bioactive fragments of hedgehog polypeptides of the present invention have been generated and are described in great detail in, e.g., PCT publications WO 95/18856 and WO 96/17924.

There are a wide range of lipophilic moieties with which hedgehog polypeptides can be derivatived. The term "lipophilic group", in the context of being attached to a hedgehog polypeptide, refers to a group having high hydrocarbon content thereby giving the group high affinity to lipid phases. A lipophilic group can be, for example, a relatively long chain alkyl or cycloalkyl (preferably n-alkyl) group having approximately 7 to 30 carbons. The alkyl group may terminate with a hydroxy or primary amine "tail". To further illustrate, lipophilic molecules include naturally-occurring and synthetic aromatic and non-aromatic moieties such as fatty acids, sterols, esters and alcohols, other lipid molecules, cage structures such as adamantane and buckninsterfullerenes, and aromatic hydrocarbons such as benzene, perylene, phenanthrene, anthracene, naphthalene, pyrene, chrysene, and naphthacene.

In one embodiment, the hedgehog polypeptide is modified with one or more sterol moieties, such as cholesterol. See, for example, PCT publication WO 96/17924. In certain embodiments, the cholesterol is preferably added to the C-terminal glycine were the hedgehog polypeptide corresponds to the naturally-occurring N-terminal proteolytic fragment.

In another embodiment, the hedgehog polypeptide can be modified with a fatty acid moiety, such as a myrostoyl, palmitoyl, stearoyl, or arachidoyl moiety. See, e.g., Pepinsky et al. (1998) *J Biol. Chem* 273: 14037.

In addition to those effects seen by cholesterol-addition to the C-terminus or fatty acid addition to the N-terminus of extracellular fragments of the protein, at least certain of the biological activities of the hedgehog gene products are unexpectedly potentiated by derivativation of the protein with lipophilic moieties at other sites on the protein and/or by moieties other than cholesterol or fatty acids. Certain aspects of the invention are directed to the use of preparations of hedgehog polypeptides which are modified at sites other than N-terminal or C-terminal residues of the natural processed form of the protein, and/or which are modified at such terminal residues with lipophilic moieties other than a sterol at the C-terminus or fatty acid at the N-terminus.

Particularly useful as lipophilic molecules are alicyclic hydrocarbons, saturated and unsaturated fatty acids and other lipid and phospholipid moieties, waxes, cholesterol, isoprenoids, terpenes and polyalicyclic hydrocarbons including adamantane and buckminsterfillerenes, vitamins, polyethylene glycol or oligoethylene glycol, (C1–C18)-alkyl phosphate diesters, —O—$CH_2$—CH(OH)—O—(C12–C18)-alkyl, and in particular conjugates with pyrene derivatives. The lipophilic moiety can be a lipophilic dye suitable for use in the invention include, but are not limited to, diphenylhexatriene, Nile Red, N-phenyl-1-naphthylamine, Prodan, Laurodan, Pyrene, Perylene, rhodamine, rhodamine B, tetramethylrhodamine, Texas Red, sulforhodamine, 1,1'-didodecyl-3,3,3', 3'tetramethylindocarbocyanine perchlorate, octadecyl rhodamine B and the BODIPY dyes available from Molecular Probes Inc.

Other exemplary lipophilic moietites include aliphatic carbonyl radical groups include 1- or 2-adamantylacetyl, 3-methyladamant-1-ylacetyl, 3-methyl-3-bromo-1-adamantylacetyl, 1-decalinacetyl, camphoracetyl, camphaneacetyl, noradamantylacetyl, norbomancacetyl, bicyclo[2.2.2.]-oct-5-eneacetyl, 1-methoxybicyclo[2.2.2.]-oct-5-ene-2-carbonyl, cis-5-norbomene-endo-2,3-dicarbonyl, 5-norbomen-2-ylacetyl, (IR)-(−)-myrtentaneacetyl, 2-norbomaneacetyl, anti-3-oxo-tricyclo [2.2.1.0<2,6>]-heptane-7-carbonyl, decanoyl, dodecanoyl, dodecenoyl, tetradecadienoyl, decynoyl or dodecynoyl.

The hedgehog polypeptide can be linked to the hydrophobic moiety in a number of ways including by chemical coupling means, or by genetic engineering.

There are a large number of chemical cross-linking agents that are known to those skilled in the art. For the present invention, the preferred cross-linking agents are heterobifimctional cross-linkers, which can be used to link the hedgehog polypeptide and hydrophobic moiety in a stepwise manner. Heterobifunctional cross-linkers provide the ability to design more specific coupling methods for conjugating to proteins, thereby reducing the occurrences of unwanted side reactions such as homo-protein polymers. A wide variety of heterobifunctional cross-linkers are known in the art. These include: succinimidyl 4-(N-maleimidomethyl) cyclohexane-1-carboxylate (SMCC), m-Maleimidobenzoyl-N-hydroxysuccinimide ester (MBS); N-succinimidyl (4-iodoacetyl) aminobenzoate (SIAB), succinimidyl 4-(p-maleimidophenyl) butyrate (SMPB), 1-ethyl-3-(3-dimethylaminopropyl) carbodiimide hydrochloride (EDC); 4-succinimidyloxycarbonyl-a-methyl-a-(2-pyridyldithio)-tolune (SMPT), N-succinimidyl 3-(2-pyridyldithio) propionate (SPDP), succinimidyl 6-[3-(2-pyridyldithio) propionate] hexanoate (LC-SPDP). Those cross-linking agents having N-hydroxysuccinimide moieties can be obtained as the N-hydroxysulfosuccinimide analogs, which generally have greater water solubility. In addition, those cross-linking agents having disulfide bridges within the linking chain can be synthesized instead as the alkyl derivatives so as to reduce the amount of linker cleavage in vivo.

In addition to the heterobifunctional cross-linkers, there exists a number of other cross-linking agents including homobifunctional and photoreactive cross-linkers. Disuccinimidyl suberate (DSS), bismaleimidohexane (BMH) and dimethylpimelimidate-2 HCl (DMP) are examples of useful homobifunctional cross-linking agents, and bis-[β-(4-azidosalicylamido)ethyl]disulfide (BASED) and N-succinimidyl-6(4'-azido-2'-nitrophenyl-amino)hexanoate (SANPAH) are examples of useful photoreactive cross-linkers for use in this invention. For a recent review of protein coupling techniques, see Means et al. (1990) *Bioconjugate Chemistry* 1:2–12, incorporated by reference herein.

One particularly useful class of heterobifunctional cross-linkers, included above, contain the primary amine reactive group, N-hydroxysuccinimide (NHS), or its water soluble analog N-hydroxysulfosuccinimide (sulfo-NHS). Primary amines (lysine epsilon groups) at alkaline pH's are unprotonated and react by nucleophilic attack on NHS or sulfo-NHS esters. This reaction results in the formation of an amide bond, and-release of NHS or sulfo-NHS as a by-product.

Another reactive group useful as part of a heterobifunctional cross-linker is a thiol reactive group. Common thiol reactive groups include maleimides, halogens, and pyridyl disulfides. Maleimides react specifically with free sulfhydryls (cysteine residues) in minutes, under slightly acidic to neutral (pH 6.5–7.5) conditions. Halogens (iodoacetyl functions) react with —SH groups at physiological pH's. Both of these reactive groups result in the formation of stable thioether bonds.

The third component of the heterobifunctional cross-linker is the spacer arm or bridge. The bridge is the structure that connects the two reactive ends. The most apparent attribute of the bridge is its effect on steric hindrance. In some instances, a longer bridge can more easily span the distance necessary to link two complex biomolecules. For instance, SMPB has a span of 14.5 angstroms.

Preparing protein-protein conjugates using heterobifunctional reagents is a two-step process involving the amine reaction and the sulfhydryl reaction. For the first step, the amine reaction, the protein chosen should contain a primary amine. This can be lysine epsilon amines or a primary alpha amine found at the N-terminus of most proteins. The protein should not contain free sulfhydryl groups. In cases where both proteins to be conjugated contain free sulfhydryl groups, one protein can be modified so that all sulfhydryls are blocked using for instance, N-ethylmaleimide (see Partis et al. (1983) J. Pro. Chem. 2:263, incorporated by reference herein). Ellman's Reagent can be used to calculate the quantity of sulfhydryls in a particular protein (see for example Ellman et al. (1958) Arch. Biochem. Biophys. 74:443 and Riddles et al. (1979) Anal. Biochem. 94:75, incorporated by reference herein).

The reaction buffer should be free of extraneous amines and sulfhydryls. The pH of the reaction buffer should be 7.0–7.5. This pH range prevents maleimide groups from reacting with amines, preserving the maleimide group for the second reaction with sulfhydryls.

The NHS-ester containing cross-linkers have limited water solubility. They should be dissolved in a minimal amount of organic solvent (DMF or DMSO) before introducing the cross-linker into the reaction mixture. The cross-linker/solvent forms an emulsion which will allow the reaction to occur.

The sulfo-NHS ester analogs are more water soluble, and can be added directly to the reaction buffer. Buffers of high ionic strength should be avoided, as they have a tendency to "salt out" the sulfo-NHS esters. To avoid loss of reactivity due to hydrolysis, the cross-linker is added to the reaction mixture immediately after dissolving the protein solution.

The reactions can be more efficient in concentrated protein solutions. The more alkaline the pH of the reaction mixture, the faster the rate of reaction. The rate of hydrolysis of the NHS and sulfo-NHS esters will also increase with increasing pH. Higher temperatures will increase the reaction rates for both hydrolysis and acylation.

Once the reaction is completed, the first protein is now activated, with a sulfhydryl reactive moiety. The activated protein may be isolated from the reaction mixture by simple gel filtration or dialysis. To carry out the second step of the cross-linking, the sulfhydryl reaction, the lipophilic group chosen for reaction with maleimides, activated halogens, or pyridyl disulfides must contain a free sulfhydryl. Alternatively, a primary amine may be modified with to add a sulfhydryl In all cases, the buffer should be degassed to prevent oxidation of sulfhydryl groups. EDTA may be added to chelate any oxidizing metals that may be present in the buffer. Buffers should be free of any sulfhydryl containing compounds.

Maleimides react specifically with —SH groups at slightly acidic to neutral pH ranges (6.5–7.5). A neutral pH is sufficient for reactions involving halogens and pyridyl disulfides. Under these conditions, maleimides generally react with —SH groups within a matter of minutes. Longer reaction times are required for halogens and pyridyl disulfides.

The first sulfhydryl reactive-protein prepared in the amine reaction step is mixed with the sulfhydryl-containing lipophilic group under the appropriate buffer conditions. The conjugates can be isolated from the reaction mixture by methods such as gel filtration or by dialysis.

Exemplary activated lipophilic moieties for conjugation include: N-(1-pyrene)maleimide; 2,5-dimethoxystilbene-4'-maleimide, eosin-5-maleimide; fluorescein-5-maleimide; N-(4-(6-dimethylamino-2-benzofiranyl)phenyl)maleimide; benzophenone-4-maleimide; 4-dimethylaminophenylazophenyl-4'-maleimide (DABMI), tetramethylrhodamine-5-maleimide, tetramethylrhodamine-6-maleimide, Rhodamine Red™ C2 maleimide, N-(5-aminopentyl)maleimide, trifluoroacetic acid salt, N-(2-aminoethyl)maleimide, trifluoroacetic acid salt, Oregon Green™ 488 maleimide, N-(2-((2-(((4-azido-2,3,5,6-tetrafluoro)benzoyl)amino)ethyl)dithio)ethyl)maleimide (TFPAM-SS1 ), 2-(1-(3-dimethylaminopropyl)-indol-3-yl)-3-(indol-3-yl) maleimide (bisindolylmaleimide; GF 109203X), BODIPY® FL N-(2-aminoethyl)maleimide, N-(7-dimethylamino-4-methylcoumarin-3-yl)maleimide (DACM), Alexa™ 488 C5 maleimide, Alexa™ 594 C5 maleimide, sodium saltN-(1-pyrene)maleimide, 2,5-dimethoxystilbene-4'-maleimide, eosin-5-maleimide, fluorescein-5-maleimide, N-(4-(6-dimethylamino-2-benzofuranyl)phenyl)maleimide, benzophenone-4-maleimide, 4-dimethylaminophenylazophenyl-4'-maleimide, 1-(2-maleimidylethyl)-4-(5-(4-methoxyphenyl)oxazol-2-yl)pyridinium methanesulfonate, tetramethykhodamine-5-maleimide, tetramethylrhodamine-6-maleimide, Rhodamine Red™ C2 maleimide, N-(5-aminopentyl)maleimide, N-(2-aminoethyl)maleimide, N-(2-((2-(((4-azido-2,3,5,6-tetrafluoro)benzoyl)amino)ethyl) dithio)ethyl)maleimide, 2-(1-(3-dimethylaminopropyl)-indol-3-yl)-3-(indol-3-yl)maleimide, N-(7-dimethylamino-4-methylcoumarin-3-yl)maleimide (DACM), 11H-Benzo[a] fluorene, Benzo[a]pyrene.

In one embodiment, the hedgehog polypeptide can be derivatived using pyrene maleimide, which can be purchased from Molecular Probes (Eugene, Oreg.), e.g., N-(1-pyrene)maleimide or 1-pyrenemethyl iodoacetate (PMIA ester).

For those embodiments wherein the hydophobic moiety is a polypeptide, the modified hedgehog polypeptide of this invention can be constructed as a fusion protein, containing the hedgehog polypeptide and the hydrophobic moiety as one contiguous polypeptide chain.

In certain embodiments, the lipophilic moiety is an amphipathic polypeptide, such as magainin, cecropin, attacin, melittin, gramicidin S, alpha-toxin of Staph. aureus, alamethicin or a synthetic amphipathic polypeptide. Fusogenic coat proteins from viral particles can also be a convenient source of amphipathic sequences for the subject hedgehog proteins.

In other embodiments, we can exploit the advantages of a hedgehog/immunoglobulin (hedgehog/Ig) fusion protein. In particular, we have developed a chimeric hedgehog composition with increased bioavailability relative to non-chimeric hedgehog and that further has the salutory properties of having reduced susceptibility to clipping by intracellular proteases. Thus, modifications can be made to the hedgehog moiety such that the products (e.g., hedgehog immunoglobulin fusion proteins) are either agonists or antagonists but retain all or most of their biological activities. The following properties may result: altered pharmacokinetics and pharmacodynamics leading to increased half-life and alterations in tissue distribution (e.g, ability to stay in the vasculature for longer periods of time). In particular, the ability to remain for longer periods of time in the vasculature allows the chimeric hedgehog proteins to potentially cross the blood-brain barrier.

In particular, an immunoglobulin (Ig)/hedgehog fusion protein relates to an isolated polypeptide having the amino acid sequence X-Y-Z, wherein X is a polypeptide having the amino acid sequence, or portion thereof, consisting of a hedgehog polypeptide; Y is an optional linker moiety; and Z is a polypeptide comprising at least a portion of a polypeptide other than hedgehog . Preferably, X is human Sonic, Indian or Desert hedgehog and most preferably, a biologically active N-terminal fragment of a hedgehog, including both agonist and antagonist forms. In the preferred embodiments, Z is at least a portion of protein with an immunoglobulin-like domain ("Ig-like domain" or "Ig-like region", used interchangeably). Most preferably, Z is at least a portion of a constant region of an immunoglobulin and can be derived from an immunoglobulin of the class selected from IgM, IgG, IgD, IgA, and IgE. If the class is IgG, then it is selected from one of IGG1, IgG2, IgG3 and IgG4. The constant region of human IgM and IgE contain 4 constant regions (CH1, (hinge), CH2, CH3 and CH4, whereas the constant region of human IgG, IgA and IgD contain 3 constant regions (CH1, (hinge), $CH_2$ and CH3. In the most preferred fusion proteins of the invention, the constant region contains at least the hinge, $CH_2$ and CH3 domains. Moiety "Z" and optional moiety "Y" can be attached at either the N- or C-terninus of hedgehog or attached to both termini.

The cDNA sequence encoding the hedgehog molecule or fragment may be directly joined to the CDNA encoding the heavy Ig contant regions or may be joined via a linker sequence. In further embodiments of the invention, a recombinant vector system may be created to accommodate sequences encoding hedgehog in the correct reading frame with a synthetic hinge region. Additionally, it may be desirable to include, as part of the recombinant vector system, nucleic acids corresponding to the 3' flanking region of an immunoglobulin gene including RNA cleavage/ polyadenylation sites and downstream sequences. Furthermore, it may be desirable to engineer a signal sequence upstream of the immunoglobulin fusion protein-encoding sequences to facilitate the secretion of the fused molecule from a cell transformed with the recombinant vector.

The present invention provides for dimeric fusion molecules as well as monomeric or multimeric molecules comprising fusion proteins. Such multimers may be generated by using those Fc regions, or portions thereof, of Ig molecules which are usually multivalent such as IgM pentamers or IgA dimers. It is understood that a J chain polypeptide may be needed to form and stabilize IgM pentamers and IgA dimers. Alternatively, multimers of hedgehog fusion proteins may be formed using a protein with an affinity for the Fc region of Ig molecules, such as Protein A. For instance, a plurality of hedgehog/immunoglobulin fusion proteins may be bound to Protein A-agarose beads.

Another embodiment of the invention is a chimeric protein having an amino terminal region consisting of the amino acid sequence of hedgehog or a portion thereof and having a carboxy terminal region comprising at least a portion of a protein other than hedgehog. The carboxy portion is preferably at least a portion of a constant region of an immunoglobulin derived from an immunoglobulin of the class selected from IgM, IgG, IgD, IgA, and IgE. In the most preferred chimeric proteins of this type, the constant region contains at least the hinge, $CH_2$ and CH3 domains.

The hedgehog polypeptide portion of the hedgehog/Ig fusion may be modified as described supra.

Moreover, mutagenesis can be used to create modified hh polypeptides, e.g., for such purposes as enhancing therapeutic or prophylactic efficacy, or stability (e.g., ex vivo shelf life and resistance to proteolytic degradation in vivo). Such modified peptides can be produced, for instance, by amino acid substitution, deletion, or addition. Modified hedgehog polypeptides can also include those with altered post-translational processing relative to a naturally occurring hedgehog protein, e.g., altered glycosylation, cholesterolization, prenylation and the like.

In one embodiment, the hedgehog therapeutic is a polypeptide encodable by a nucleotide sequence that hybridizes under stringent conditions to a hedgehog coding sequence represented in one or more of SEQ ID Nos:1–7. Appropriate stringency conditions which promote DNA hybridization, for example, 6.0× sodium chloride/sodium citrate (SSC) at about 45° C., followed by a wash of 2.0×SSC at 50° C., are known to those skilled in the art or can be found in *Current Protocols in Molecular Biology*, John Wiley & Sons, N.Y. (1989), 6.3.1.–6.3.6. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C.

As described in the literature, genes for other hedgehog proteins, e.g., from other animals, can be obtained from mRNA or genomic DNA samples using techniques well known in the art. For example, a cDNA encoding a hedgehog protein can be obtained by isolating total mRNA from a cell, e.g. a mammalian cell, e.g. a human cell, including embryonic cells. Double stranded cDNAs can then be prepared from the total mRNA, and subsequently inserted into a suitable plasmid or bacteriophage vector using any one of a number of known techniques. The gene encoding a hedgehog protein can also be cloned using established polymerase chain reaction techniques.

Preferred nucleic acids encode a hedgehog polypeptide comprising an amino acid sequence at least 60% homologous or identical, more preferably 70% homologous or identical, and most preferably 80% homologous or identical with an amino acid sequence selected from the group consisting of SEQ ID Nos:8–14. Nucleic acids which encode polypeptides at least about 90%, more preferably at least about 95%, and most preferably at least about 98–99% homology or identity with an amino acid sequence represented in one of SEQ ID Nos:8–14 are also within the scope of the invention.

In addition to native hedgehog proteins, hedgehog polypeptides preferred by the present invention are at least 60% homologous or identical, more preferably 70% homologous or identical and most preferably 80% homologous or identical with an amino acid sequence represented by any of SEQ ID Nos:8–14. Polypeptides which are at least 90%, more preferably at least 95%, and most preferably at least about 98–99% homologous or identical with a sequence selected from the group consisting of SEQ ID Nos:8–14 are also within the scope of the invention. The only prerequisite is that the hedgehog polypeptide is capable of modulating the growth state of peripheral nerve cells.

The term "recombinant protein" refers to a polypeptide of the present invention which is produced by recombinant DNA techniques, wherein generally, DNA encoding a hedgehog polypeptide is inserted into a suitable expression vector which is in turn used to transform a host cell to produce the heterologous protein. Moreover, the phrase "derived from", with respect to a recombinant hedgehog gene, is meant to include within the meaning of "recombinant protein"those proteins having an amino acid sequence of a native hedgehog protein, or an amino acid sequence similar thereto which is generated by mutations including substitutions and deletions (including truncation) of a naturally occurring form of the protein.

The method of the present invention can also be carried out using variant forms of the naturally occurring hedgehog polypeptides, e.g., mutational variants.

As is known in the art, hedgehog polypeptides can be produced by standard biological techniques or by chemical synthesis. For example, a host cell transfected with a nucleic acid vector directing expression of a nucleotide sequence encoding the subject polypeptides can be cultured under appropriate conditions to allow expression of the peptide to occur. The polypeptide hedgehog may be secreted and isolated from a mixture of cells and medium containing the recombinant hedgehog polypeptide. Alternatively, the peptide may be retained cytoplasmically by removing the signal peptide sequence from the recombinant hedgehog gene and the cells harvested, lysed and the protein isolated. A cell culture includes host cells, media and other byproducts. Suitable media for cell culture are well known in the art. The recombinant hedgehog polypeptide can be isolated from cell culture medium, host cells, or both using techniques known in the art for purifying proteins including ion-exchange chromatography, gel filtration chromatography, ultrafiltration, electrophoresis, and immunoaffinity purification with antibodies specific for such peptide. In a preferred embodiment, the recombinant hedgehog polypeptide is a fusion protein containing a domain which facilitates its purification, such as an hedgehog/GST fusion protein. The host cell may be any prokaryotic or eukaryotic cell.

Recombinant hedgehog genes can be produced by ligating nucleic acid encoding an hedgehog protein, or a portion thereof, into a vector suitable for expression in either prokaryotic cells, eukaryotic cells, or both. Expression vectors for production of recombinant forms of the subject hedgehog polypeptides include plasmids and other vectors. For instance, suitable vectors for the expression of a hedgehog polypeptide include plasmids of the types: pBR322-derived plasmids, pEMBL-derived plasmids, pEX-derived plasmids, pBTac-derived plasmids and pUC-derived plasmids for expression in prokaryotic cells, such as *E. coli*.

A number of vectors exist for the expression of recombinant proteins in yeast. For instance, YEP24, YIP5, YEP51, YEP52, pYES2, and YRP17 are cloning and expression vehicles useful in the introduction of genetic constructs into *S. cerevisiae* (see, for example, Broach et al. (1983) in *Experimental Manipulation of Gene Expression*, ed. M. Inouye Academic Press, p. 83, incorporated by reference herein). These vectors can replicate in *E. coli* due to the presence of the pBR322 ori, and in *S. cerevisiae* due to the replication determinant of the yeast 2 micron plasmid. In addition, drug resistance markers such as ampicillin can be used. In an illustrative embodiment, an hedgehog polypeptide is produced recombinantly utilizing an expression vector generated by sub-cloning the coding sequence of one of the hedgehog genes represented in SEQ ID Nos:1–7.

The preferred mammalian expression vectors contain both prokaryotic sequences, to facilitate the propagation of the vector in bacteria, and one or more eukaryotic transcription units that are expressed in eukaryotic cells. The pcDNAI/amp, pcDNAI/neo, pRc/CMV, pSV2gpt, pSV2neo, pSV2-dhfr, pTk2, pRSVneo, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the bovine papillomavirus (BPV-1), or Epstein-Barr virus (pHEBo, pREP-derived and p205) can be used for transient expression of proteins in eukaryotic cells. The various methods employed in the preparation of the plasmids and transformation of host organisms are well known in the art. For other suitable expression systems for both prokaryotic and eukaryotic cells, as well as general recombinant procedures, see *Molecular Cloning A Laboratory Manual*, 2nd Ed., ed. by Sambrook, Fritsch and Maniatis (Cold Spring Harbor Laboratory Press: 1989) Chapters 16 and 17.

In some instances, it may be desirable to express the recombinant hedgehog polypeptide by the use of a baculovirus expression system. Examples of such baculovirus expression systems include pVL-derived vectors (such as pVL1392, pVL1393 and pVL941), pAcUW-derived vectors (such as pAcUW1), and pBlueBac-derived vectors (such as the β-gal containing pBlueBac III).

When it is desirable to express only a portion of an hedgehog protein, such as a form lacking a portion of the N-terminus, i.e. a truncation mutant which lacks the signal peptide, it may be necessary to add a start codon (ATG) to the oligonucleotide fragment containing the desired sequence to be expressed. It is well known in the art that a methionine at the N-terminal position can be enzymatically cleaved by the use of the enzyme methionine aminopeptidase (MAP). MAP has been cloned from *E. coli* (Ben-Bassat et al. (1987) *J. Bacteriol.* 169:751–757) and *Salmonella typhimurium* and its in vitro activity has been demonstrated on recombinant proteins (Miller et al. (1987) *PNAS* 84:2718–1722). Therefore, removal of an N-terminal methionine, if desired, can be achieved either in vivo by expressing hedgehog-derived polypeptides in a host which produces MAP (e.g., *E. coli* or CM89 or *S. cerevisiae*), or in vitro by use of purified MAP (e.g., procedure of Miller et al., supra).

Alternatively, the coding sequences for the polypeptide can be incorporated as a part of a fusion gene including a nucleotide sequence encoding a different polypeptide. It is widely appreciated that fusion proteins can also facilitate the expression of proteins, and accordingly, can be used in the expression of the hedgehog polypeptides of the present invention. For example, hedgehog polypeptides can be generated as glutathione-S-transferase (GST-fusion) proteins. Such GST-fusion proteins can enable easy purification of the hedgehog polypeptide, as for example by the use of glutathione-derivatized matrices (see, for example, *Current Protocols in Molecular Biology*, eds. Ausubel et al. (N.Y.: John Wiley & Sons, 1991)). In another embodiment, a fusion gene coding for a purification leader sequence, such as a poly-(His)/enterokinase cleavage site sequence, can be used to replace the signal sequence which naturally occurs at the N-terminus of the hedgehog protein (e.g. of the pro-form, in order to permit purification of the poly(His)-hedgehog protein by affinity chromatography using a $Ni^{2+}$ metal resin. The purification leader sequence can then be subsequently removed by treatment with enterokinase (e.g., see Hochuli et al. (1987) *J. Chromatography* 411:177; and Janknecht et al. *PNAS* 88:8972).

Techniques for making fusion genes are known to those skilled in the art. Essentially, the joining of various DNA fragments coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed to generate a chimeric gene sequence (see, for example, *Current Protocols in Molecular Biology*, eds. Ausubel et al. John Wiley & Sons: 1992).

Hedgehog polypeptides may also be chemically modified to create hedgehog derivatives by forming covalent or aggregate conjugates with other chemical moieties, such as glycosyl groups, cholesterol, isoprenoids, lipids, phosphate, acetyl groups and the like. Covalent derivatives of hedgehog proteins can be prepared by linking the chemical moieties to functional groups on amino acid sidechains of the protein or at the N-terminus or at the C-terminus of the polypeptide.

For instance, hedgehog proteins can be generated to include a moiety, other than sequence naturally associated with the protein, that binds a component of the extracellular matrix and enhances localization of the analog to cell surfaces. For example, sequences derived from the fibronectin "type-III repeat", such as a tetrapeptide sequence R-G-D-S (Pierschbacher et al. (1984) *Nature* 309:30–3; and Kornblihtt et al. (1985) *EMBO* 4:1755–9) can be added to the hedgehog polypeptide to support attachment of the chimeric molecule to a cell through binding ECM components (Ruoslahti et al. (1987) *Science* 238:491–497; Pierschbacher al. (1987) *J. Biol. Chem.* 262:17294–8.; Hynes (1987) *Cell* 48:549–54; and Hynes (1992) *Cell* 69:11–25).

In a preferred embodiment, the hedgehog polypeptide is isolated from, or is otherwise substantially free of, other cellular proteins, especially other extracellular or cell surface associated proteins which may normally be associated with the hedgehog polypeptide, unless provided in the form of fusion protein with the hedgehog polypeptide. The term "substantially free of other cellular or extracellular proteins" (also referred to herein as "contaminating proteins") or "substantially pure preparations" or "purified preparations" are defined as encompassing preparations of hedgehog polypeptides having less than 20% (by dry weight) contaminating protein, and preferably having less than 5% contaminating protein. By "purified", it is meant that the indicated molecule is present in the substantial absence of other biological macromolecules, such as other proteins. The term "purified" as used herein preferably means at least 80% by dry weight, more preferably in the range of 95–99% by weight, and most preferably at least 99.8% by weight, of biological macromolecules of the same type present (but water, buffers, and other small molecules, especially molecules having a molecular weight of less than 5000, can be present). The term "pure" as used herein preferably has the same numerical limits as "purified" immediately above.

As described above for recombinant polypeptides, isolated hedgehog polypeptides can include all or a portion of the amino acid sequences represented in any of SEQ ID Nos:10–18 or 20, or a homologous sequence thereto. Preferred fragments of the subject hedgehog proteins correspond to the N-terminal and C-terminal proteolytic fragments of the mature protein. Bioactive fragments of hedgehog polypeptides are described in great detail in PCT publications WO 95/18856 and WO 96/17924.

With respect to bioctive fragments of hedgehog polypeptide, preferred hedgehog therapeutics include at least 50 (contiguous) amino acid residues of a hedgehog polypeptide, more preferably at least 100 (contiguous), and even more preferably at least 150 (contiguous) residues.

Another preferred hedgehog polypeptide which can be included in the hedgehog therapeutic is an N-terminal fragment of the mature protein having a molecular weight of approximately 19 kDa.

Preferred human hedgehog proteins include N-terminal fragments corresponding approximately to residues 24–197 of SEQ ID No. 15, 28–202 of SEQ ID No. 16, and 23–198 of SEQ ID No. 17. By "corresponding approximately" it is meant that the sequence of interest is at most 20 amino acid residues different in length to the reference sequence, though more preferably at most 5, 10 or 15 amino acid different in length.

As described above for recombinant polypeptides, isolated hedgehog polypeptides can include all or a portion of the amino acid sequences represented in SEQ ID No:8, SEQ ID No:9, SEQ ID No:10, SEQ ID No:11, SEQ ID No:12, SEQ ID No:13 or SEQ ID No:14, or a homologous sequence thereto. Preferred fragments of the subject hedgehog proteins correspond to the N-terminal and C-terminal proteolytic fragments of the mature protein. Bioactive fragments of hedgehog polypeptides are described in great detail in PCT publications WO 95/18856 and WO 96/17924.

Still other preferred hedgehog polypeptides includes an amino acid sequence represented by the formula A-B wherein: (i) A represents all or the portion of the amino acid sequence designated by residues 1–168 of SEQ ID No:21; and B represents at least one amino acid residue of the amino acid sequence designated by residues 169–221 of SEQ ID No:21; (ii) A represents all or the portion of the amino acid sequence designated by residues 24–193 of SEQ ID No:15; and B represents at least one amino acid residue of the amino acid sequence designated by residues 194–250 of SEQ ID No:15; (iii) A represents all or the portion of the amino acid sequence designated by residues 25–193 of SEQ ID No:13; and B represents at least one amino acid residue of the amino acid sequence designated by residues 194–250 of SEQ ID No: 13; (iv) A represents all or the portion of the amino acid sequence designated by residues 23–193 of SEQ ID No:11; and B represents at least one amino acid residue of the amino acid sequence designated by residues 194–250 of SEQ ID No:11; (v) A represents all or the portion of the amino acid sequence designated by residues 28–197 of SEQ ID No:12; and B represents at least one amino acid residue of the amino acid sequence designated by residues 198–250 of SEQ ID No:12; (vi) A represents all or the portion of the amino acid sequence designated by residues 29–197 of SEQ ID No:16; and B represents at least one amino acid residue of the amino acid sequence designated by residues 198–250 of SEQ ID No:16; or (vii) A represents all or the portion of the amino acid sequence designated by residues 23–193 of SEQ ID No. 17, and B represents at least one amino acid residue of the amino acid sequence designated by residues 194–250 of SEQ ID No. 17. In certain preferred embodiments, A and B together represent a contiguous polypeptide sequence designated sequence, A represents at least 25, 50, 75, 100, 125 or 150 (contiguous) amino acids of the designated sequence, and B represents at least 5, 10, or 20 (contiguous) amino acid residues of the amino acid sequence designated by corresponding entry in the sequence listing, and A and B together preferably represent a contiguous sequence corresponding to the sequence listing entry. Similar fragments from other hedgehog also contemplated, e.g., fragments which correspond to the preferred fragments from the sequence listing entries which are enumerated above. In preferred embodiments, the hedgehog polypeptide includes a C-terminal glycine (or other appropriate residue) which is derivatized with a cholesterol.

Isolated peptidyl portions of hedgehog proteins can be obtained by screening peptides recombinantly produced from the corresponding fragment of the nucleic acid encoding such peptides. In addition, fragments can be chemically synthesized using techniques known in the art such as conventional Merrifield solid phase f-Moc or t-Boc chemistry. For example, a hedgehog polypeptide of the present invention may be arbitrarily divided into fragments of desired length with no overlap of the fragments, or preferably divided into overlapping fragments of a desired length. The fragments can be produced (recombinantly or by chemical synthesis) and tested to identify those peptidyl fragments which can function as either agonists or antagonists of a wild-type (e.g., "authentic") hedgehog protein. For example, Román et al. (1994) *Eur J Biochem* 222:65–73 describe the use of competitive-binding assays using short, overlapping synthetic peptides from larger proteins to identify binding domains.

The recombinant hedgehog polypeptides of the present invention also include homologs of the authentic hedgehog proteins, such as versions of those protein which are resistant to proteolytic cleavage, as for example, due to mutations which alter potential cleavage sequences or which inactivate an enzymatic activity associated with the protein. Hedgehog homologs of the present invention also include proteins which have been post-translationally modified in a manner different than the authentic protein. Exemplary derivatives of hedgehog proteins include polypeptides which lack N-glycosylation sites (e.g. to produce an unglycosylated protein), which lack sites for cholesterolization, and/or which lack N-terminal and/or C-terminal sequences.

Modification of the structure of the subject hedgehog polypeptides can also be for such purposes as enhancing therapeutic or prophylactic efficacy, or stability (e.g., ex vivo shelf life and resistance to proteolytic degradation in vivo). Such modified peptides, when designed to retain at least one activity of the naturally-occurring form of the protein, are considered functional equivalents of the hedgehog polypeptides described in more detail herein. Such modified peptides can be produced, for instance, by amino acid substitution, deletion, or addition.

It is well known in the art that one could reasonably expect that certain isolated replacements of amino acids, e.g., replacement of an amino acid residue with another related amino acid (i.e. isosteric and/or isoelectric mutations), can be carried out without major effect on the biological activity of the resulting molecule. Conservative replacements are those that take place within a family of amino acids that are related in their side chains. Genetically encoded amino acids are can be divided into four families: (1) acidic=aspartate, glutamate; (2) basic=lysine, arginine, histidine; (3) nonpolar=alanine, valine, leucine, isoleucine, proline, phenylalanine, methionine, tryptophan; and (4) uncharged polar=glycine, asparagine, glutamine, cysteine, serine, threonine, tyrosine. Phenylalanine, tryptophan, and tyrosine are sometimes classified jointly as aromatic amino acids. In similar fashion, the amino acid repertoire can be grouped as (1) acidic=aspartate, glutamate; (2) basic=lysine, arginine histidine, (3) aliphatic=glycine, alanine, valine, leucine, isoleucine, serine, threonine, with serine and threonine optionally be grouped separately as aliphatic-hydroxyl; (4) aromatic=phenylalanine, tyrosine, tryptophan; (5) amide=asparagine, glutamine; and (6) sulfur-containing= cysteine and methionine. (see, for example, *Biochemistry*, 2nd ed., Ed. by L. Stryer, WH Freeman and Co.: 1981). Whether a change in the amino acid sequence of a peptide results in a functional hedgehog homolog (e.g. functional in the sense that it acts to mimic or antagonize the wild-type form) can be readily determined by assessing the ability of the variant peptide to produce a response in cells in a fashion similar to the wild-type protein, or competitively inhibit such a response. Polypeptides in which more than one replacement has taken place can readily be tested in the same manner.

It is specifically contemplated that the methods of the present invention can be carried using homologs of naturally occurring hedgehog proteins. In one embodiment, the invention contemplates using hedgehog polypeptides generated by combinatorial mutagenesis. Such methods, as are known in the art, are convenient for generating both point and truncation mutants, and can be especially useful for identifying potential variant sequences (e.g. homologs) that are functional in binding to a receptor for hedgehog proteins. The purpose of screening such combinatorial libraries is to generate, for example, novel hedgehog homologs which can act as either agonists or antagonist. To illustrate, hedgehog homologs can be engineered by the present method to provide more efficient binding to a cognate receptor, such as patched, yet still retain at least a portion of an activity associated with hedgehog. Thus, combinatorially-derived homologs can be generated to have an increased potency relative to a naturally occurring form of the protein. Likewise, hedgehog homologs can be generated by the present combinatorial approach to act as antagonists, in that they are able to mimic, for example, binding to other extracellular matrix components (such as receptors), yet not induce any biological response, thereby inhibiting the action of authentic hedgehog or hedgehog agonists. Moreover, manipulation of certain domains of hedgehog by the present method can provide domains more suitable for use in fusion proteins, such as one that incorporates portions of other proteins which are derived from the extracellular matrix and/or which bind extacellular matrix components.

To further illustrate the state of the art of combinatorial mutagenesis, it is noted that the review article of Gallop et al. (1994) *J Med Chem* 37:1233 describes the general state of the art of combinatorial libraries as of the earlier 1990's. In particular, Gallop et al state at page 1239 "[s]creening the analog libraries aids in determining the minimum size of the active sequence and in identifying those residues critical for binding and intolerant of substitution". In addition, the Ladner et al. PCT publication WO90/02809, the Goeddel et al. U.S. Pat. No. 5,223,408, and the Markland et al. PCT publication WO92/15679 illustrate specific techniques which one skilled in the art could utilize to generate libraries of hedgehog variants which can be rapidly screened to identify variants/fragments which retained a particular activity of the hedgehog polypeptides. These techniques are exemplary of the art and demonstrate that large libraries of related variants/truncants can be generated and assayed to isolate particular variants without undue experimentation. Gustin et al. (1993) *Virology* 193:653, and Bass et al. (1990) *Proteins:*

Structure, Function and Genetics 8:309–314 also describe other exemplary techniques from the art which can be adapted as means for generating mutagenic variants of hedgehog polypeptides.

Indeed, it is plain from the combinatorial mutagenesis art that large scale mutagenesis of hedgehog proteins, without any preconceived ideas of which residues were critical to the biological function, and generate wide arrays of variants having equivalent biological activity.

Indeed, it is the ability of combinatorial techniques to screen billions of different variants by high throughout analysis that removes any requirement of a priori understanding or knowledge of critical residues.

To illustrate, the amino acid sequences for a population of hedgehog homologs or other related proteins are aligned, preferably to promote the highest homology possible. Such a population of variants can include, for example, hedgehog homologs from one or more species. Amino acids which appear at each position of the aligned sequences are selected to create a degenerate set of combinatorial sequences. In a preferred embodiment, the variegated library of hedgehog variants is generated by combinatorial mutagenesis at the nucleic acid level, and is encoded by a variegated gene library. For instance, a mixture of synthetic oligonucleotides can be enzymatically ligated into gene sequences such that the degenerate set of potential hedgehog sequences are expressible as individual polypeptides, or alternatively, as a set of larger fusion proteins (e.g. for phage display) containing the set of hedgehog sequences therein.

As illustrated in PCT publication WO 95/18856, to analyze the sequences of a population of variants, the amino acid sequences of interest can be aligned relative to sequence homology. The presence or absence of amino acids from an aligned sequence of a particular variant is relative to a chosen consensus length of a reference sequence, which can be real or artificial.

In an illustrative embodiment, alignment of exons 1, 2 and a portion of exon 3 encoded sequences (e.g. the N-terminal approximately 221 residues of the mature protein) of each of the Shh clones produces a degenerate set of Shh polypeptides represented by the general formula:

C-G-P-G-R-G-X(1)-G-X(2)-R-R-H-P-K-K-L-T-P-L-A-Y-K-Q-F-I-P-N-V-A-E-

K-T-L-G-A-S-G-R-Y-E-G-K-I-X(3)-R-N-S-E-R-F-K-E-L-T-P-N-Y-N-P-D--I-F-

K-D-E-E-N-T-G-A-D-R-L-M-T-Q-R-C-K-D-K-L-N-X(4)-L-A-I-S-V-M-N-X(5)-

W-P-G-V-X(6)-L-R-V-T-E-G-W-D-E-D-G-H-H-X(7)-E-E-S-L-H-Y-E-G-R-A-

V-D-I-T-T-S-D-R-D-X(8)-S-K-Y-G-X(9)-L-X(10)-R-L-A-V-E-A-G-F-D-W-V-

Y-Y-E-S-K-A-H-I-H-C-S-V-K-A-E-N-S-V-A-A-K-S-G-G-C-F-P-G-S-A-X(11)-

V-X(12)-L-X(13)-X(14)-G-G-X(15)-K-X-(16)-V-K-D-L-X(17)-P-G-D-X(18)-V-

L-A-A-D-X(19)-X(20)-G-X(21)-L-X(22)-X(23)-S-D-F-X(24)-X(25)-F-X(26)-D-R
(SEQ ID No: 21 wherein each of the degenerate positions "X" can be an amino acid which occurs in that position in one of the human, mouse, chicken or zebrafish Shh clones, or, to expand the library, each X can also be selected from amongst amino acid residue which would be conservative substitutions for the amino acids which appear naturally in each of those positions. For instance, Xaa(1) represents Gly, Ala, Val, Leu, Ile, Phe, Tyr or Trp; Xaa(2) represents Arg, His or Lys; Xaa(3) represents Gly, Ala, Val, Leu, Ile, Ser or Thr; Xaa(4) represents Gly, Ala, Val, Leu, Ile, Ser or Thr; Xaa(5) represents Lys, Arg, His, Asn or Gln; Xaa(6) represents Lys, Arg or His; Xaa(7) represents Ser, Thr, Tyr, Trp or Phe; Xaa(8) represents Lys, Arg or His; Xaa(9) represents Met, Cys, Ser or Thr; Xaa(10) represents Gly, Ala, Val, Leu, Ile, Ser or Thr; Xaa(11) represents Leu, Val, Met, Thr or Ser; Xaa(12) represents His, Phe, Tyr, Ser, Thr, Met or Cys; Xaa(13) represents Gln, Asn, Glu, or Asp; Xaa(14) represents His, Phe, Tyr, Thr, Gln, Asn, Glu or Asp; Xaa(15) represents Gln, Asn, Glu, Asp, Thr, Ser, Met or Cys; Xaa(16) represents Ala, Gly, Cys, Leu, Val or Met; Xaa(17) represents Arg, Lys, Met, Ile, Asn, Asp, Glu, Gln, Ser, Thr or Cys; Xaa(18) represents Arg, Lys, Met or Ile; Xaa(19) represents Ala, Gly, Cys, Asp, Glu, Gin, Asn, Ser, Thr or Met; Xaa(20) represents Ala, Gly, Cys, Asp, Asn, Glu or Gln; Xaa(21) represents Arg, Lys, Met, Ile, Asn, Asp, Glu or Gln; Xaa(22) represent Leu, Val, Met or Ile; Xaa(23) represents Phe, Tyr, Thr, His or Trp; Xaa(24) represents Ile, Val, Leu or Met; .Xaa(25) represents Met, Cys, Ile, Leu, Val, Thr or Ser; Xaa(26) represents Leu, Val, Met, Thr or Ser. In an even more expansive library, each X can be selected from any amino acid.

In similar fashion, alignment of each of the human, mouse, chicken and zebrafish hedgehog clones, can provide a degenerate polypeptide sequence represented by the general formula:

C-G-P-G-R-G-X(1)-X(2)-X(3)-R-R-X(4)-X(5)-X(6)-P-K-X(7)-L-X(8)-P-L-X(9)-

Y-K-Q-F-X(10)-P-X(11)-X(12)-X(13)-E-X(14)-T-L-G-A-S-G-X(15)-X(16)E-G-

X(17)-X(18)-X(19)-R-X(20)-S-E-R-F-X(21)-X(22)-L-T-P-N-Y-N-P-D-I-I-F-K-

D-E-E-N-X(23)-G-A-D-R-L-M-T-X(24)-R-C-K-X(25)-X(26)-X(27)-N-X(28)-L-

A-I-S-V-M-N-X(29)-W-PG-V-X(30)-L-R-V-T-E-G-X(31)-D-E-D-G-H-H-

X(32)-X(33)-X(34)-S-L-H-Y-E-G-R-A-X(35)-D-I-T-T-S-D-R-D-X(36)-X(37)-K-

Y-G-X(38)-L-X(39)-R-L-A-V-E-A-G-F-D-W-V-Y-Y-E-S-X(40)-X(41)-H-X(42)-

H-X(43)-S-V-K-X(44)-X(45) (SEQ IDNo:22 wherein, as above, each of the degenerate positions "X" can be an amino acid which occurs in a corresponding position in one of the wild-type clones, and may also include amino acid residue which would be conservative substitutions, or each X can be any amino acid residue. In an exemplary embodiment, Xaa(1) represents Gly, Ala, Val, Leu, Ile, Pro, Phe or Tyr; Xaa(2) represents Gly, Ala, Val, Leu or Ile; Xaa(3) represents Gly, Ala, Val, Leu, Ile, Lys, His or Arg; Xaa(4) represents Lys, Arg or His; Xaa(5) represents Phe, Trp, Tyr or an amino acid gap; Xaa(6) represents Gly, Ala, Val, Leu, Ile or an amino acid gap; Xaa(7) represents Asn, Gln, His, Arg or Lys; Xaa(8) represents Gly, Ala, Val, Leu, Ile, Ser or Thr; Xaa(9) represents Gly, Ala, Val, Leu, Ile, Ser or Thr; Xaa(10) represents Gly, Ala, Val, Leu, Ile, Ser or Thr, Xaa(11) represents Ser, Thr, Gln or Asn; Xaa(12) represents Met, Cys, Gly, Ala, Val, Leu, Ile, Ser or Thr, Xaa(13) represents Gly, Ala, Val, Leu, Ile or Pro; Xaa(14) represents Arg, His or Lys; Xaa(15) represents Gly, Ala, Val, Leu, Ile, Pro, Arg, His or Lys; Xaa(16) represents Gly, Ala, Val, Leu, Ile, Phe or Tyr; Xaa(17) represents Arg, His or Lys; Xaa(18) represents Gly, Ala, Val, Leu, Ile, Ser or Thr; Xaa(19) represents Thr or Ser; Xaa(20) represents Gly, Ala, Val, Leu, Ile, Asn or Gln; Xaa(21) represents Arg, His or Lys; Xaa(22) represents Asp or Glu; Xaa(23) represents Ser or Thr; Xaa(24) represents Glu, Asp, Gln or Asn; Xaa(25) represents Glu or Asp; Xaa(26) represents Arg, His or Lys; Xaa(27) represents Gly, Ala, Val, Leu or Ile; Xaa(28) represents Gly, Ala, Val, Leu, Ile, Thr or Ser; Xaa(29) represents Met, Cys, Gln, Asn, Arg, Lys or His; Xaa(30) represents Arg, His or Lys; Xaa(31) represents Trp, Phe, Tyr, Arg, His or Lys; Xaa(32) represents Gly, Ala, Val, Leu, Ile, Ser, Thr, Tyr or Phe; Xaa(33) represents Gln, Asn, Asp or Glu; Xaa(34) represents Asp or Glu; Xaa(35) represents Gly, Ala, Val, Leu, or Ile; Xaa(36) represents Arg, His or Lys; Xaa(37) represents Asn, Gln, Thr or Ser; Xaa(38) represents Gly, Ala, Val, Leu, Ile, Ser, Thr, Met or Cys; Xaa(39) represents Gly, Ala, Val, Leu, Ile, Thr or Ser; Xaa(40) represents Arg, His or Lys; Xaa(41) represents Asn, Gln, Gly, Ala, Val, Leu or Ile; Xaa(42) represents Gly, Ala, Val, Leu or Ile; Xaa(43) represents Gly, Ala, Val, Leu, Ile, Ser, Thr or Cys; Xaa(44) represents Gly, Ala, Val, Leu, Ile, Thr or Ser; and Xaa(45) represents Asp or Glu.

There are many ways by which the library of potential hedgehog homologs can be generated from a degenerate oligonucleotide sequence. Chemical synthesis of a degenerate gene sequence can be carried out in an automatic DNA synthesizer, and the synthetic genes then ligated into an appropriate expression vector. The purpose of a degenerate set of genes is to provide, in one mixture, all of the sequences encoding the desired set of potential hedgehog sequences. The synthesis of degenerate oligonucleotides is well known in the art (see for example, Narang, S A (1983) *Tetrahedron* 39:3; Itakura et al. (1981) *Recombinant DNA, Proc 3rd Cleveland Sympos. Macromolecules,* ed. A G Walton, Amsterdam: Elsevier pp273–289; Itakura et al. (1984) *Annu. Rev. Biochem.* 53:323; Itakura et al. (1984) *Science* 198:1056; Ike et al. (1983) *Nucleic Acid Res.* 11:477. Such techniques have been employed in the directed evolution of other proteins (see, for example, Scott et al. (1990) *Science* 249:386–390; Roberts et al. (1992) *PNAS* 89:2429–2433; Devlin et al. (1990) *Science* 249: 404–406; Cwirla et al. (1990) *PNAS* 87: 6378–6382; as well as U.S. Pat. Nos. 5,223,409, 5,198,346, and 5,096,815).

A wide range of techniques are known in the art for screening gene products of combinatorial libraries made by point mutations, and for screening cDNA libraries for gene products having a certain property. Such techniques will be generally adaptable for rapid screening of the gene libraries generated by the combinatorial mutagenesis of hedgehog homologs. The most widely used techniques for screening large gene libraries typically comprises cloning the gene library into replicable expression vectors, transforming appropriate cells with the resulting library of vectors, and expressing the combinatorial genes under conditions in which detection of a desired activity facilitates relatively easy isolation of the vector encoding the gene whose product was detected. Each of the illustrative assays described below are amenable to high through-put analysis as necessary to screen large numbers of degenerate hedgehog sequences created by combinatorial mutagenesis techniques.

In one embodiment, the combinatorial library is designed to be secreted (e.g. the polypeptides of the library all include a signal sequence but no transmembrane or cytoplasmic domains), and is used to transfect a eukaryotic cell that can be co-cultured with peripehral nerve cells. A functional hedgehog protein secreted by the cells expressing the combinatorial library will diffuse to neighboring peripheral nerve cells and induce a particular biological response, such as proliferation or differentiation. The pattern of detection of such a change in phenotype will resemble a gradient function, and will allow the isolation (generally after several repetitive rounds of selection) of cells producing hedgehog homologs active as neurotrophic agents. Likewise, hedgehog antagonists can be selected in similar fashion by the ability of the cell producing a functional antagonist to protect neighboring cells (e.g., to inhibit proliferation) from the effect of wild-type hedgehog added to the culture media.

To illustrate, target peripheral nerve cells are cultured in 24-well microtitre plates. Other eukaryotic cells are transfected with the combinatorial hedgehog gene library and cultured in cell culture inserts (e.g. Collaborative Biomedical Products, Catalog #40446) that are able to fit into the wells of the microtitre plate. The cell culture inserts are placed in the wells such that recombinant hedgehog homologs secreted by the cells in the insert can diffuse through the porous bottom of the insert and contact the target cells in the microtitre plate wells. After a period of time sufficient for functional forms of a hedgehog protein to produce a measurable response in the target cells, such as growth state, the inserts are removed and the effect of the variant hedgehog proteins on the target cells determined. Cells from the inserts corresponding to wells which score positive for activity can be split and re-cultured on several inserts, the process being repeated until the active clones are identified.

In yet another screening assay, the candidate hedgehog gene products are displayed on the surface of a cell or viral particle, and the ability of particular cells or viral particles to associate with a hedgehog-binding moiety (such as the patched protein or other hedgehog receptor) via this gene product is detected in a "panning assay". Such panning steps can be carried out on cells cultured from embryos. For instance, the gene library can be cloned into the gene for a surface membrane protein of a bacterial cell, and the resulting fusion protein detected by panning (Ladner et al., WO 88/06630; Fuchs et al. (1991) *Bio/Technology* 9:1370–1371; and Goward et al. (1992) *TIBS* 18:136–140). In a similar fashion, fluorescently labeled molecules which bind hedgehog can be used to score for potentially functional hedgehog homologs. Cells can be visually inspected and separated under a fluorescence microscope, or, where the morphology of the cell permits, separated by a fluorescence-activated cell sorter.

In an alternate embodiment, the gene library is expressed as a fusion protein on the surface of a viral particle. For instance, in the filamentous phage system, foreign peptide sequences can be expressed on the surface of infectious phage, thereby conferring two significant benefits. First, since these phage can be applied to affinity matrices at very high concentrations, large number of phage can be screened at one time. Second, since each infectious phage displays the combinatorial gene product on its surface, if a particular phage is recovered from an affinity matrix in low yield, the phage can be amplified by another round of infection. The group of almost identical *E. coli* filarnentous phages M13, fd, and fl are most often used in phage display libraries, as either of the phage gIII or gVIII coat proteins can be used to generate fusion proteins without disrupting the ultimate packaging of the viral particle (Ladner et al. PCT publication WO 90/02909; Garrard et al., PCT publication WO 92/09690; Marks et al. (1992) *J. Biol. Chem.* 267:16007–16010; Griffihs et al. (1993) *EMBO J* 12:725–734; Clackson et al. (1991) *Nature* 352:624–628; and Barbas et al. (1992) *PNAS* 89:4457–4461).

In an illustrative embodiment, the recombinant phage antibody system (RPAS, Pharmacia Catalog number 27-9400-01) can be easily modified for use in expressing and screening hedgehog combinatorial libraries. For instance, the pCANTAB 5 phagemid of the RPAS kit contains the gene which encodes the phage gIII coat protein. The hedgehog combinatorial gene library can be cloned into the phagemid adjacent to the gIII signal sequence such that it will be expressed as a gIII fusion protein. After ligation, the phagemid is used to transform competent E. coli TG1 cells. Transformed cells are subsequently infected with M13KO7 helper phage to rescue the phagemid and its candidate hedgehog gene insert. The resulting recombinant phage contain phagemid DNA encoding a specific candidate hedgehog, and display one or more copies of the corresponding fusion coat protein. The phage-displayed candidate hedgehog proteins which are capable of binding an hedgehog receptor are selected or enriched by panning. For instance, the phage library can be applied to cells which express the patched protein and unbound phage washed away from the cells. The bound phage is then isolated, and if the recombinant phage express at least one copy of the wild type gIII coat protein, they will retain their ability to infect E. coli. Thus, successive rounds of reinfection of E. coli, and panning will greatly enrich for hedgehog homologs, which can then be screened for further biological activities in order to differentiate agonists and antagonists.

Combinatorial mutagenesis has a potential to generate very large libraries of mutant proteins, e.g., in the order of $10^{26}$ molecules. Combinatorial libraries of this size may be technically challenging to screen even with high throughput screening assays such as phage display. To overcome this problem, a new technique has been developed recently, recursive ensemble mutagenesis (REM), which allows one to avoid the very high proportion of non-functional proteins in a random library and simply enhances the frequency of functional proteins, thus decreasing the complexity required to achieve a useful sampling of sequence space. REM is an algorithm which enhances the frequency of functional mutants in a library when an appropriate selection or screening method is employed (Arkin and Yourvan, 1992, *PNAS USA* 89:7811–7815; Yourvan et al., 1992, *Parallel Problem Solving from Nature*, 2., In Maenner and Manderick, eds., Elsevir Publishing Co., Amsterdam, pp. 401–410; Delgrave et al., 1993, *Protein Engineering* 6(3):327–331).

The invention also provides for reduction of the hedgehog protein to generate mimetics, e.g. peptide or non-peptide agents, which are able to disrupt binding of a hedgehog polypeptide of the present invention with an hedgehog receptor. Thus, such mutagenic techniques as described above are also useful to map the determinants of the hedgehog proteins which participate in protein-protein interactions involved in, for example, binding of the subject hedgehog polypeptide to other extracellular matrix components. To illustrate, the critical residues of a subject hedgehog polypeptide which are involved in molecular recognition of an hedgehog receptor such as patched can be determined and used to generate hedgehog-derived peptidomimetics which competitively inhibit binding of the authentic hedgehog protein with that moiety. By employing, for example, scanning mutagenesis to map the amino acid residues of each of the subject hedgehog proteins which are involved in binding other extracellular proteins, peptidomimetic compounds can be generated which mimic those residues of the hedgehog protein which facilitate the interaction. Such mimetics may then be used to interfere with the normal function of a hedgehog protein. For instance, non-hydrolyzable peptide analogs of such residues can be generated using benzodiazepine (e.g., see Freidinger et al. in *Peptides: Chemistry and Biology*, G. R. Marshall ed., ESCOM Publisher: Leiden, Netherlands, 1988), azepine (e.g., see Huffman et al. in *Peptides: Chemistry and Biology*, G. R. Marshall ed., ESCOM Publisher: Leiden, Netherlands, 1988), substituted gama lactam rings (Garvey et al. in *Peptides: Chemistry and Biology*, G. R. Marshall ed., ESCOM Publisher: Leiden, Netherlands, 1988), keto-methylene pseudopeptides (Ewenson et al. (1986) *J Med Chem* 29:295; and Ewenson et al. in *Peptides: Structure and Function* (Proceedings of the 9th American Peptide Symposium) Pierce Chemical Co. Rockland, Ill., 1985), β-turn dipeptide cores (Nagai et al. (1985) *Tetrahedron Lett* 26:647; and Sato et al. (1986) *J Chem Soc Perkin Trans* 1:1231), and β-aminoalcohols (Gordon et al. (1985) Biochem Biophys Res Commun 126:419; and Dann et al. (1986) *Biochem Biophys Res Commun* 134:71).

Recombinantly produced forms of the hedgehog proteins can be produced using, e.g, expression vectors containing a nucleic acid encoding a hedgehog polypeptide, operably linked to at least one transcriptional regulatory sequence. Operably linked is intended to mean that the nucleotide sequence is linked to a regulatory sequence in a manner which allows expression of the nucleotide sequence. Regulatory sequences are art-recognized and are selected to direct expression of a hedgehog polypeptide. Accordingly, the term transcriptional regulatory sequence includes promoters, enhancers and other expression control elements. Such regulatory sequences are described in Goeddel; *Gene Expression Technology: Methods in Enzymology* 185, Academic Press, San Diego, Calif. (1990). For instance, any of a wide variety of expression control sequences, sequences that control the expression of a DNA sequence when operatively linked to it, may be used in these vectors to express DNA sequences encoding hedgehog polypeptide. Such useful expression control sequences, include, for example, a viral LTR, such as the LTR of the Moloney murine leukemia virus, the early and late promoters of SV40, adenovirus or cytomegalovirus immediate early promoter, the lac system, the trp system, the TAC or TRC system, T7 promoter whose expression is directed by T7 RNA polymerase, the major operator and promoter regions of phage λ, the control regions for fd coat protein, the promoter for 3-phosphoglycerate kinase or other glycolytic enzymes, the promoters of acid phosphatase, e.g., Pho5, the promoters of the yeast α-mating factors, the polyhedron promoter of the baculovirus system and other sequences known to control the expression of genes of prokaryotic or eukaryotic cells or their viruses, and various combinations thereof. It should be understood that the design of the expression vector may depend on such factors as the choice of the host cell to be transformed and/or the type of protein desired to be expressed. Moreover, the vector's copy number, the ability to control that copy number and the expression of any other proteins encoded by the vector, such as antibiotic markers, should also be considered.

In addition to providing a ready source of hedgehog polypeptides for purification, the gene constructs of the present invention can also be used as a part of a gene therapy protocol to deliver nucleic acids encoding either an agonistic or antagonistic form of a hedgehog polypeptide. Thus, another aspect of the invention features expression vectors for in vivo transfection of a hedgehog polypeptide in particular cell types so as cause ectopic expression of a hedgehog polypeptide in an periperal neurons or other cells associated therewith.

Formulations of such expression constructs may be administered in any biologically effective carrier, e.g. any formulation or composition capable of effectively delivering the recombinant gene to cells in vivo. Approaches include insertion of the hedgehog coding sequence in viral vectors including recombinant retroviruses, adenovirus, adeno-associated virus, and herpes simplex virus-1, or recombinant bacterial or eukaryotic plasmids. Viral vectors transfect cells directly; plasmid DNA can be delivered with the help of, for example, cationic liposomes (lipofectin) or derivatized (e.g. antibody conjugated), polylysine conjugates, gramicidin S, artificial viral envelopes or other such intracellular carriers, as well as direct injection of the gene construct or $CaPO_4$ precipitation carried out in vivo. It will be appreciated that because transduction of appropriate target cells represents the critical first step in gene therapy, choice of the particular gene delivery system will depend on such factors as the phenotype of the intended target and the route of administration, e.g. locally or systemically. Furthermore, it will be recognized that the particular gene construct provided for in vivo transduction of hedgehog expression are also useful for in vitro transduction of cells, such as for use in the ex vivo tissue culture systems described below.

A preferred approach for in vivo introduction of nucleic acid into a cell is by use of a viral vector containing nucleic acid, e.g. a cDNA, encoding the particular form of the hedgehog polypeptide desired. Infection of cells with a viral vector has the advantage that a large proportion of the targeted cells can receive the nucleic acid. Additionally, molecules encoded within the viral vector, e.g., by a cDNA contained in the viral vector, are expressed efficiently in cells which have taken up viral vector nucleic acid.

Retrovirus vectors and adeno-associated virus vectors are generally understood to be the recombinant gene delivery system of choice for the transfer of exogenous genes in vivo, particularly into humans. These vectors provide efficient delivery of genes into cells, and the transferred nucleic acids are stably integrated into the chromosomal DNA of the host. A major prerequisite for the use of retroviruses is to ensure the safety of their use, particularly with regard to the possibility of the spread of wild-type virus in the cell population. The development of specialized cell lines (termed "packaging cells") which produce only replication-defective retroviruses has increased the utility of retroviruses for gene therapy, and defective retroviruses are well characterized for use in gene transfer for gene therapy purposes (for a review see Miller, A. D. (1990) *Blood* 76:271). Thus, recombinant retrovirus can be constructed in which part of the retroviral coding sequence (gag, pol, env) has been replaced by nucleic acid encoding a hedgehog polypeptide and renders the retrovirus replication defective. The replication defective retrovirus is then packaged into virions which can be used to infect a target cell through the use of a helper virus by standard techniques. Protocols for producing recombinant retroviruses and for infecting cells in vitro or in vivo with such viruses can be found in *Current Protocols in Molecular Biology*. Ausubel, F. M. et al. (eds.) Greene Publishing Associates, (1989), Sections 9.10–9.14 and other standard laboratory manuals. Examples of suitable retroviruses include pLJ, pZIP, pWE and pEM which are well known to those skilled in the art. Examples of suitable packaging virus lines for preparing both ecotropic and amphotropic retroviral systems include Crip, Cre, 2 and Am. Retroviruses have been used to introduce a variety of genes into many different cell types, including neuronal cells, in vitro and/or in vivo (see for example Eglitis, et al. (1985) *Science* 230:1395–1398; Danos and Mulligan (1988) *Proc. Natl. Acad. Sci. USA* 85:6460–6464; Wilson et al. (1988) *Proc. Natl. Acad. Sci. USA* 85:3014–3018; Armentano et al. (1990) *Proc. Natl. Acad. Sci. USA* 87:6141–6145; Huber et al. (1991) *Proc. Natl. Acad. Sci. USA* 88:8039–8043; Ferry et al. (1991) *Proc. Natl. Acad. Sci. USA* 88:8377–8381; Chowdhury et al. (1991) *Science* 254:1802–1805; van Beusechem et al. (1992) *Proc. Natl. Acad. Sci. USA* 89:7640–7644; Kay et al. (1992) *Human Gene Therapy* 3:641–647; Dai et al. (1992) *Proc. Natl. Acad. Sci. USA* 89:10892–10895; Hwu et al. (1993) *J. Immunol.* 150:4104–4115; U.S. Pat. No. 4,868,116; U.S. Pat. No. 4,980,286; PCT Application WO 89/07136; PCT Application WO 89/02468; PCT Application WO 89/05345; and PCT Application WO 92/07573).

Furthermore, it has been shown that it is possible to limit the infection spectrum of retroviruses and consequently of retroviral-based vectors, by modifying the viral packaging proteins on the surface of the viral particle (see, for example PCT publications WO93/25234 and WO94/06920). For instance, strategies for the modification of the infection spectrum of retroviral vectors include: coupling antibodies specific for cell surface antigens to the viral env protein (Roux et al. (1989) *PNAS* 86:9079–9083; Julan et al. (1992) *J. Gen Virol* 73:3251–3255; and Goud et al. (1983) *Virology* 163:251–254); or coupling cell surface receptor ligands to the viral env proteins (Neda et al. (1991) *J Biol Chem* 266:14143–14146). Coupling can be in the form of the chemical cross-linking with a protein or other variety (e.g. lactose to convert the env protein to an asialoglycoprotein), as well as by generating fusion proteins (e.g. single-chain antibody/env fusion proteins). This technique, while useful to limit or otherwise direct the infection to certain tissue types, can also be used to convert an ecotropic vector in to an amphotropic vector.

Moreover, use of retroviral gene delivery can be further enhanced by the use of tissue- or cell-specific transcriptional regulatory sequences which control expression of the hedgehog gene of the retroviral vector.

Another viral gene delivery system useful in the present method utilizes adenovirus-derived vectors. The genome of an adenovirus can be manipulated such that it encodes and expresses a gene product of interest but is inactivated in terms of its ability to replicate in a normal lytic viral life cycle. See for example Berkner et al. (1988) *BioTechniques* 6:616; Rosenfeld et al. (1991) *Science* 252:431–434; and Rosenfeld et al. (1992) *Cell* 68:143–155. Suitable adenoviral vectors derived from the adenovirus strain Ad type 5 d1324 or other strains of adenovirus (e.g., Ad2, Ad3, Ad7 etc.) are well known to those skilled in the art. Recombinant adenoviruses can be advantageous in certain circumstances in that they can be used to infect a wide variety of cell types, including peripheral nerve cells. Furthermore, the virus particle is relatively stable and amenable to purification and concentration, and as above, can be modified so as to affect the spectrum of infectivity. Additionally, introduced adenoviral DNA (and foreign DNA contained therein) is not integrated into the genome of a host cell but remains episomal, thereby avoiding potential problems that can occur as a result of insertional mutagenesis in situations where introduced DNA becomes integrated into the host genome (e.g., retroviral DNA). Moreover, the carrying capacity of the adenoviral genome for foreign DNA is large (up to 8 kilobases) relative to other gene delivery vectors (Berkner et al. cited supra; Haj-Ahmand and Graham (1986) *J. Virol.* 57:267). Most replication-defective adenoviral vectors currently in use and therefore favored by the present invention are deleted for all or parts of the viral E1 and E3 genes but retain as much as 80% of the adenoviral genetic material (see, e.g., Jones et al. (1979) *Cell* 16:683; Berkner et al., supra; and Graham et al. in *Methods in Molecular Biology*, E. J. Murray, Ed. (Humana, Clifton, N.J., 1991) vol. 7. pp. 109–127). Expression of the inserted hedgehog gene can be under control of, for example, the E1A promoter, the major late promoter (MLP) and associated leader sequences, the E3 promoter, or exogenously added promoter sequences.

In addition to viral transfer methods, such as those illustrated above, non-viral methods can also be employed to cause expression of a hedgehog polypeptide in the tissue of an animal. Most nonviral methods of gene transfer rely on normal mechanisms used by mammalian cells for the uptake and intracellular transport of macromolecules. In preferred embodiments, non-viral gene delivery systems of the present invention rely on endocytic pathways for the uptake of the hedgehog polypeptide gene by the targeted cell. Exemplary gene delivery systems of this type include liposomal derived systems, poly-lysine conjugates, and artificial viral envelopes.

In clinical settings, the gene delivery systems for the therapeutic hedgehog gene can be introduced into a patient by any of a number of methods, each of which is familiar in the art. For instance, a pharmaceutical preparation of the gene delivery system can be introduced systemically, e.g. by intravenous injection, and specific transduction of the protein in the target cells occurs predominantly from specificity of transfection provided by the gene delivery vehicle, cell-type or tissue-type expression due to the transcriptional regulatory sequences controlling expression of the receptor gene, or a combination thereof In other embodiments, initial delivery of the recombinant gene is more limited with introduction into the animal being quite localized. For example, the gene delivery vehicle can be introduced by catheter (see U.S. Pat. No. 5,328,470) or by stereotactic injection (e.g. Chen et al. (1994) PNAS 91: 3054–3057). A hedgehog expression construct can be delivered in a gene therapy construct to dermal cells by, e.g., electroporation using techniques described, for example, by Dev et al. ((1994) Cancer Treat Rev 20:105–115).

The pharmaceutical preparation of the gene therapy construct can consist essentially of the gene delivery system in an acceptable diluent, or can comprise a slow release matrix in which the gene delivery vehicle is imbedded. Alternatively, where the complete gene delivery system can be produced intact from recombinant cells, e.g. retroviral vectors, the pharmaceutical preparation can comprise one or more cells which produce the gene delivery system.

In yet another embodiment, the hedgehog or ptc therapeutic can be a "gene activation" construct which, by homologous recombination with a genomic DNA, alters the transcriptional regulatory sequences of an endogenous gene. For instance, the gene activation construct can replace the endogenous promoter of a hedgehog gene with a heterologous promoter, e.g., one which causes consitutive expression of the hedgehog gene or which causes inducible expression of the gene under conditions different from the normal expression pattern of the gene. Other genes in the patched signaling pathway can be similarly targeted. A vareity of different formats for the gene activation constructs are available. See, for example, the Transkaryotic Therapies, Inc PCT publications WO93/09222, WO95/31560, WO96/29411, WO95/31560 and WO94/12650.

In preferred embodiments, the nucleotide sequence used as the gene activation construct can be comprised of (1) DNA from some portion of the endogenous hedgehog gene (exon sequence, intron sequence, promoter sequences, etc.) which direct recombination and (2) heterologous transcriptional regulatory sequence(s) which is to be operably linked to the coding sequence for the genomic hedgehog gene upon recombination of the gene activation construct. For use in generating cultures of hedgehog producing cells, the construct may further include a reporter gene to detect the presence of the knockout construct in the cell.

The gene activation construct is inserted into a cell, and integrates with the genomic DNA of the cell in such a position so as to provide the heterologous regulatory sequences in operative association with the native hedgehog gene. Such insertion occurs by homologous recombination, i.e., recombination regions of the activation construct that are homologous to the endogenous hedgehog gene sequence hybridize to the genomic DNA and recombine with the genoric sequences so that the construct is incorporated into the corresponding position of the genomic DNA.

The terms "recombination region" or "targeting sequence" refer to a segment (i.e., a portion) of a gene activation construct having a sequence that is substantially identical to or substantially complementary to a genomic gene sequence, e.g., including 5' flanking sequences of the genomic gene, and can facilitate homologous recombination between the genomic sequence and the targeting transgene construct.

As used herein, the term "replacement region" refers to a portion of a activation construct which becomes integrated into an endogenous chromosomal location following homologous recombination between a recombination region and a genomic sequence.

The heterologous regulatory sequences, e.g., which are provided in the replacement region, can include one or more of a variety elements, including: promoters (such as constitutive or inducible promoters), enhancers, negative regualtory elements, locus control regions, transcription factor binding sites, or combinations thereof. Promoters/enhancers which may be used to control the expression of the targeted gene in vivo include, but are not limited to, the cytomegalovirus (CMV) promoter/enhancer (Karasuyama et al., 1989, J. Exp. Med., 169:13), the human β-actin promoter (Gunning et al. (1987) PNAS 84:4831–4835), the glucocorticoid-inducible promoter present in the mouse mammary tumor virus long terminal repeat (MMTV LTR) (Klessig et al. (1984) Mol. Cell Biol. 4:1354–1362), the long terminal repeat sequences of Moloney murine leukemia virus (MuLV LTR) (Weiss et al. (1985) RNA Tumor Viruses, Cold Spring Harbor Laboratory, Cold Spring Harbor, N.Y.), the SV40 early or late region promoter (Bernoist et al. (1981) Nature 290:304–310; Templeton et al. (1984) Mol. Cell Biol., 4:817; and Sprague et al. (1983) J. Virol., 45:773), the promoter contained in the 3' long terminal repeat of Rous sarcoma virus (RSV) (Yamamoto et al., 1980, Cell, 22:787–797), the herpes simplex virus (HSV) thymidine kinase promoter/enhancer (Wagner et al. (1981) PNAS 82:3567–71), and the herpes simplex virus LAT promoter (Wolfe et al. (1992) Nature Genetics, 1:379–384).

In an exemplary embodiment, portion of the 5' flanking region of the Shh gene are amplified using primers which add restriction sites, to generate the following fragments 5'-gcgcgcttcgaaGCGAGGCAGCCAGCGAGGGAGA GAGCGAGCGGGCGAGCCGGAGCGAG- GAAatcgatgcgcgc (primer 1) (SEQ ID No. 23)

5'-gcgcgcagatctGGGAAAGCGCAAGAGAGAGCG CACACGCACACACCCGCCCGGCG- CACTCGggatccgcgcgc (primer 2) (SEQ ID No. 24)

As illustrated, primer 1 includes a 5' non-coding region of the human Shh gene and is flanked by an AsuII and ClaI restriction sites. Primer 2 includes a portion of 5' the non-coding region immediately 3' to that present in primer 1. The hedgehog gene sequence is flanked by XhoII and BamHI restriction sites. The purified amplimers are cut with each of the enzymes as appropriate.

The vector pCDNA1.1 (Invitrogen) includes a CMV promoter. The plasmid is cut with with AsuII, which cleaves just 3' to the CMV promoter sequence. The AsuII/ClaI fragment of primer 1 is ligated to the AsuII cleavage site of the pcDNA vector. The ClaI/AsuII ligation destroys the AsuII site at the 3' end of a properly inserted primer 1.

The vector is then cut with BamHI, and an XhoII/BamHI fragment of primer 2 is ligated to the BamHI cleavage site. As above, the BamHI/XhoII ligation destroys the BamHI site at the 5' end of a properly inserted primer 2.

Individual colonies are selected, cut with AsuII and BamHI, and the size of the AsuII/BamHI fragment determined. Colonies in which both the primer 1 and primer 2 sequences are correctly inserted are further amplified, an cut with AsuII and BamHI to produce the gene activation construct
cgaagcgaggcagccagcgagg-gagagagcgagcgggcgagccggagc-gaggaaATCGAAGGTTCGAATCCTTC-CCCCACCACCATCACTTTCAAAAGTCCGAAA GAATCTGCTCCCTGCTTGTGTTGGAG-GTCGCTGAGTAGTGCGCGAGTAAAATT-TAAGCTACAACAAGGCAAGGCTTGAC-CGACAATTGCATGAAGAATCTGCTTAGGGTTA GGCGTTTTGCGCTGCTTCGCGATG-TACGGGCCAGATATACGCGTTGACAT-TGATTATTGACTAGTTATTAATAGTAAT-CAATTACGGGGTCATTAGTTCATAGCCCATATAT GGAGTTCCGCGTTACATAACTTACGG-TAAATGGCCCGCCTGGCTGACCGC-CCAACGACCCCGCCCATTGACGT-CAATAATGACGTATGTTCCATAGTAACGC CAATAGGGACTTTCCATTGACGT-CAATGGGTGGACTATTGACGGTAAACT-GCCCACTTGGCAGTACATCAAGTGTAT-CATATGCCAAGTACGCCCCCTATTGACGTCAAT GACGGTAAATGGCCCGCCTGGCATTAT-GCCCAGTACATGACCTTATGGGACTTTC-CTACTTGGCAGTACATCTACGTATTAGT-CATCGCTATTACCATGGTGATGCGGTTTTGGCA GTACATCAATGGGCGTGGATAGCG-GTTTGACTCACGGGGATTTCCAAGTCTC-CACCCCATTGACGTCAATGG-GAGTTTGTTTTGGCACCAAAATCAACGGGACT TTCCAAAATGTCGTAACAACTCCGC-CCCATTGACGCAAATGGGCGGTAGGCGT-GTACGGTGGGAGGTCTATATAAGCA-GAGCTCTCTGGCTAACTAGAGAACCCACTGCTT ACTGGCTTATCGAAATTAATACGACT-CACTATAGGGAGACCCAAGCTTGGTAC-CGAGCTCGGATCgatctgggaaagcg-caagagagagcgcacacgcacacacccgccgcgcgcactcgg. (SEQ ID No. 25)

In this construct, the flanking primer 1 and primer 2 sequences provide the recombination region which permits the insertion of the CMV promoter in front of the coding sequence for the human Shh gene. Other heterologous promoters (or other transcriptional regulatory sequences) can be inserted in a genomic hedgehog gene by a similar method.

In still other embodiments, the replacement region merely deletes a negative transcriptional control element of the native gene, e.g., to activate expression, or ablates a positive control element, e.g., to inhibit expression of the targeted gene.

V. Exemplary ptc Therapeutic Compounds.

In another embodiment, the subject method is carried out using a ptc therapeutic composition. Such compositions can be generated with, for example, compounds which bind to patched and alter its signal transduction activity, compounds which alter the binding and/or enzymatic activity of a protein (e.g., intracellular) involved in patched signal pathway, and compounds which alter the level of expression of a hedgehog protein, a patched protein or a protein involved in the intracellular signal transduction pathway of patched.

The availability of purified and recombinant hedgehog polypeptides facilitates the generation of assay systems which can be used to screen for drugs, such as small organic molecules, which are either agonists or antagonists of the normal cellular function of a hedgehog and/or patched protein, particularly their role in the pathogenesis of peripheral nerve proliferation and/or differentiation. In one embodiment, the assay evaluates the ability of a compound to modulate binding between a hedgehog polypeptide and a hedgehog receptor such as patched. In other embodiments, the assay merely scores for the ability of a test compound to alter the signal transduction acitity of the patched protein. In this manner, a variety of hedgehog and/or ptc therapeutics, both proliferative and anti-proliferative in activity, can be identified. A variety of assay formats will suffice and, in light of the present disclosure, will be comprehended by skilled artisan.

In many drug screening programs which test libraries of compounds and natural extracts, high throughput assays are desirable in order to maximize the number of compounds surveyed in a given period of time. Assays which are performed in cell-free systems, such as may be derived with purified or semi-purified proteins, are often preferred as "primary" screens in that they can be generated to permit rapid development and relatively easy detection of an alteration in a molecular target which is mediated by a test compound. Moreover, the effects of cellular toxicity and/or bioavailability of the test compound can be generally ignored in the in vitro system, the assay instead being focused primarily on the effect of the drug on the molecular target as may be manifest in an alteration of binding affinity with receptor proteins.

Acordingly, in an exemplary screening assay for ptc therapeutics, the compound of interest is contacted with a mixture including a hedgehog receptor protein (e.g., a cell expressing the patched receptor) and a hedgehog protein under conditions in which it is ordinarily capable of binding the hedgehog protein. To the mixture is then added a composition containing a test compound. Detection and quantification of receptor/hedgehog complexes provides a means for determining the test compound's efficacy at inhibiting (or potentiating) complex formation between the receptor protein and the hedgehog polypeptide. The efficacy of the compound can be assessed by generating dose response curves from data obtained using various concentrations of the test compound. Moreover, a control assay can also be performed to provide a baseline for comparison. In the control assay, isolated and purified hedgehog polypeptide is added to the receptor protein, and the formation of receptor/hedgehog complex is quantitated in the absence of the test compound.

In other embodiments, a ptc therapeutic of the present invention is one which disrupts the association of patched with smoothened.

Agonist and antagonists of peripheral nerve maintanence can be distinguished, and the efficacy of the compound can be assessed, by subsequent testing with peripheral nerve cells, e.g., in culture.

In an illustrative embodiment, the polypeptide utilized as a hedgehog receptor can be generated from the patched protein. Accordingly, an exemplary screening assay includes all or a suitable portion of the patched protein which can be obtained from, for example, the human patched gene (GenBank U43148) or other vertebrate sources (see GenBank Accession numbers U40074 for chicken patched and U46155 for mouse patched), as well as from *drosophila* (GenBank Accession number M28999) or other invertebrate sources. The patched protein can be provided in the screening assay as a whole protein (preferably expressed on the surface of a cell), or alternatively as a fragment of the full length protein which binds to hedgehog polypeptides, e.g., as one or both of the substantial extracellular domains (e.g. corresponding to residues Asn120-Ser438 and/or Arg770-Trp1027 of the human patched protein—which are also potential antagonists of hedgehog-dependent signal transduction). For instance, the patched protein can be provided in soluble form, as for example a preparation of one of the extracellular domains, or a preparation of both of the extracellular domains which are covalently connected by an unstructured linker (see, for example, Huston et al. (1988) PNAS 85:4879; and U.S. Pat. No. 5,091,513). In other embodiments, the protein can be provided as part of a liposomal preparation or expressed on the surface of a cell. The patched protein can derived from a recombinant gene, e.g., being ectopically expressed in a heterologous cell. For instance, the protein can be expressed on oocytes, mammalian cells (e.g., COS, CHO, 3T3 or the like), or yeast cell by standard recombinant DNA techniques. These recombinant cells can be used for receptor binding, signal transduction or gene expression assays. Marigo et al. (1996) *Development* 122:1225–1233 illustrates a binding assay of human hedgehog to chick patched protein ectopically expressed in *Xenopus laevis* oocytes. The assay system of Marigo et al. can be adapted to the present drug screening assays. As illustrated in that reference, Shh binds to the patched protein in a selective, saturable, dose-dependent manner, thus demonstrating that patched is a receptor for Shh.

Complex formation between the hedgehog polypeptide and a hedgehog receptor may be detected by a variety of techniques. For instance, modulation of the formation of complexes can be quantitated using, for example, detectably labelled proteins such as radiolabelled, fluorescently labelled, or enzymatically labelled hedgehog polypeptides, by immunoassay, or by chromatographic detection.

Typically, for cell-free assays, it will be desirable to immobilize either the hedgehog receptor or the hedgehog polypeptide to facilitate separation of receptor/hedgehog complexes from uncomplexed forms of one of the proteins, as well as to accommodate automation of the assay. In one embodiment, a fusion protein can be provided which adds a domain that allows the protein to be bound to a matrix. For example, glutathione-S-transferase/receptor (GST/receptor) fusion proteins can be adsorbed onto glutathione sepharose beads (Sigma Chemical, St. Louis, Mo.) or glutathione derivatized microtitre plates, which are then combined with the hedgehog polypeptide, e.g. an $^{35}$S-labeled hedgehog polypeptide, and the test compound and incubated under conditions conducive to complex formation, e.g. at physiological conditions for salt and pH, though slightly more stringent conditions may be desired. Following incubation, the beads are washed to remove any unbound hedgehog polypeptide, and the matrix bead-bound radiolabel determined directly (e.g. beads placed in scintillant), or in the supernatant after the receptor/hedgehog complexes are dissociated. Alternatively, the complexes can be dissociated from the bead, separated by SDS-PAGE gel, and the level of hedgehog polypeptide found in the bead fraction quantitated from the gel using standard electrophoretic techniques.

Other techniques for immobilizing proteins on matrices are also available for use in the subject assay. For instance, soluble portions of the hedgehog receptor protein can be immobilized utilizing conjugation of biotin and streptavidin. For instance, biotinylated receptor molecules can be prepared from biotin-NHS (N-hydroxy-succinimide) using techniques well known in the art (e.g., biotinylation kit, Pierce Chemicals, Rockford, Ill.), and immobilized in the wells of streptavidin-coated 96 well plates (Pierce Chemical). Alternatively, antibodies reactive with the hedgehog receptor but which do not interfere with hedgehog binding can be derivatized to the wells of the plate, and the receptor trapped in the wells by antibody conjugation. As above, preparations of a hedgehog polypeptide and a test compound are incubated in the receptor-presenting wells of the plate, and the amount of receptor/hedgehog complex trapped in the well can be quantitated. Exemplary methods for detecting such complexes, in addition to those described above for the GST-immobilized complexes, include immunodetection of complexes using antibodies reactive with the hedgehog polypeptide, or which are reactive with the receptor protein and compete for binding with the hedgehog polypeptide; as well as enzyme-linked assays which rely on detecting an enzymatic activity associated with the hedgehog polypeptide. In the instance of the latter, the enzyme can be chemically conjugated or provided as a fusion protein with the hedgehog polypeptide. To illustrate, the hedgehog polypeptide can be chemically cross-linked or genetically fused with alkaline phosphatase, and the amount of hedgehog polypeptide trapped in the complex can be assessed with a chromogenic substrate of the enzyme, e.g. paranitrophenylphosphate. Likewise, a fusion protein comprising the hedgehog polypeptide and glutathione-S-transferase can be provided, and complex formation quantitated by detecting the GST activity using 1-chloro-2,4-dinitrobenzene (Habib et al (1974) *J Biol Chem* 249:7130).

For processes which rely on immunodetection for quantitating one of the proteins trapped in the complex, antibodies against the protein, such as the anti-hedgehog antibodies described herein, can be used. Alternatively, the protein to be detected in the complex can be "epitope tagged" in the form of a fusion protein which includes, in addition to the hedgehog polypeptide or hedgehog receptor sequence, a second polypeptide for which antibodies are readily available (e.g. from commercial sources). For instance, the GST fusion proteins described above can also be used for quantification of binding using antibodies against the GST moiety. Other useful epitope tags include myc-epitopes (e.g., see Ellison et al. (1991) *J Biol Chem* 266:21150–21157) which includes a 10-residue sequence from c-myc, as well as the pFLAG system (International Biotechnologies, Inc.) or the pEZZ-protein A system (Pharamacia, N.J.).

Where the desired portion of the hedgehog receptor (or other hedgehog binding molecule) cannot be provided in soluble form, liposomal vesicles can be used to provide manipulatable and isolatable sources of the receptor. For example, both authentic and recombinant forms of the patched protein can be reconstituted in artificial lipid vesicles (e.g. phosphatidylcholine liposomes) or in cell membrane-derived vesicles (see, for example, Bear et al. (1992) *Cell* 68:809–818; Newton et al. (1983) *Biochemistry* 22:6110–6117; and Reber et al. (1987) *J Biol Chem* 262:11369–11374).

In addition to cell-free assays, such as described above, the readily available source of hedgehog proteins provided by the art also facilitates the generation of cell-based assays for identifying small molecule agonists/antagonists and the like. Analogous to the cell-based assays described above for screening combinatorial libraries, cells which are sensitive to hedgehog induction, e.g. patched-expressing cells or other myoblast-derived cells sensitive to hedgehog induction, can be contacted with a hedgehog protein and a test agent of interest, with the assay scoring for anything from simple binding to the cell to modulation in hedgehog inductive responses by the target cell in the presence and absence of the test agent. As with the cell-free assays, agents which produce a statistically significant change in hedgehog activities (either inhibition or potentiation) can be identified.

In other emdodiments, the cell-based assay scores for agents which disrupt association of patched and smoothened proteins, e.g., in the cell surface membrane or liposomal preparation.

In addition to characterizing cells that naturally express the patched protein, cells which have been genetically engineered to ectopically express patched can be utilized for drug screening assays. As an example, cells which either express low levels or lack expression of the patched protein, e.g. *Xenopus laevis* oocytes, COS cells or yeast cells, can be genetically modified using standard techniques to ectopically express the patched protein. (see Marigo et al., supra).

The resulting recombinant cells, e.g., which express a functional patched receptor, can be utilized in receptor binding assays to identify agonist or anatagonsts of hedgehog binding. Binding assays can be performed using whole cells. Furthermore, the recombinant cells of the present invention can be engineered to include other heterolgous genes encoding proteins involved in hedgehog-dependent siganl pathways. For example, the gene products of one or more of smoothened, costal-2 and/or fused can be co-expressed with patched in the reagent cell, with assays being sensitive to the functional reconstituion of the hedgehog signal transduction cascade.

Alternatively, liposomal preparations using reconstituted patched protein can be utilized. Patched protein purified from detergent extracts from both authentic and recombinant origins can be reconstituted in in artificial lipid vesicles (e.g. phosphatidylcholine liposomes) or in cell membrane-derived vesicles (see, for example, Bear et al. (1992) *Cell* 68:809–818; Newton et al. (1983) *Biochemistry* 22:6110–6117; and Reber et al. (1987) *J Biol Chem* 262:11369–11374). The lamellar structure and size of the resulting liposomes can be characterized using electron microscopy. External orientation of the patched protein in the reconstituted membranes can be demonstrated, for example, by immunoelectron microscopy. The hedgehog protein binding activity of liposomes containing patched and liposomes without the protein in the presence of candidate agents can be compared in order to identify potential modulators of the hedgehog-patched interaction.

The hedgehog protein used in these cell-based assays can be provided as a purified source (natural or recombinant in origin), or in the form of cells/tissue which express the protein and which are co-cultured with the target cells. As in the cell-free assays, where simple binding (rather than induction) is the hedgehog activity scored for in the assay, the protein can be labelled by any of the above-mentioned techniques, e.g., fluorescently, enzymatically or radioactively, or detected by immunoassay.

In addition to binding studies, functional assays can be used to identified modulators, i.e., agonists or antagonists, of hedgehog or patched activities. By detecting changes in intracellular signals, such as alterations in second messengers or gene expression, inpatched-expressing cells contacted with a test agent, candidate agonists and antagonists to patched signaling can be identified.

A number of gene products have been implicated in patched-mediated signal transduction, including patched, the transcription factor cubitus interruptus (ci), the serine/threonine kinase fused (fu) and the gene products of costal-2, smoothened and suppressor of fused.

The interaction of a hedgehog protein with patched sets in motion a cascade involving the activation and inhibition of downstream effectors, the ultimate consequence of which is, in some instances, a detectable change in the transcription or translation of a gene. Potential transcriptional targets of patched signaling are the patched gene itself (Hidalgo and Ingham, 1990 *Development* 110, 291–301; Marigo et al., 1996) and the vertebrate homologs of the *drosophila* cubitus interruptus gene, the GLI genes (Hui et al. (1994) *Dev Biol* 162:402413). Patched gene expression has been shown to be induced in cells of the limb bud and the neural plate that are responsive to Shh. (Marigo et al. (1996) *PNAS*, in press; Marigo et al. (1996) *Development* 122:1225–1233). The GLI genes encode putative transcription factors having zinc finger DNA binding domains (Orenic et al. (1990) *Genes & Dev* 4:1053–1067; Kinzler et al. (1990) *Mol Cell Biol* 10:634–642). Transcription of the GLI gene has been reported to be upregulated in response to hedgehog in limb buds, while transcription of the GLI3 gene is downregulated in response to hedgehog induction (Marigo et al. (1996) *Development* 122:1225–1233). By selecting transcriptional regulatory sequences from such target genes, e.g. from patched or GLI genes, that are responsible for the up- or down regulation of these genes in response to patched signalling, and operatively linking such promoters to a reporter gene, one can derive a transcription based assay which is sensitive to the ability of a specific test compound to modify patched signalling pathways. Expression of the reporter gene, thus, provides a valuable screening tool for the development of compounds that act as agonists or antagonists of ptc induction of differentiation/quiescence.

Reporter gene based assays of this invention measure the end stage of the above described cascade of events, e.g., transcriptional modulation. Accordingly, in practicing one embodiment of the assay, a reporter gene construct is inserted into the reagent cell in order to generate a detection signal dependent on ptc signaling. To identify potential regulatory elements responsive to ptc signaling present in the transcriptional regulatory sequence of a target gene, nested deletions of genomic clones of the target gene can be constructed using standard techniques. See, for example, *Current Protocols in Molecular Biology*, Ausubel, F. M. et al. (eds.) Greene Publishing Associates, (1989); U.S. Pat. No. 5,266,488; Sato et al. (1995) *J Biol Chem* 270:10314–10322; and Kube et al. (1995) *Cytokine* 7:1–7. A nested set of DNA fragments from the gene's 5'-flanking region are placed upstream of a reporter gene, such as the luciferase gene, and assayed for their ability to direct reporter gene expression in patched expressing cells. Host cells transiently transfected with reporter gene constructs can be scored for the induction of expression of the reporter gene in the presence and absence of hedgehog to determine regulatory sequences which are responsice to patched-dependent signalling.

In practicing one embodiment of the assay, a reporter gene construct is inserted into the reagent cell in order to generate a detection signal dependent on second messengers generated by induction with hedgehog protein. Typically, the reporter gene construct will include a reporter gene in operative linkage with one or more transcriptional regulatory elements responsive to the hedgehog activity, with the level of expression of the reporter gene providing the hedgehog-dependent detection signal. The amount of transcription from the reporter gene may be measured using any method known to those of skill in the art to be suitable. For example, mRNA expression from the reporter gene may be detected using RNAse protection or RNA-based PCR, or the protein product of the reporter gene may be identified by a characteristic stain or an intrinsic activity. The amount of expression from the reporter gene is then compared to the amount of expression in either the same cell in the absence of the test compound (or hedgehog) or it may be compared with the amount of transcription in a substantially identical cell that lacks the target receptor protein. Any statistically or otherwise significant difference in the amount of transcription indicates that the test compound has in some manner altered the signal transduction of the patched protein, e.g., the test compound is a potential ptc therapeutic.

As described in further detail below, in preferred embodiments the gene product of the reporter is detected by an intrinsic activity associated with that product. For instance, the reporter gene may encode a gene product that, by enzymatic activity, gives rise to a detection signal based on color, fluorescence, or luminescence. In other preferred embodiments, the reporter or marker gene provides a selective growth advantage, e.g., the reporter gene may enhance cell viability, relieve a cell nutritional requirement, and/or provide resistance to a drug.

Preferred reporter genes are those that are readily detectable. The reporter gene may also be included in the construct in the form of a fusion gene with a gene that includes desired transcriptional regulatory sequences or exhibits other desirable properties. Examples of reporter genes include, but are not limited to CAT (chloramphenicol acetyl transferase) (Alton and Vapnek (1979), Nature 282: 864–869) luciferase, and other enzyme detection systems, such as beta-galactosidase; firefly luciferase (deWet et al. (1987), Mol. Cell. Biol. 7:725–737); bacterial luciferase (Engebrecht and Silverman (1984), PNAS 1: 4154–4158; Baldwin et al. (1984), Biochemistry 23: 3663–3667); alkaline phosphatase (Toh et al. (1989) Eur. J. Biochem. 182: 231–238, Hall et al. (1983) J. Mol. Appl. Gen. 2: 101), human placental secreted alkaline phosphatase (Cullen and Malim (1992) Methods in Enzymol. 216:362–368).

Transcriptional control elements which may be included in a reporter gene construct include, but are not limited to, promoters, enhancers, and repressor and activator binding sites. Suitable transcriptional regulatory elements may be derived from the transcriptional regulatory regions of genes whose expression is induced after modulation of a patched signal transduction pathway. The characteristics of preferred genes from which the transcriptional control elements are derived include, but are not limited to, low or undetectable expression in quiescent cells, rapid induction at the transcriptional level within minutes of extracellular simulation, induction that is transient and independent of new protein synthesis, subsequent shut-off of transcription requires new protein synthesis, and mRNAs transcribed from these genes have a short half-life. It is not necessary for all of these properties to be present.

In yet other embodiments, second messenger generation can be measured directly in the detection step, such as mobilization of intracellular calcium, phospholipid metabolism or adenylate cyclase activity are quantitated, for instance, the products of phospholipid hydrolysis $IP_3$, DAG or cAMP could be measured For example, recent studies have implicated protein kinase A (PKA) as a possible component of hedgehog/patched signaling (Hammerschmidt et al. (1996) Genes & Dev 10:647). High PKA activity has been shown to antagonize hedgehog signaling in these systems. Although it is unclear whether PKA acts directly downstream or in parallel with hedgehog signaling, it is possible that hedgehog signalling occurs via inhibition of PKA activity. Thus, detection of PKA activity provides a potential readout for the instant assays.

In a preferred embodiment, the ptc therapeutic is a PKA inhibitor. A variety of PKA inhibitors are known in the art, including both peptidyl and organic compounds. For instance, the ptc therapeutic can be a 5-isoquinolinesulfonamide, such as represented in the general formula:

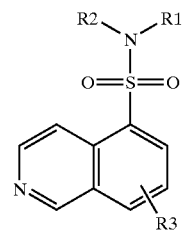

wherein, $R_1$ and $R_2$ each can independently represent hydrogen, and as valence and stability permit a lower alkyl, a lower alkenyl, a lower alkynyl, a carbonyl (such as a carboxyl, an ester, a formate, or a ketone), a thiocarbonyl (such as a thioester, a thioacetate, or a thioformate), an amino, an acylamino, an amido, a cyano, a nitro, an azido, a sulfate, a sulfonate, a sulfonamido, —$(CH_2)_m$—$R_8$, —$(CH_2)_m$—OH, —$(CH_2)_m$—O-lower alkyl, —$(CH_2)_m$—O-lower alkenyl, —$(CH_2)_n$—O—$(CH_2)_m$—$R_8$, —$CH_2)_m$—SH, —$(CH_2)_m$—S-lower alkyl, —$(CH_2)_m$—S-lower alkenyl, —$(CH_2)_n$—S—$(CH_2)_m$—$R_8$, or $R_1$ and $R_2$ taken together with N form a heterocycle (substituted or unsubstituted);

$R_3$ is absent or represents one or more substitutions to the isoquinoline ring such as a lower alkyl, a lower alkenyl, a lower alkynyl, a carbonyl (such as a carboxyl, an ester, a formate, or a ketone), a thiocarbonyl (such as a thioester, a thioacetate, or a thioformate), an amino, an acylamino, an amido, a cyano, a nitro, an azido, a sulfate, a sulfonate, a sulfonamido, —$(CH_2)_m$—$R_8$, —$(CH_2)_m$—OH, —$(CH_2)_m$—O-lower alkyl, —$(CH_2)_m$—O-lower alkenyl, —$(CH_2)_n$—O—$(CH_2)_m$—$R_8$, —$(CH_2)_m$—SH, —$(CH_2)_m$—S-lower alkyl, —$CH_2)_m$—S-lower alkenyl, —$(CH_2)_n$—S—$(CH_2)_m$—$R_8$;

$R_8$ represents a substituted or unsubstituted aryl, aralkyl, cycloalkyl, cycloalkenyl, or heterocycle; and n and m are independently for each occurrence zero or an integer in the range of 1 to 6. In a preferred embodiment, the PKA inhibitor is N-[2-((p-bromocinnamyl)amino)ethyl]-5-isoquinolinesulfonamide(H-89; Calbiochem Cat. No. 371963), e.g., having the formula:

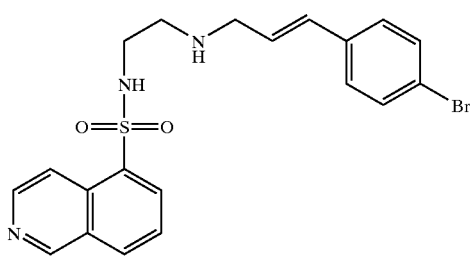

In another embodiment, the PKA inhibitor is 1-(5-isoquinolinesulfonyl)-2-methylpiperazine (H-7; Calbiochem Cat. No. 371955), e.g., having the formula:

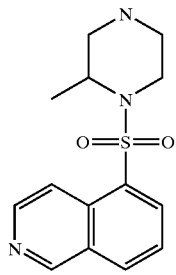

In still other embodiments, the PKA inhibitor is KT5720 (Calbiochem Cat. No. 420315), having the structure

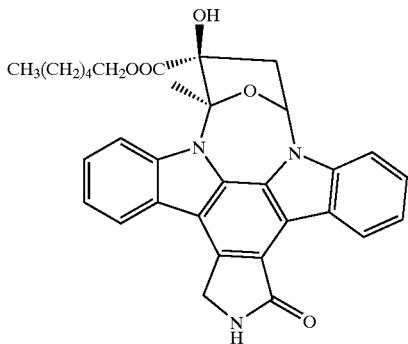

A variety of nucleoside analogs are also useful as PKA inhibitors. For example, the subject method can be carried out cyclic AMP analogs which inhibit the kinase activity of PKA, as for example, 8-bromo-cAMP or dibutyryl-cAMP

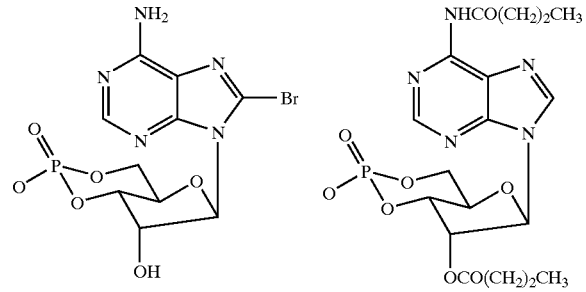

Exemplary peptidyl inhibitors of PKA activity include the PKA Heat Stable Inhibitor (isoform α; see, for example, Calbiochem Cat. No. 539488, and Wen et al. (1995) *J Biol Chem* 270:2041).

Certain hedehog receptors may stimulate the activity of phospholipases. Inositol lipids can be extracted and analyzed using standard lipid extraction techniques. Water soluble derivatives of all three inositol lipids ($IP_1$, $IP_2$, $IP_3$) can also be quantitated using radiolabelling techniques or HPLC.

The mobilization of intracellular calcium or the influx of calcium from outside the cell may be a response to hedgehog stimulation or lack there of. Calcium flux in the reagent cell can be measured using standard techniques. The choice of the appropriate calcium indicator, fluorescent, bioluminescent, metallochromic, or $Ca^{++}$-sensitive microelectrodes depends on the cell type and the magnitude and time constant of the event under study (Borle (1990) *Environ Health Perspect* 84:45–56). As an exemplary method of $Ca^{++}$ detection, cells could be loaded with the $Ca^{++}$ sensitive fluorescent dye fura-2 or indo-1, using standard methods, and any change in $Ca^{++}$ measured using a fluorometer.

In certain embodiments of the assay, it may be desirable to screen for changes in cellular phosphorylation. As an example, the *drosophila* gene fused (fu) which encodes a serine/threonine kinase has been identified as a potential downstream target in hedgehog signaling. (Preat et al., 1990 *Nature* 347, 87–89; Therond et al. 1993, *Mech. Dev.* 44. 65–80). The ability of compounds to modulate serine/threonine kinase activation could be screened using colony immunoblotting (Lyons and Nelson (1984) *Proc. Natl. Acad. Sci. USA* 81:742–7430) using antibodies against phosphorylated serine or threonine residues. Reagents for performing such assays are commercially available, for example, phosphoserine and phosphothreonine specific antibodies which measure increases in phosphorylation of those residues can be purchased from comercial sources.

In yet another embodiment, the ptc therapeutic is an antisense molecule which inhibits expression of a protein involved in a patched-mediated signal transduction pathway. To illustrate, by inhibiting the expression of a protein which are involved in patched signals, such as fused, costal-2, smoothened and/or Gli genes, the ability of the patched signal pathway(s) to inhibit proliferation of a cell can be altered, e.g., potentiated or repressed.

As used herein, "antisense" therapy refers to administration or in situ generation of oligonucleotide probes or their derivatives which specifically hybridize (e.g. bind) under cellular conditions with cellular mRNA and/or genomic DNA encoding a hedgehog protein, patched, or a protein involved in patched-mediated signal transduction. The hybridization should inhibit expression of that protein, e.g. by inhibiting transcription and/or translation. The binding may be by conventional base pair complementarity, or, for example, in the case of binding to DNA duplexes, through specific interactions in the major groove of the double helix. In general, "antisense" therapy refers to the range of techniques generally employed in the art, and includes any therapy which relies on specific binding to oligonucleotide sequences.

An antisense construct of the present invention can be delivered, for example, as an expression plasmid which, when transcribed in the cell, produces RNA which is complementary to at least a unique portion of the target cellular mRNA. Alternatively, the antisense construct is an oligonucleotide probe which is generated ex vivo and which, when introduced into the cell causes inhibition of expression by hybridizing with the mRNA and/or genomic sequences of a target gene. Such oligonucleotide probes are preferably modified oligonucleotide which are resistant to endogenous nucleases, e.g. exonucleases and/or endonucleases, and is therefore stable in vivo. Exemplary nucleic acid molecules for use as antisense oligonucleotides are phosphoramidate, phosphothioate and methylphosphonate analogs of DNA (see also U.S. Pat. Nos. 5,176,996; 5,264,564; and 5,256,775). Additionally, general approaches to constructing oligomers useful in antisense therapy have been reviewed, for example, by Van der Krol et al. (1988) *Biotechniques* 6:958–976; and Stein et al. (1988) *Cancer Res* 48:2659–2668.

Several considerations should be taken into account when constructing antisense oligonucleotides for the use in the methods of the invention: (1) oligos should have a GC content of 50% or more; (2) avoid sequences with stretches of 3 or more G's; and (3) oligonucleotides should not be longer than 25–26 mers. When testing an antisense oligonucleotide, a mismatched control can be constructed. The controls can be generated by reversing the sequence order of the corresponding antisense oligonucleotide in order to conserve the same ratio of bases.

In an illustrative embodiment, the ptc therapeutic can be an antisense construct for inhibiting the expression of patched, e.g., to mimic the inhibition of patched by hedgehog. Exemplary antisense constructs include:

5'-GTCCTGGCGCCGCCGCCGCCGTCGCC (SEQ ID No. 26)
5'-TTCCGATGACCGGCCTTTCGCGGTGA (SEQ ID No. 27)
5'-GTGCACGGAAAGGTGCAGGCCACACT (SEQ ID No. 28)

VI Exemplary Pharmaceutical Preparations of Hedgehog and ptc Therapeutics

The source of the hedgehog and ptc therapeutics to be formulated will depend on the particular form of the agent. Small organic molecules and peptidyl fragments can be chemically synthesized and provided in a pure form suitable for pharmaceutical/cosmetic usage. Products of natural extracts can be purified according to techniques known in the art. For example, the Cox et al. U.S. Pat. No. 5,286,654 describes a method for purifying naturally occurring forms of a secreted protein and can be adapted for purification of hedgehog polypeptides. Recombinant sources of hedgehog polypeptides are also available. For example, the gene encoding hedgehog polypeptides, are known, inter alia, from PCT publications WO 95/18856 and WO 96/17924.

Those of skill in treating peripheral neuropathies can determine the effective amount of an hedgehog or ptc therapeutic to be formulated in a pharmaceutical or cosmetic preparation.

The hedgehog or ptc therapeutic formulations used in the method of the invention are most preferably applied in the form of appropriate compositions. As appropriate compositions there may be cited all compositions usually employed for systemically or topically administering drugs. The pharmaceutically acceptable carrier should be substantially inert, so as not to act with the active component. Suitable inert carriers include water, alcohol polyethylene glycol, mineral oil or petroleum gel, propylene glycol and the like.

To prepare the pharmaceutical compositions of this invention, an effective amount of the particular hedgehog or ptc therapeutic as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, particularly, for administration orally, rectally, percutaneously, or by parenteral injection. For example, in preparing the compositions in oral dosage form, any of the usual pharmaceutical media may be employed such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules, and tablets. Because of their ease in administration, tablets and capsules represents the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Also included are solid form preparations which are intended to be converted, shortly before use, to liquid form preparations. In the compositons suitable for percutaneous administration, the carrier optionally comprises a penetration enhancing agent and/or a suitable wetting agent, optionally combined with suitable additives of any nature in minor proportions, which additives do not introduce a significant deleterious effect on the skin.

In addition to the direct topical application of the preparations they can be topically administered by other methods, for example, encapsulated in a temperature and/or pressure sensitive matrix or in film or solid carrier which is soluble in body fluids and the like for subsequent release, preferably sustained-release of the active component.

As appropriate compositions for topical application there may be cited all compositions usually employed for topically administering therapeuitcs, e.g., creams, gellies, dressings, shampoos, tinctures, pastes, ointments, salves, powders, liquid or semiliquid formulation and the like. Application of said compositions may be by aerosol e.g. with a propellent such as nitrogen carbon dioxide, a freon, or without a propellent such as a pump spray, drops, lotions, or a semisolid such as a thickened composition which can be applied by a swab. In particular compositions, semisolid compositions such as salves, creams, pastes, gellies, ointments and the like will conveniently be used.

It is especially advantageous to formulate the subject compositions in dosage unit form for ease of administration and uniformity of dosage. Dosage unit form as used in the specification and claims herein refers to physically discreate units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powders packets, wafers, injectable solutions or suspensions, teaspoonfuls, tablespoonfuls and the like, and segregated multiples thereof.

The pharmaceutical preparations of the present invention can be used, as stated above, for the many applications whcih can be considered cosmetic uses. Cosmetic compositions known in the art, preferably hypoallergic and pH controlled are especially preferred, and include toilet waters, packs, lotions, skin milks or milky lotions. The preparations contain, besides the hedgehog or ptc therapeutic, components usually employed in such preparations. Examples of such components are oils, fats, waxes, surfactants, humectants, thickening agents, antioxidants, viscosity stabilizers, chelating agents, buffers, preservatives, perfumes, dyestuffs, lower alkanols, and the like. If desired, further ingredients may be incorporated in the compositions, e.g. antiinflammatory agents, antibacterials, antifungals, disinfectants, vitamins, sunscreens, antibiotics, or other anti-acne agents.

Examples of oils comprise fats and oils such as olive oil and hydrogenated oils; waxes such as beeswax and lanolin; hydrocarbons such as liquid paraffin, ceresin, and squalane; fatty acids such as stearic acid and oleic acid; alcohols such as cetyl alcohol, stearyl alcohol, lanolin alcohol, and hexadecanol; and esters such as isopropyl myristate, isopropyl palmitate and butyl stearate. As examples of surfactants there may be cited anionic surfactants such as sodium stearate, sodium cetylsulfate, polyoxyethylene laurylether phosphate, sodium N-acyl glutamate; cationic surfactants such as stearyldimethylbenzylammonium chloride and stearyltrimethylammonium chloride; ampholytic surfactants such as alkylaminoethylglycine hydrocloride solutions and lecithin; and nonionic surfactants such as glycerin monostearate, sorbitan monostearate, sucrose fatty acid esters, propylene glycol monostearate, polyoxyethylene oleylether, polyethylene glycol monostearate, polyoxyethylene sorbitan monopalmitate, polyoxyethylene coconut fatty acid monoethanolamide, polyoxypropylene glycol (e.g. the materials sold under the trademark "Pluronic"), polyoxyethylene castor oil, and polyoxyethylene lanolin. Examples of humectants include glycerin, 1,3-butylene glycol, and propylene glycol; examples of lower alcohols include ethanol and isopropanol; examples of thickening agents include xanthan gum, hydroxypropyl cellulose, hydroxypropyl methyl cellulose, polyethylene glycol and sodium carboxymethyl cellulose; examples of antioxidants comprise butylated hydroxytoluene, butylated hydroxyanisole, propyl gallate, citric acid and ethoxyquin; examples of chelating agents include disodium edetate and ethanehydroxy diphosphate; examples of buffers comprise citric acid, sodium citrate, boric acid, borax, and disodium hydrogen phosphate; and examples of preservatives are methyl parahydroxybenzoate, ethyl parahydroxybenzoate, dehydroacetic acid, salicylic acid and benzoic acid.

For preparing ointments, creams, toilet waters, skin milks, and the like, typically from 0.01 to 10% in particular from 0.1 to 5% and more in particular from 0.2 to 2.5% of the active ingredient, e.g., of the hedgehog or ptc therapeutic, will be incorporated in the compositions. In ointments or creams, the carrier for example consists of 1 to 20%, in particular 5 to 15% of a humectant, 0.1 to 10% in particular from 0.5 to 5% of a thickener and water; or said carrier may consist of 70 to 99%, in particular 20 to 95% of a surfactant, and 0 to 20%, in particular 2.5 to 15% of a fat; or 80 to 99.9% in particular 90 to 99% of a thickener; or 5 to 15% of a surfactant, 2–15% of a humectant, 0 to 80% of an oil, very small (<2%) amounts of preservative, coloring agent and/or perfume, and water. In a toilet water, the carrier for example consists of 2 to 10% of a lower alcohol, 0.1 to 10% or in particular 0.5 to 1% of a surfactant, 1 to 20%, in particular 3 to 7% of a humectant, 0 to 5% of a buffer, water and small amounts (<2%) of preservative, dyestuff and/or perfume. In a skin milk, the carrier typically consists of 10–50% of oil, 1 to 10% of surfactant, 50–80% of water and 0 to 3% of preservative and/or perfume. In the aforementioned preparations, all % symbols refer to weight by weight percentage.

Particular compositions for use in the method of the present invention are those wherein the hedgehog or ptc therapeutic is formulated in liposome-containing compositions. Liposomes are artificial vesicles formed by amphipathic molecules such as polar lipids, for example, phosphatidyl cholines, ethanolamines and serines, sphingomyelins, cardiolipins, plasmalogens, phosphatidic acids and cerebiosides. Liposomes are formed when suitable amphiphathic molecules are allowed to swell in water or aqueous solutions to form liquid crystals usually of multilayer structure comprised of many bilayers separated from each other by aqueous material (also referred to as coarse liposomes). Another type of liposome known to be consisting of a single bilayer encapsulating aqueous material is referred to as a unilamellar vesicle. If water-soluble materials are included in the aqueous phase during the swelling of the lipids they become entrapped in the aqueous layer between the lipid bilayers.

Water-soluble active ingredients such as, for example, various salt forms of a hedgehog polypeptide, are encapsulated in the aqueous spaces between the molecular layers. The lipid soluble active ingredient of hedgehog or ptc therapeutic, such as an organic mimetic, is predominantly incorporated into the lipid layers, although polar head groups may protude from the layer into the aqueous space. The encapsulation of these compounds can be achieved by a number of methods. The method most commonly used involves casting a thin film of phospholipid onto the walls of a flask by evaporation from an organic solvent. When this film is dispersed in a suitable aqueous medium, multilamellar liposomes are formed. Upon suitable sonication, the coarse liposomes form smaller similarly closed vesicles.

Water-soluble active ingredients are usually incorporated by dispersing the cast film with an aqueous solution of the compound. The unencapsulated compound is then removed by centrifugation, chromatography, dialysis or other art-known suitable procedures. The lipid-soluble active ingredient is usually incorporated by dissolving it in the organic solvent with the phospholipid prior to casting the film. If the solubility of the material in the lipid phase is not exceeded or the amount present is not in excess of that which can be bound to the lipid, liposomes prepared by the above method usually contain most of the material bound in the lipid bilayers; separation of the liposomes from unencapsulated material is not required.

A particularly convenient method for preparing liposome formulated forms of hedgehog and ptc therapeutics is the method described in EP-A-253,619, incorporated herein by reference. In this method, single bilayered liposomes containing encapsulated active ingredients are prepared by dissolving the lipid component in an organic medium, injecting the organic solution of the lipid component under pressure into an aqueous component while simultaneously mixing the organic and aqueous components with a high speed homogenizer or mixing means, whereupon the liposomes are formed spontaneously.

The single bilayered liposomes containing the encapsulated hedgehog or ptc therapeutic can be employed directly or they can be employed in a suitable pharmaceutically acceptable carrier for topical administration. The viscosity of the liposomes can be increased by the addition of one or more suitable thickening agents such as, for example xanthan gum, hydroxypropyl cellulose, hydroxypropyl methylcellulose and mixtures thereof. The aqueous component may consist of water alone or it may contain electrolytes, buffered systems and other ingredients, such as, for example, preservatives. Suitable electrolytes which can be employed include metal salts such as alkali metal and alkaline earth metal salts. The preferred metal salts are calcium chloride, sodium chloride and potassium chloride. The concentration of the electrolyte may vary from zero to 260 mM, preferably from 5 mM to 160 mM. The aqueous component is placed in a suitable vessel which can be adapted to effect homogenization by effecting great turbulence during the injection of the organic component. Homogenization of the two components can be accomplished within the vessel, or, alternatively, the aqueous and organic components may be injected separately into a mixing means which is located outside the vessel. In the latter case, the liposomes are formed in the mixing means and then transferred to another vessel for collection purpose.

The organic component consists of a suitable non-toxic, pharmaceutically acceptable solvent such as, for example ethanol, glycerol, propylene glycol and polyethylene glycol, and a suitable phospholipid which is soluble in the solvent. Suitable phospholipids which can be employed include lecithin, phosphatidylcholine, phosphatydylserine, phosphatidylethanol-amine, phosphatidylinositol, lysophosphatidylucholine and phospha-tidyl glycerol, for example. Other lipophilic additives may be employed in order to selectively modify the characteristics of the liposomes. Example s of such other additives include stearylamine, phosphatidic acid, tocopherot, cholesterol and lanolin extracts.

In addition, other ingredients which can prevent oxidation of the phospholipids may be added to the organic component. Examples of such other ingredients include tocopherol, butylated hydroxyanisole, butylated hydroxytoluene, ascorbyl palmitate and ascorbyl oleate. Preservatives such a benzoic acid, methyl paraben and propyl paraben may also be added.

Apart from the above-described compositions, use may be made of covers, e.g. plasters, bandages, dressings, gauze pads and the like, containing an appropriate amount of a hedgehog or ptc therapeutic. In some cases use may be made of plasters, bandages, dressings, gauze pads and the like which have been impregnated with a topical formulation containing the therapeutic formulation.

Exemplification

The invention now being generally described, it will be more readily understood by reference to the following examples which are included merely for purposes of illustration of certain aspects and embodiments of the present invention, and are not intended to limit the invention.

EXAMPLE 1

Evaluation of the Neuroprotective Action Sonic Hedgehog in a Cisplatin-Induced Neuropathy The use of antiviral or anticancer chemotherapy may induce a severe neuropathy, that implies a reduction of the dosage used and hence a risk of unsuccess of the treatment. For example cisplatin is largely used for the treatment of tumors of the bladder, testis or ovary; however the dosage is limited because of the appearance of a partially irreversible toxic neuropathy, with a preference for the sensory fibers of large diameter that modifies the proprioceptive sensitivity (Mollman, 1990). However there is presently no real treatment to cure or prevent such neurotoxicity.

It should be noted that NGF has been shown to be able to limit the importance of neuropathies induced by such chemotherapeutic agents (Apfel et al, 1991, Apfel et al, 1992). Two other peptides (NT3 and an ACTH analog) have also been tested in a similar model (Gao et al, 1995; Hamers et al, 1993). sonic hedge hog has been implicated in antero-posterior patterning of the developing chik limb (Riddle et al, 1993) and in motor neurons differentiation (Roelink et al, 1995). The present study was performed in order to measure the effect of Sonic Hedge Hog (SHH) as protective with regard to cisplatin-induced neuropathy. Behavioral and EMG measurements showed that SHH efficiently protected peripheral neurons against neuropathy, particularly at the highest concentration tested (500 ug/kg).

1) Materials and Methods 1.1) Animals Housing and Treatment

Thirty nine mice were included in this study and divided into 4 groups of 9–10 mice 38–40 g at onset; one group was treated with SHH (50 ug/kg, s.c.) 3 times per week; the second group received a dosage of 500 ug/kg; a third group was a vehicle group. These three groups were also treated with cisplatin (as described below). A fourth group was a control group without cisplatin administration but treated with 500 ug/kg SHH (control 500). Stock solution SHH (2.8 mg/ml) was stored frozen at −70° C.; on the day of use a vial was diluted to 0.2 mg/ml with PBS and protein was mixed gently by pepetting. The animals were housed in plastic cages at room temperature in a 12:12 h light-dark cycle. The mice had free access to food and water.

Animals were weighted once weekly and checked for their general behavior walking attitude and general outlook. Electromyographical and behavioral tests were also performed once weekly.

1.2) Cisplatin Administration

Cisplatin was administered as an aqueous solution (1 mg/ml) at a dosage of 2 mg/kg i.p once daily during 14 consecutive days (cumulative dose). In order to avoid an important loss of weight of the animals, a Ringer-lactate solution was administered daily (0.4 ml/day i.p).

1.3) Behavioral Testing 1.3.1) Pain Threshold Measurement 1.3.1.1) Tail Flick Test The tail of the mouse was placed under a shutter-controlled lamp as a heat source. The latency before the mouse flicked its tail from the heat was recorded. A sensory alteration would increase the latency to flick.

1.3.1.2) Hot Plate Test

The animal was placed inside a glass cylinder of 17 cm height and 9 cm diameter on a hot plate at 52° C. The animal's behavior was observed, particularly the licking of a foot, the jump in the cylinder and the adjusted leap. The latency before licking its foot or before jumping to escape the heat was recorded. If the thermal sensitivity was altered, the time needed to feel the pain would be increased.

1.3.2) Motor Coordination Measurement 1.3.2.1) Rotarod Test

The ability of an animal to stay on a rotating dowel (rotarod) is a good mean to measure the motor coordination and the proprioceptive sensitivity. The apparatus consisted of a rod, 1 cm in diameter, which turned at 12 rpm. The mice were tested for their ability to balance on the rotating bar during 180 sec maximum time (Tilson and Mitchell, 1984).

1.3.2.2) Walk on a Rod

The animals were placed on a rod 1.5 cm in diameter and 40 cm long, that was situated horizontally at 50 cm over the floor; they were placed at one extremity and tended to reach the other end, that consisted of a wooden platform. The time needed to reach the platform was related to the motor coordination: the longest it was, the most important the motor deficit.

1.3.3) Muscle Performance Measurement 1.3.3.1) Muscular Endurance

The muscular strength was evaluated by measuring the ability of an animal to hold a weight of 32 grams when it was lifted by the tail. The animal was allowed to use either two or the four legs. The time during which it held the weight was recorded, with a maximum of 60 sec, and reflected the muscular endurance.

1.3.3.2) Maximal Strength

The maximal muscle strength was measured with an isometric transducer attached to a piece of wire. When the animal held the wire with either two or the four legs, it was slowly moved backwards until it released the wire. The transducer measured the maximal strength; results are given in newton.

1.4) Electrophysiological Measurement

Sensitive Evoked Response: Sensory Nerve Conduction Velocity (SNCV).

Animals were anaesthetized with ketamine chlorhydrate (Ketalar) and diazepam (Valium) (1 ml/kg of a solution containing 11.25 mg ketalar and 0.375 mg of valium; i.p). Electrophysiological recordings were performed using a Neuromatic electromyogram (EMG) apparatus (Dantec, Les Ulis, France). Mice were deeply anaesthetized and normal body temperature maintained with a heating lamp.

The sensitive evoked response was measured in the caudal nerve. Stimulation of the caudal nerve was performed at the base of the tail, with two electrodes (one active, one reference) separated by 3 mm; a unipolar recording needle was placed in a proximal site at approximately 40 mm. Sensory nerve velocity was recorded according to orthodromic conduction (from the tip of tail to the base). A ground needle electrode was inserted between the stimulating and recording electrode needles. The SNCV was calculated according to the distance between the two active electrodes.

1.5) Statistical Studies

The Electrophysiological and behavioral data were statistically analyzed by an analysis of variance with repeated measures (ANOVA). Following these analysis, a Scheffe's post hoc test was used to check for differences between individual groups.

2) Results 2.1) General Survey

Figure 1:
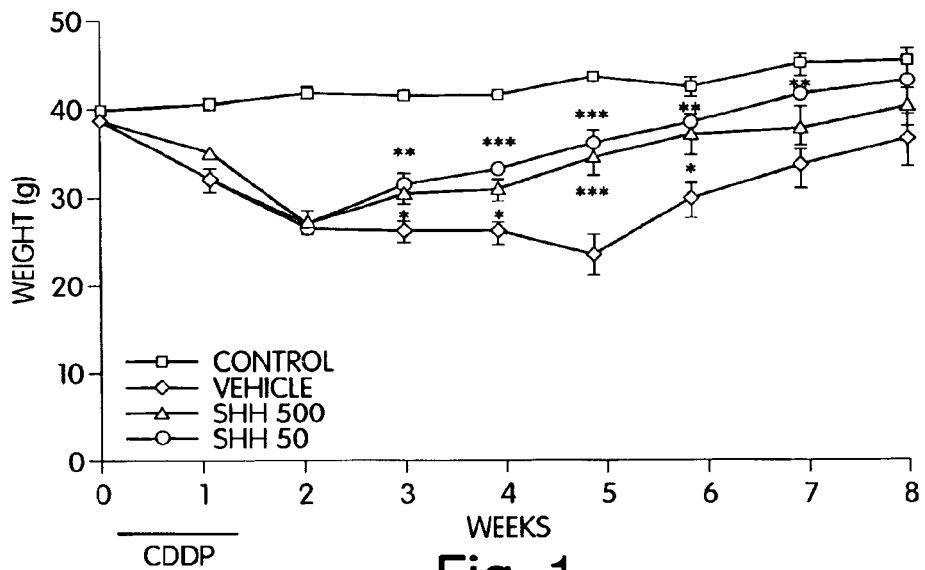
FIG. 1. Variation of the weight of animals during the study in treated or control mice: control SHH=animals treated with 500 ug/kg SHH, without cisplatin; veh=vehicle group treated with cisplatin 2 mg/kg/day during 14 days.

General behavior of animals was normal during the initial 2 weeks of study; however locomotor activity decreased while neuropathy was progressing, hair color changed and finally animals were almost immobile in their cages. Weight decreased strikingly after 2 weeks and remained low in vehicle group until 5 weeks. (FIG. 1; difference between treatments significant at $p<0.0001$; correlation between treatment effect and time changes significant at $p<0.0001$). However weight of animals treated with SHH (at both concentrations) increased immediately after the end of cisplatin administration and was almost normal at the end of study. In vehicle group, weight only started to increase at 5 weeks and was significantly below normal value at the end of study.

As a consequence of cisplatin toxicity, some animals died during the study, starting at 3 weeks. However number of surviving animals was higher in SHH treated group, compare to vehicle (FIG. 2). On the other hand, 3 controlSHH animals died during anaesthesia at 1 and 5 weeks.

1.2) EMG: Sensory Nerve Conduction Velocity (SNCV)

According to EMG measurements, the neuropathy was found to appear after 1 week of cisplatin administration, was maximal at 3 weeks (delayed effect) and recover period went up to 8 weeks.

In standard conditions SNCV varied between 47 and 51 rn/s for mice of 8 weeks of age. After cisplatin administration, SNCV decreased significantly in vehicle and SHH50 groups (FIG. 3; difference between treatments significant at $p<0.0001$; correlation between treatment effect and time changes significant at $p<0.0001$); recovery started immediately after end of cisplatin administration in SHH50 group, but was delayed one week later in vehicle group. Normal SNCV values were recovered after 8 weeks. However no significant decrease was found in SHH500 or control500 groups.

2.3) Behavioral Testing 2.3.1) Pain Threshold Measurement 2.3.1.1) Tail Flick Test Latency to flick the tail was increased after cisplatin administration in vehicle group, with a maximum at 4 weeks (FIG. 4; difference between treatments significant at $p<0.0001$; correlation between treatment effect and time changes significant at $p<0.0002$). A similar tendency was found in SHH50 group, but the curve was always below vehicle, i.e pain threshold defect was less important. In SHH50 group, latency increase was only transiently measured at 3 weeks.

2.3.1.2) Hot Plate Test

The latency before licking the paw did not vary much during the study, except a transient increase in vehicle group at 6 weeks (FIG. 5; difference between treatments not significant; correlation between treatment effect and time changes not significant). It should be noted that a great variation was found at that time and no significant difference was seen.

When pain was more important, mice tried to escape by jumping; the latency before first jump was recorded. It was found to be increased in vehicle group until 7 weeks and in SHH50 until 2 weeks (FIG. 6); the difference between treatments was only statistically significant at 6 weeks because of large variations in vehicle group (time course significant at $p<0.0001$; correlation between treatment effect and time changes not significant). A minor increase in SHH500 group was also measured until 3 weeks; values returned to normal thereafter and they were significantly lower than vehicle at 5 weeks.

After prolonged exposure to heat, mice escaped by jumping onto the rim of cylinder; some increase of the latency to escape was found at 2 weeks (particularly in SHH50 group) without reaching significance (FIG. 7). A greater increase was transiently found in vehicle group after 5 weeks and difference was statistically significant when compared to SHH treated groups (time course significant at $p<0.0001$; correlation between treatment effect and time changes significant at $p<0.0001$).

2.3.2) Motor Coordination Measurement 2.3.2.1) Rotarod Test

The ability of an animal to stay on a rotating rod was found to be significantly decreased in vehicle group, with a minimum performance at 3 weeks (FIG. 8). No decrease was measured in control500 or SHH500 groups and only a transient decrease at 2 weeks in SHH50 group (difference between treatments significant at $p<0.0001$; correlation between treatment effect and time changes significant at $p<0.0072$).

2.3.2.2) Walk on a Rod

The time needed to walk on the rod in order to reach the platform significantly increased in vehicle group at 2 and 5 weeks, but only at 2 weeks in SHH50 group (FIG. 9; difference between treatments significant at $p<0.0015$; correlation between treatment effect and time changes significant at $p<0.0001$). No increase was found in SHH500 group, except at 3 weeks.

2.3.3) Muscle Performance Measurement 2.3.3.1) Muscular Endurance

When mice were allowed to use all 4 limbs to pull the wire, no decrease of muscular endurance was measured, except in vehicle group at 5 weeks (FIG. 10a; difference between treatments not significant; correlation between treatment effect and time changes not significant). When mice were allowed to use only forelimbs to pull the wire, some decrease in muscular endurance was measured in vehicle group, but not in SHH50 or SHH500 groups (FIG. 10b; difference between treatments not significant; correlation between treatment effect and time changes not significant). It should be noted that some decrease was also transiently found in control500 at 4 and 5 weeks.

2.3.3.2) Maximal Strength

The maximal muscle strength exerted by the 4 limbs was decreased after 1–2 weeks in all cisplatin-treated groups (FIG. 11a; time course significant at $p<0.019$; correlation between treatment effect and time changes not significant). Recovery occurred at 5 weeks in SHH50 and SHH500 groups, but only at 7 weeks in vehicle group. No decrease was found in control.

The maximal muscle strength exerted by the forelimbs progressively decreased in vehicle group, with a minimum value at 6 weeks and recovery at 7 weeks (FIG. 11b; difference between treatments significant at $p<0.014$; correlation between treatment effect and time changes significant at $p<0.005$). A transient (and not significant decrease) was found in SHH50 at 2 weeks and no decrease was measured in SHH500 or control500 groups.

3) Discussion

The results obtained in the present study show that SHH was able to protect peripheral nerve against neuropathy induced by cisplatin, particularly at the highest concentration. The most striking effect was observed on SNCV, where no decrease was noticed in SHH500 group. In SHH50 group, SNCV decrease similar to vehicle was measured at 2 weeks; however recovery already began at 3 weeks, i.e one week earlier than in vehicle group. Similarly sensory defect is shown with tail flick test in vehicle group that lasted throughout the study while it was only transient in SHH500 (at 3 weeks). Sensory defect measured on the hot plate (first jump) was found until week 5 in vehicle group and week 2 in SHH50. No significant defect was measured in SHH500 group. Proprioceptive defect is also suggested by rotarod data in vehicle group until week 7 and transiently in SHH50 at week 2. No defect was found in SHH500 group. However these changes may also be related to alteration of motor coordination.

Initial sensory neuropathy is known to extend towards motor impairment in patients treated with cisplatin. Similarly in the present study, muscle performance was impaired in the forelimbs endurance test im vehicle group, but not in any SHH group. Maximal muscle strength exerted by the 5 limbs was decreased in vehicle and both SHH groups, but recovery of function occurred earlier in SHH groups. No such decrease was found in the forelimbs maximal strength test in SHH500 group.

Weight variation is a good indicator of general metabolism of the animals. It decreased strikingly at 2 weeks following cisplatin administration and lasted until week 5 in vehicle group; in both SHH groups recovery occurred immediately after the end of cisplatin administration. Similarly animal survival was improved by SHH treatment.

It is concluded that SHH treatment with 500 ug/kg avoids neuropathy impairment in most tests or accelerates recovery when some defect is measured. Treatment with 50 ug/kg does not protect to the same extent, but also improves recovery (SNCV, jump, rotarod, muscle strength). Difference in time course of recovery is 2 weeks or more, when compared to vehicle group. These effects are similar to those observed with NGF or ACTH analog treatment in a similar paradigm (Apfel et al, 1992; Hamers et al, 1993); recovery of weight loss and SNCV decrease were also observed after end of cisplatin treatment. Dosage of ACTH was similar (75 ug/kg s.c every 48 h), while amount of NGF was 10 times higher (5 mg/kg 3 times per week) and 1 mg/kg had no effect.

It should be noted that naive animals treated with 500 ug/kg SHH (but without cisplatin) did not show any impairment, except in forelimbs endurance. However as mentioned 3 animals of this group died during anaesthesia, at 1 and 5 weeks. Taken together with the absence of other signs of impairment in this group, it is most unprobable that this occurrence may be due to toxicity of prolonged administration of the compound. However a similar study with lower dosage (100 or 200 ug/kg SHH) may be useful.

5) REFERENCES FOR EXAMPLE 1

Apfel S. C, Arezzo J. C, Lipson L. A and Kessler J. A, NGF prevents experimental cisplatin neuropathy, Ann Neurol (1992) 31, 76–80

Apfel S. C Lipton R. B, Arezzo J. C and Kessler J. A, NGF prevents toxic neuropathy in mice, Ann Neurol (1991) 29, 87–90

Gao W Q, Dybdal N, Shinsky N et al, Ann Neurol (1995) 38, 30–37

Hamers F P T, Pette C, Bravenboer B, Vecht C J, Neujt J O and Gispen W H, Cancer Chemother Pharmacol (1993) 32, 162–166

Lipton R. B Apfel S. C and Dutcher J. P, Neurology (1989) 39, 368–373

Mollman J. E, N. England J. Med (1990) 322, 126–127

Riddle R D, Johnson R L, Laufer E and Tabin C, Sonic hedgehog mediates the polarizing activity of the ZPA, Cell 75 (1993) 1401–16.

Roelink H, Porter J A et al, Floor plate and motor neuron induction by different concentrations of the amino-terminal cleavage product of sonic hedgehog autoproteolysis, Cell 81 (1995) 445–55.

Tilson H. A and Mitchell C. L, Neurobehavioral techniques of chemicals on the nervous system, Ann Rev Pharm Toxicol (1984) 24, 425–450.

EXAMPLE 2

Evaluation of Periperhal Nerves in Normal and Transgenic Dhh Knockout Mice

We also undertook a comparison of the electrophysiology and morphology of peripheral nerve cells and bundles in normal mice and in transgenic mice in which the Dhh gene has been disrupted (the "Dhh$^{-/-}$" phenotype).

Adult mice were anesthetized with 0.5 cc of ketamine/xylazine (diluted 1:10 with sterile saline) delivered by i.p. injection. The hair over the hindlimbs was shaved and the legs were taped in an extended position. Their core temperature was maintained at 38° C. with an infrared lamp. A pair of surface recording electrodes were placed on the bottom of each foot; one over the intrinsic plantar muscles, the other more distally. The sciatic nerve was stimulated both proximally (at the level of the L5 vertebrae) and distally (the tibial nerve was stimulated at the ankle) with a pair of subcutaneous electrodes using a Dantec Neuromatic 2000. The stimulus strength was gradually increased until a maximal compound muscle action potential was obtained. The distance between the proximal and distal stimulation sites was measured and used to calculate the motor nerve conduction velocity.

FIG. 12 illustrates that motor neuron conductance velocities are diminished in the Dhh$^{-/-}$ mice, e.g., showing a functional deficit in peripheral nerve of Dhh$^{-/-}$ mice.

The morphology of the peripheral nerve bundles in these mice were also observed (compare FIG. 13A with 13B, and 14A with 14B). The integrity of the epineurial and perineurial sheath was altered in the Dhh$^{-/-}$ mice. In another line of experiments, we tested the ability of Shh and Dhh to alter the proliferation of perineurial cells. Based on BrdU incorporation, both hedgehog proteins were able to increase proliferation of perineurial cells, but Dhh was dramatically more effective.

In addition to suggesting a role for hedgehog gene products in peripheral neuropathies, the observation that hedgehog proteins can induce proliferation of perineurial cells suggests that antagonists of hedgehog activity may be useful in disorders marked by unwanted proliferation of perineurial cells. For instance, localized hypertrophic mononeuropathy (LHM) is a rare foccal neuropathy associated with perineurial cell proliferation due to an undefined stimulus. Perineuriomas. Likewise, in leprous neuropathy, proliferation of perineurial cells can be implicated in the abnormal multi-layered appearance of the perineurium. Antagonists of hedgehog signalling may therefor be useful to inhibit proliferation of perineurial cells in the treatment of such disorders.

EXAMPLE 3

Evaluation of the Neuroprotective Action Sonic Hedgehog in a Taxol-Induced Neuropathy The use of antiviral or anticancer chemotherapy may induce a severe neuropathy, that implies reduction of the dosage used and enhances the risk of unsuccess of the treatment. For example, taxol is used for the treatment of ovarian cancer or melanoma; however the dosage is limited because of the appearance of a sensory toxic neuropathy (Lipton et al. 1989). It should be noted that NGF has been shown to limit the importance of neuropathies induced by such chemotherapeutic agents. The present study was designed to investigate the potency of Shh to protect against taxol-induced neuropathy. As shown in FIGS. 16 and 17, Shh has positive effects on taxol-treated mice, e.g., enhancing their ability to walk the length of a long suspended rod and to stay on a rotating drum (the so-called rotorod). Both are measures of motor ability and coordination.

1) Animals

Sixty four 22–24 g male Swiss mice (IFFA-CREDO, L'Arbresle, France) were used in this study. They were housed in collective cages (4–5 per cage) and maintained in a room with controlled temperature (21–22° C.) and light under a reversed 12–12 light-dark cycle (light on at 7 p.m.), with food and water available ad libitum. All experiments were carried out in accordance with institutional guidelines.

2) Pharmacological Treatment

Taxol (Sigma, l'Isle d'Abeau, France) was diluted in saline using cremophor 10% V/v (Sigma) (20 mg taxol, 1 ml cremophor, 9 ml saline), and administered intraperitoneally (IP) as a volume of 10 ml/kg at the dose of 20 mg/kg once daily during 7 consecutive days. Shh was supplied by Biogen (Cambridge, Mass., USA). Stock solutions Shh (2 mg/ml and 0.2 mg/ml) were stored at −70° C. Shh and vehicle solutions were labeled as A, B or C in order to perform a double-blind study. On the day of use, vials containing Shh or vehicle (A, B or Q were diluted to 1/40 in saline (200 µl sample+7.8 ml saline) and injected as a volume of 10 ml/kg. Shh (50 or 500 µg/kg) or saline was administered subcutaneously (SC) 3 times per week (n=16 mice per group). These 3 groups were also treated with taxol. A fourth group consisting of a control group received cremophor IP and saline SC (n=16). Shh treatment started from the first day of taxol administration on and lasted for 2 weeks.

3) Behavioral Testing

Sensorimotor tests were performed once a week for 3 weeks. These tests were always done one day before electrophysiological (EPG) recordings. Each group was divided in two subgroups (series 1 and 2). Series 1 was tested on Mondays for behavioral tests and on Tuesdays for EPG test, Series 2 was tested on Wednesdays for behavioral tests and on Thursdays for EPG analysis. Behavioral testing was performed on day 0 (baseline, before taxol intoxication), day 7 (after 6 days of taxol injection), and day 14 (6 days after taxol discontinuation). EPG measurements, were performed before taxol intoxication (day 1), on day 8 (one day after the last injection of taxol), and on day 15 (7 days after discontinuing taxol). The first injection of taxol was performed on day 1, immediately after EPG recording.

3.1) Motor Coordination Measurements

Walking test: The apparatus used was a rod of 1.5 cm diameter and 80 cm long, maintained horizontally 40 cm above a table. The rod was graduated starting in the middle (0 cm) towards the two ends (40 cm) allowing to measure the distance walked by the animal.

Animals were tested once each week. Three consecutive trials were performed. For each trial (60 s maximum), each mouse was placed in the middle of the rod and the time needed to walk the 40 cm distance was recorded. Should the animal fall down or be unable to walk the 40 cm distance, 60 s were credited. For each animal, the mean time of the 3 trials was calculated. This time reflects the motor coordination performance.

Rotarod test: The ability of an animal to remain on a rotating rod (rotarod) reflects motor coordination and proprioceptive sensitivity. The apparatus used was a 3 cm diameter automated rod (Bloseb, Paris, France) with 12 rotations per min.

Animals were tested once each week. The mouse was placed on the rotating rod, and the time it remained on rod was recorded (300 s maximum). If the animal falls before 300 s, an additional trial is performed (3 trials maximum).

3.2) Muscular Power

Maximal strength: The maximal muscle strength was measured with an isometric dynamometer connected to a grid. Once the animal was holding the grid with either two or the four paws, it was slowly moved backwards until it released it. The dynamometer measured the maximal strength developed; results are given in N. Two trials per session were performed. The mean of both trials was calculated for each animal.

Muscular endurance: The muscular endurance was evaluated by measuring the time (maximum of 60 s) during which an animal, lifted by the tail, was able to hold a weight of 38 g. The animal was allowed to use either two or the four paws. Two consecutive trials were performed. The mean of both trials was calculated.

3.3) Sensitivity Tests

Tail flick test: The apparatus consisted of a shutter-controlled lamp as a beat source (Bioseb). Each weekly session consisted of two consecutive trials with an interval of about I min and the mean was calculated.

EXAMPLE 4

Evaluation of the Neuroprotective Action Sonic Hedgehog on Spinal Motor Neurons Amyotrophic lateral sclerosis (ALS) is a progressive neurodegenerative disorder primarily involving motoneurons (Ripps and al., 1995). Overexpression of a mutated human superoxide dismustase gene in mice causes a progressive paralytic disease as result of motomeuron loss in lumbar spinal cord (Mohajeri and al., 1998). The SODI-G93A transgenic mouse model, used for preclinical drug studies in ALS (Gurney, 1997; Morrison and al., 1996), is a good model to explore etiological mechanisms and to screen potential therapeutics. The present experiment, the results of which are illustrated in FIGS. 18–21, demonstrate the positive effects of hedgehog treatment on the survival of spinal motorneurons in SOD transgenic mice, a mouse model of ALS.

With intent to complete a study which analyses the effect of SHH by electromyographical and sensorimotor tests on progressive motoneurons degeneration in transgenic mice overexpressing mutant human superoxide dismutase, nervous tissue was harvested and histological studies performed on lumbar spinal cord sections.

1) Animals and Treatment

SOD mice were genotyped by polymerized chain reaction (PCR) amplification of DNA extracted from the tail, 30 days after birth. DNA (10 ng) was added to 50 ml of mix reaction containing MgCl2 and deoxynucleotide triphosphate mixture. The reaction uses primer sequences set b for exon 4 described by Rosen and al. (1993) that hybridize to opposite strands and flank the target DNA sequence that is to be amplified using a GeneAmp PCR 2400 thermal cycler (Perkin-Elmer, USA). The elongation of the primers is catalyzed by Tag DNA Polymerase (Appligene Oncor, France), a heat-stable DNA polymerase. A repetitive series of 30 cycles involving template denaturation (20 seconds at 92° C., primer annealing (20 seconds at 60° C.) and extension of the annealed primers (20 seconds at 72° C.) by Tag DNA Polymerase results in exponential accumulation of a specific DNA fragment. The resulting PCR products were electrophoresed on an 2% agarose gel and visualized with ethidium bromide (Sigma, L'Isle d'Abeau, France).

Twelve transgenic G93A heterozygotes mice (6 males and 6 females) were included in the study and were divided into 2 groups of 6 mice. One group was treated with vehicle and the oilier with SHH at 500 µg/kg of body weight. They were housed in plastic cages and had free access to food and water. The local was maintained at a constant temperature of 22° C. and humidity of 55% under conventional conditions and on a 12 h light/12 h dark photocycle (light on 7 p.m.).

SHH was administered subcutaneously (SC) 3 times per week starting at 60 days of age, until 100 days.

2) Tissue Harvesting and Staining

Mice at 100 days of age were anaesthetized with 60 mg/kg ketamine hydrochloride (Ketalar) and 2 mg/kg diazepam. (Valium). They were perfused transcardially with phosphate-buffered saline (PBS) containing 0.1% heparin (Sigma, L'Isle d'Abeau, France). Then, animals were perfused with 4% paraformaldehyde in PBS until they became rigid. Spinal, cord was harvested and postfixed overnight. Tissue was then placed in 30% sucrose (Sigma, L'Isle d'Abeau, France) at 4° C. until use.

Spinal cord was frozen in cold isopentane (Prolabo, Fontenay-sous-bois, France), embedded with Tissue-tek O.C.T. compound (Miles, USA) and sections (thickness: 30 gm) were made with a cryostat (Leica Jung CM 1800, Rueil-Malmaison, France). The sections were stained with a 0.1% aqueous solution of cresyl violet (Sigma, L'Isle d'Abeau, France) for 30 to 45 seconds and then dehydrated and mounted in Eukitt (0. Kindler GmbH and Co., Freiburg). Only sections from lumbar segment were examined and to avoid the possibility of a given neuron being counted twice in two contiguous sections, only series of one section out of two were collected. Twenty seven to thirty one sections were obtained from a given lumbar segment. Sections were observed using an optical microscope (Nikon, Japan). Results are expressed as the mean number of cells per animal counted in ventral horns on both sides.

3) Statistical Analysis

Values are given as mean±s.e.mean. Differences between control group and SHH 500 group were evaluated by one factor ANOVA test using Statview Student vl.O VF software.

4) Results

FIG. 18 shows that the group treated with SHH at the dose of 500 µg/kg of body weight displayed a greater number of motoneurons than the control group, but difference was not significant [F(1,10)=1.3; N.S.]. It should be noted that in each group, the number of cells counted in the lumbar segment of the spinal cord of 1 mouse was much lower than the others (2Y0 for control group and 1Y0 for SHH 500 group, Table 1) and these mice were from the same littermate. It was therefore suggested to exclude these mice from the analysis. FIG. 19 shows that without Y0 littermate, the number of cells counted was significantly different between control group and SHH 500 group, and that s.e.m. was much smaller. The number of cells in SHH 500 group was 15% higher than in the control group [F(1,8)=13.7; p<0.01].

TABLE 1

Number of cells counted in each group (individual values)

|  | Identification | Sex | Number of cells |
|---|---|---|---|
| Control group | 2W2 | Female | 874 |
|  | 2Y0 | Female | 678 |
|  | 1Z0 | Male | 920 |
|  | 1Z2 | Male | 932 |
|  | 2Z0 | Female | 835 |
|  | 1A0 | Male | 851 |
| SHH 500 group | 2T20 | Female | 1055 |
|  | 2T3 | Female | 928 |
|  | 2T1 | Female | 1007 |
|  | 1U1 | Male | 1111 |
|  | 1U2 | Male | 985 |
|  | 1Y0 | Male | 589 |

In order to further analyze data, motoneurons numbers measured in males and females were analyzed separately. FIG. 20 shows that in males there was no statistical difference between control group and SHH 500 group [F(1,4)=0.0014; N.S.]. However in females, the number of cells counted in SHH 500 group was significantly higher than in the control group [F(1,4)=8.1; p<0.05] as shown in FIG. 21. These data suggest that SHH compound significantly improved motoneurons survival particularly in females mice.

The observation of individual data in control group shows that the number of cells counted in females, even not significantly, was lower than in males (795.7±59.9 vs 901.0±25.2). This difference may be explained by an earlier start of disease in females than in males. It may be interesting to measure the effects of SHH on motoneurons survival at later age and also to check if hormonal treatment may be able to synergies with SHH administration. In addition, it may be important to begin SHH treatment earlier, as data suggest that neuromuscular impairments may already be present at 60 days.

5) References

GURNEY M. E. (1997). *J Neurol Sci*, 152 Suppl 1, S67–73.
MORRISON et al. (1996) *J Comp Neurol*, 373:619–631.
MOHAJERI et al. (1998) *Exp Neurol*, 150:329–336
RIPPS et al. (1995) *Proc Natl Acad Sci USA*, 92:689–693.
ROELINK et al. (1995) *Cell* 81:445–455.
ROSEN et la. (1993) *Nature*, 362:59–62.
TANABE et al. (1995) *Curr. Biol* 5: 651–658.

EXAMPLE 5

Evaluating Actions of Hedgehog Proteins on Galactose Intoxication-Mediated Neuropathies Galactose intoxication is a mean of inducing neuropathy and disrupting neurotrophic support to peripheral nerve cells in rats. Feeding rats diets high in galactose causes morphologic abnormalities in, e.g., Schwann cells and muscle that are accompanied by a neuropathy characterized by axoral atrophy and slowing nerve conduction velocities.

Adapting a methodology set forth in Mizisin et al. (1997) *J. Neuropath Exp Neurol* 56: 1290–1301, the effects of hedgehog treatment on functional and structural disorders in nerves of galactosemic rats can be assessed.

As illustrated in FIG. 23, treatment with Shh can improve nerve conductance in the galactose intoxicated animal.

EXAMPLE 6

Evaluating the Ability of Treatment with Hedgehog Proteins to Protect Against Diabetic Neuropathy In rats, i.p. injections of streptozotocine (STZ) can be used to generate an animal model of diabetic neuropathy. Utilizing such procedures as described in Garrett et al. (1997) *Neurosci. Lett* 222:191–194 the ability of hedgehog treatment to protect STZ-induced neuropathies can be assessed.

Starting in week 0, male Wistar rats (300 g) were made diabetic by injection of streptozotocin (50–55 mg/kg). In week 5, treatment began with either Shh-(rat)Ig (0.3 or 3 mg/kg s.c.) or vehicle. Rats were injected 3 times per week (Monday, Wednesday and Friday) for 5 weeks. In week 10 the conduction velocity of motor neurons and sensory neurons was measured (FIG. 24). In addition, sciatic nerves were removed to assay NGF (Nerve Growth Factor), ErbB2 and NPY levels (FIG. 24). Blood glucose and body weight were also measured at week 10 (FIG. 25).

Treatment with a hedgehog therapeutic caused significant increases in nerve conduction velocity and caused an increase in NGF levels. The hedgehog treatment did not lead to any significant increase in blood glucose level or body weight, demonstrating that the effects of hedgehog treatment on neurons were not caused by an amelioration of the overall conditions of streptozotocin-induced diabetes.

EXAMPLE 7

Evaluating the Effect of Hedgehog Treatment on Nerve Crush Injury

Hedgehog proteins improve functional recovery following sciatic nerve crush injury. Male CD-1 mice (25–30 g) were given a bilateral sciatic nerve crush and monitored daily for functional recovery by assessing their ability to grip a wire mesh with each hindfoot. See FIG. 22. The data are expressed the average number of grip failures for the right and left foot in 10 trials. Mice were treated every other day beginning on the day of nerve crush with either vehicle (control group), pegylated isoleucine-isoleucine sonic hedgehog (Shh-PEG) at a dose of 1 mg/kg s.c. or isoleucine-isoleucine sonic hedgehog murine Ig fusion protein (Shh-Ig) at doses of 1 or 5 mg/kg s.c. The values represent the mean±S.E.M. for 14 mice per group. * $P<0.05$ for all Shh groups compared to vehicle-treated control, Student-Newman-Keuls test.

In another series of experiments, a crushed-nerve model was created in mice by performing a bilateral crush of the sciatic nerve at the mid-thigh level. Functional recovery was measured over the next two weeks using two assays: (1) the ability to grip with hindfeet, and (2) toe spread (FIG. 26). The effects of Shh-(murine)Ig and anti-HH antibody were tested. Shh-(murine)Ig was administered at 0.3 mg/kg or 1 mg/kg. In addition, mice were treated with an anti-hedgehog antibody to determine whether disrupting hedgehog signaling would affect nerve crush regeneration (FIG. 27).

Treatment with Shh-(murine)Ig did cause significant improvement in grip and toe spread, indicating an improvement in nerve crush regeneration. Improvement was most noticeable at earlier timepoints. Treatment with anti-hedgehog antibody significantly slowed nerve crush regeneration, indicating that hedgehog polypeptides have a physiological role in nerve crush regeneration.

The expression of various members of the hedgehog pathway was measured in mice subjected to nerve crush and sham control mice. Expression of components of the hedgehog signaling pathways is stimulated in response to nerve crush. The abundance of Dhh mRNA increased in the nerve both proximal and distal (relative to the spinal cord) to the site of injury 13 days after crush. Quantitative RT-PCR also showed a significant increase in Dhh mRNA after crush FIG. 28). The percentage of cells expressing beta-galactosidase from a Ptc-1 reporter construct also increased significantly after crush (FIG. 29). Ptc-2 and Gli-1 levels also increased in mouse tissues after crush (FIGS. 30 and 31). Dhh, Ptc-1, Ptc-2 and Gli-1 are all components of the hedgehog signaling pathway.

Taken together these results suggest that the nerve crush stimulates production of members of a hedgehog signaling pathway, and that the hedgehog signaling pathway is important for regeneration after the nerve crush.

All of the above-cited references and publications are hereby incorporated by reference.

Equivalents

Those skilled in the art will recognize, or be able to ascertain using no more than routine experimentation, numerous equivalents to the specific polypeptides, nucleic acids, methods, assays and reagents described herein. Such equivalents are considered to be within the scope of this invention.

We claim:

1. A method for treatment or prophylaxis of diabetic neuropathy comprising administering to an animal an amount of a hedgehog polypeptide modified with a lipophilic moiety effective to treat or prophylactically treat diabetic neuropathy, wherein the hedgehog polypeptide comprises an amino acid sequence that a) binds to a naturally occurring patched receptor and promotes hedgehog signal transduction, and b) is designated in one of SEQ ID NO: 10, SEQ ID NO: 13, SEQ ID NO: 14, SEQ ID NO: 15, or an N-terminal autoproteolytic fragment thereof, and wherein said lipophilic modification consists essentially of addition of a lipophilic moiety to the N-terminal amino acid residue.

2. The method of claim 1, wherein the amino acid sequence is sufficient for specific binding of the polypeptide to a patched protein.

3. The method of claim 2, wherein the polypeptide includes residues 24–194 of SEQ ID No:15.

4. The method of claim 2, wherein the hedgehog polypeptide is modified with a sterol moiety.

5. The method of claim 4, wherein the sterol moiety is cholesterol.

6. The method of claim 2, wherein the hedgehog polypeptide is modified with a fatty acid moiety.

7. The method of claim 6, wherein the fatty acid moiety is selected from myristoyl, palmitoyl, stearoyl, or arachidoyl.

8. The method of claim 2, wherein the hedgehog polypeptide is modified with an aromatic hydrocarbon.

9. The method of claim 8, wherein the aromatic hydrocarbon is selected from benzene, perylene, phenanthrene, anthracene, naphthalene, pyrene, chrysene, or naphthacene.

10. The method of claim 2, wherein the hedgehog polypeptide is modified with a C7–C30 alkyl or cycloalkyl.

11. The method of claim 1, wherein the hedgehog polypeptide mimics hedgehog-mediated patched signal transduction by altering the localization, protein-protein binding and/or enzymatic activity of an intracellular protein involved in a patched signal pathway.

12. The method of claim 1, wherein the hedgehog polypeptide alters the level of expression of a hedgehog protein, a patched protein or a protein involved in the intracellular signal transduction pathway of patched.

13. The method of claim 1, which method is part of a protocol for the treatment of an acquired neuropathy.

14. The method of claim 2, wherein the hedgehog polypeptide is a fusion protein.

15. The method of claim 14, wherein the hedgehog polypeptide is a hedgehog/immunoglobulin fusion.

* * * * *

SEQUENCE LISTING

<160> NUMBER OF SEQ ID NOS: 28

<210> SEQ ID NO 1
<211> LENGTH: 1277
<212> TYPE: DNA
<213> ORGANISM: Gallus gallus

<400> SEQUENCE: 1

```
atggtcgaaa tgctgctgtt gacaagaatt ctcttggtgg gcttcatctg cgctcttta      60
gtctcctctg ggctgacttg tggaccaggc aggggcattg gaaaaaggag gcaccccaaa    120
aagctgaccc cgttagccta taagcagttt attcccaatg tggcagagaa gaccctaggg    180
gccagtggaa gatatgaagg gaagatcaca agaaactccg agagatttaa agaactaacc    240
ccaaattaca accctgacat tattttaag gatgaagaga cacgggagc tgacagactg      300
atgactcagc gctgcaagga caagctgaat gccctggcga tctcggtgat gaaccagtgg    360
cccggggtga agctgcgggt gaccgagggc tgggacgagg atggccatca ctccgaggaa    420
tcgctgcact acgagggtcg cgccgtggac atcaccacgt cggatcggga ccgcagcaag    480
tacggaatgc tggcccgcct cgccgtcgag gccggcttcg actgggtcta ctacgagtcc    540
aaggcgcaca tccactgctc cgtcaaagca gaaaactcag tggcagcgaa atcaggaggc    600
tgcttccctg gctcagccac agtgcacctg gagcatggag gcaccaagct ggtgaaggac    660
ctgagccctg ggaccgcgt gctggctgct gacgcggacg gccggctgct ctacagtgac    720
ttcctcacct cctcgaccg gatggacagc tcccgaaagc tcttctacgt catcgagacg    780
cggcagcccc gggcccggct gctactgacg gcggcccacc tgctctttgt ggcccccag    840
cacaaccagt cggaggccac aggtccacc agtggccagg cgctcttcgc cagcaacgtg    900
aagcctggcc aacgtgtcta tgtgctgggc gagggcgggc agcagctgct gccggcgtct    960
gtccacagcg tctcattgcg ggaggaggcg tccggagcct acgcccact accgcccag   1020
ggcaccatcc tcatcaaccg ggtgttggcc tcctgctacg ccgtcatcga ggagcacagt   1080
tgggcccatt gggccttcgc accattccgc ttggctcagg ggctgctggc cgccctctgc   1140
ccagatgggg ccatccctac tgccgccacc accaccactg gcatccattg gtactcacgg   1200
ctcctctacc gcatcggcag ctgggtgctg atggtgacg cgctgcatcc gctgggcatg   1260
gtggcaccgg ccagctg                                                 1277
```

<210> SEQ ID NO 2
<211> LENGTH: 1190
<212> TYPE: DNA
<213> ORGANISM: Mus musculus

<400> SEQUENCE: 2

```
atggctctgc cggccagtct gttgcccctg tgctgcttgg cactcttggc actatctgcc     60
cagagctgcg ggccgggccg aggaccggtt ggccggcggc gttatgtgcg caagcaactt    120
gtgcctctgc tatacaagca gtttgtgccc agtatgcccg agcggaccct gggcgcgagt    180
gggccagcgg aggggagggt aacaagggg tcggagcgct tccgggacct cgtacccaac    240
tacaaccccg acataatctt caaggatgag gagaacagcg cgcagaccg cctgatgaca    300
gagcgttgca aagagcgggt gaacgctcta gccatcgcgg tgatgaacat gtggcccgga    360
gtacgcctac gtgtgactga aggctgggac gaggacggcc accacgcaca ggattcactc    420
cactacgaag gccgtgcctt ggacatcacc acgtctgacc gtgaccgtaa taagtatggt    480
```

-continued

```
ttgttggcgc gcctagctgt ggaagccgga ttcgactggg tctactacga gtcccgcaac      540
cacatccacg tatcggtcaa agctgataac tcactggcgg tccgagccgg aggctgcttt      600
ccgggaaatg ccacggtgcg cttgcggagc ggcgaacgga aggggctgag ggaactacat      660
cgtggtgact gggtactggc cgctgatgca gcgggccgag tggtacccac gccagtgctg      720
ctcttcctgg accgggatct gcagcgccgc gcctcgttcg tggctgtgga gaccgagcgg      780
cctccgcgca aactgttgct cacaccctgg catctggtgt tcgctgctcg cgggccagcg      840
cctgctccag gtgactttgc accggtgttc gcgcgccgct tacgtgctgg cgactcggtg      900
ctggctcccg gcggggacgc gctccagccg gcgcgcgtag cccgcgtggc gcgcgaggaa      960
gccgtgggcg tgttcgcacc gctcactgcg cacgggacgc tgctggtcaa cgacgtcctc     1020
gcctcctgct acgcggttct agagagtcac cagtgggccc accgcgcctt cgccccttg      1080 cggctgctgc acgcgctcgg ggctctgctc cctgggggtg cagtccagcc gactggcatg     1140
cattggtact ctcgcctcct ttaccgcttg gccgaggagt aatgggctg                 1190
```

<210> SEQ ID NO 3
<211> LENGTH: 1281
<212> TYPE: DNA
<213> ORGANISM: Mus musculus

<400> SEQUENCE: 3

```
atgtctcccg cctggctccg gccccgactg cggttctgtc tgttcctgct gctgctgctt       60
ctggtgccgg cggcgggg ctgcgggccg ggccgggtgg tgggcagccg ccggaggccg        120
cctcgcaagc tcgtgcctct tgcctacaag cagttcagcc ccaacgtgcc ggagaagacc      180
ctgggcgcca gcgggcgcta cgaaggcaag atcgcgcgca gctctgagcg cttcaaagag      240 ctcacccccca actacaatcc cgacatcatc ttcaaggacg aggagaacac gggtgccgac      300
cgcctcatga cccagcgctg caaggaccgt ctgaactcac tggccatctc tgtcatgaac      360
cagtggcctg gtgtgaaact gcgggtgacc gaaggccggg atgaagatgg ccatcactca      420
gaggagtctt tacactatga gggccgcgcg gtggatatca ccacctcaga ccgtgaccga      480
aataagtatg gactgctggc gcgcttagca gtggaggccg gcttcgactg ggtgtattac      540
gagtccaagg cccacgtgca ttgctctgtc aagtctgagc attcggccgc tgccaagaca      600
ggtggctgct ttcctgccgg agcccaggtg cgcctagaga acggggagcg tgtggccctg      660
tcagctgtaa agccaggaga ccgggtgctg gccatggggg aggatgggac ccccaccttc      720
agtgatgtgc ttattttcct ggaccgcgag ccaaaccggc tgagagcttt ccaggtcatc      780
gagactcagg atcctccgcg tcggctggcg ctcacgcctg cccacctgct cttcattgcg      840
gacaatcata cagaaccagc agcccacttc cgggccacat ttgccagcca tgtgcaacca      900
ggccaatatg tgctggtatc aggggtacca ggcctccagc ctgctcgggt ggcagctgtc      960
tccacccacg tggcccttgg gtcctatgct cctctcacaa ggcatgggac acttgtggtg     1020
gaggatgtgg tggcctcctg ctttgcagct gtggctgacc accatctggc tcagttggcc     1080
ttctggcccc tgcgactgtt tcccagtttg gcatgggcca gctggacccc aagtgagggt     1140
gttcactcct accctcagat gctctaccgc ctggggcgtc tcttgctaga agagagcacc     1200
ttccatccac tgggcatgtc tggggcagga agctgaaggg actctaacca ctgccctcct     1260
ggaactgctg tgcgtggatc c                                               1281
```

<210> SEQ ID NO 4

<211> LENGTH: 1313
<212> TYPE: DNA
<213> ORGANISM: Mus musculus

<400> SEQUENCE: 4

| | | | | | | |
|---|---|---|---|---|---|---|
| atgctgctgc | tgctggccag | atgttttctg | gtgatccttg | cttcctcgct | gctggtgtgc | 60 |
| cccgggctgg | cctgtgggcc | cggcaggggg | tttggaaaga | ggcggcaccc | caaaaagctg | 120 |
| accccttag | cctacaagca | gtttattccc | aacgtagccg | agaagaccct | aggggccagc | 180 |
| ggcagatatg | aagggaagat | cacaagaaac | tccgaacgat | ttaaggaact | cacccccaat | 240 |
| tacaaccccg | acatcatatt | taaggatgag | gaaaacacgg | gagcagaccg | gctgatgact | 300 |
| cagaggtgca | agacaagtt | aaatgccttg | gccatctctg | tgatgaacca | gtggcctgga | 360 |
| gtgaggctgc | gagtgaccga | gggctgggat | gaggacggcc | atcattcaga | ggagtctcta | 420 |
| cactatgagg | gtcgagcagt | ggacatcacc | acgtccgacc | gggaccgcag | caagtacggc | 480 |
| atgctggctc | gcctggctgt | ggaagcaggt | ttcgactggg | tctactatga | atccaaagct | 540 |
| cacatccact | gttctgtgaa | agcagagaac | tccgtggcgg | ccaaatccgg | cggctgtttc | 600 |
| ccgggatccg | ccaccgtgca | cctggagcag | ggcggcacca | gctggtgaa | ggacttacgt | 660 |
| cccggagacc | gcgtgctggc | ggctgacgac | cagggccggc | tgctgtacag | cgacttcctc | 720 |
| accttcctgg | accgcgacga | aggcgccaag | aaggtcttct | acgtgatcga | gacgctggag | 780 |
| ccgcgcgagc | gcctgctgct | caccgccgcg | cacctgctct | tcgtggcgcc | gcacaacgac | 840 |
| tcggggccca | cgcccgggcc | aagcgcgctc | tttgccagcc | gcgtgcgccc | cgggcagcgc | 900 |
| gtgtacgtgg | tggctgaacg | cggcgggac | cgccggctgc | tgcccgccgc | ggtgcacagc | 960 |
| gtgacgctgc | gagaggagga | ggcgggcgcg | tacgcgccgc | tcacggcgca | cggcaccatt | 1020 |
| ctcatcaacc | gggtgctcgc | ctcgtgctac | gctgtcatcg | aggagcacag | ctgggcacac | 1080 |
| cgggccttcg | cgcctttccg | cctggcgcac | gcgctgctgg | ccgcgctggc | acccgcccgc | 1140 |
| acggacggcg | ggggcggggg | cagcatccct | gcagcgcaat | ctgcaacgga | agcgaggggc | 1200 |
| gcggagccga | ctgcgggcat | ccactggtac | tcgcagctgc | tctaccacat | tggcacctgg | 1260 |
| ctgttggaca | gcgagaccat | gcatcccttg | ggaatggcgg | tcaagtccag | ctg | 1313 |

<210> SEQ ID NO 5
<211> LENGTH: 1256
<212> TYPE: DNA
<213> ORGANISM: Brachydanio rerio

<400> SEQUENCE: 5

| | | | | | | |
|---|---|---|---|---|---|---|
| atgcggcttt | tgacgagagt | gctgctggtg | tctcttctca | ctctgtcctt | ggtggtgtcc | 60 |
| ggactggcct | gcggtcctgg | cagaggctac | ggcagaagaa | gacatccgaa | gaagctgaca | 120 |
| cctctcgcct | acaagcagtt | catacctaat | gtcgcggaga | agaccttagg | ggccagcggc | 180 |
| agatacgagg | gcaagataac | gcgcaattcg | gagagattta | agaacttac | tccaaattac | 240 |
| aatcccgaca | ttatctttaa | ggatgaggag | aacacgggag | cggacaggct | catgacacag | 300 |
| agatgcaaag | acaagctgaa | ctcgctggcc | atctctgtaa | tgaaccactg | gccagggggtt | 360 |
| aagctgcgtg | tgacagaggg | ctgggatgag | gacggtcacc | attttgaaga | atcactccac | 420 |
| tacgagggaa | gagctgttga | tattaccacc | tctgaccgag | acaagagcaa | atacgggaca | 480 |
| ctgtctcgcc | tagctgtgga | ggctggattt | gactgggtct | attacgagtc | caaagcccac | 540 |
| attcattgct | ctgtcaaagc | agaaaattcg | gttgctgcga | atctgggggg | ctgtttccca | 600 |
| ggttcggctc | tggtctcgct | ccaggacgga | ggacagaagg | ccgtgaagga | cctgaacccc | 660 |

-continued

```
ggagacaagg tgctggcggc agacagcgcg ggaaacctgg tgttcagcga cttcatcatg      720
ttcacagacc gagactccac gacgcgacgt gtgttttacg tcatagaaac gcaagaaccc      780
gttgaaaaga tcaccctcac cgccgctcac ctccttttg tcctcgacaa ctcaacggaa       840
gatctccaca ccatgaccgc cgcgtatgcc agcagtgtca gagccggaca aaaggtgatg      900
gttgttgatg atagcggtca gcttaaatct gtcatcgtgc agcggatata cacgaggag       960 cagcggggct cgttcgcacc agtgactgca catgggacca ttgtggtcga cagaatactg     1020
gcgtcctgtt acgccgtaat agaggaccag gggcttgcgc atttggcctt cgcgcccgcc     1080
aggctctatt attacgtgtc atcattcctg tcccccaaaa ctccagcagt cggtccaatg     1140
cgactttaca acaggagggg gtccactggt actccaggct cctgtcatca aatgggaacg     1200
tggcttttgg acagcaacat gcttcatcct ttggggatgt cagtaaactc aagctg        1256
```

<210> SEQ ID NO 6
<211> LENGTH: 1425
<212> TYPE: DNA
<213> ORGANISM: Homo sapiens
<220> FEATURE:
<221> NAME/KEY: modified_base
<222> LOCATION: (1387...1389)
<223> OTHER INFORMATION: n=a, c, g, or t

<400> SEQUENCE: 6

```
atgctgctgc tggcgagatg tctgctgcta gtcctcgtct cctcgctgct ggtatgctcg       60
ggactggcgt gcggaccggg caggggttc gggaagagga ggcaccccaa aaagctgacc       120
cctttagcct acaagcagtt tatccccaat gtggccgaga agaccctagg cgccagcgga      180
aggtatgaag ggaagatctc cagaaactcc gagcgattta aggaactcac ccccaattac      240
aaccccgaca tcatatttaa ggatgaagaa acaccggag cggacaggct gatgactcag       300
aggtgtaagg acaagttgaa cgcttttggcc atctcggtga tgaaccagtg gccaggagtg      360
aaactgcggg tgaccgaggg ctgggacgaa gatggccacc actcagagga gtctctgcac      420
tacgagggcc gcgcagtgga catcaccacg tctgaccgcg accgcagcaa gtacggcatg      480
ctggcccgcc tggcggtgga ggccggcttc gactgggtgt actacgagtc caaggcacat      540
atccactgct cggtgaaagc agagaactcg gtggcggcca atcggggagg ctgcttcccg      600
ggctcggcca cggtgcacct ggagcagggc ggcaccaagc tggtgaagga cctgagcccc      660
ggggaccgcg tgctggcggc ggacgaccag ggccggctgc tctacagcga cttcctcact      720
ttcctggacc gcgacgacgg cgccaagaag gtcttctacg tgatcgagac gcgggagccg      780 cgcgagcgc tgctgctcac cgccgcgcac ctgctctttg tggcgccgca caacgactcg      840
gccaccgggg agcccgaggc gtcctcgggc tcggggccgc cttccggggg cgcactgggg      900
cctcgggcgc tgttcgccag ccgcgtgcgc cgggccagc gcgtgtacgt ggtggccgag      960
cgtgacgggg accgccggct cctgcccgcc gctgtgcaca gcgtgaccct aagcgaggag     1020
gccgcgggcg cctacgcgcc gctcacggcc cagggcacca ttctcatcaa ccgggtgctg     1080
gcctcgtgct acgcggtcat cgaggagcac agctgggcg accgggcctt cgcgcccttc     1140
cgcctggcgc acgcgctcct ggctgcactg gcgcccgcgc gcacggaccg cggcggggac     1200
agcggcggcg gggaccgcgg gggcggcggc ggcagagtag ccctaaccgc tccaggtgct     1260
gccgacgctc cggtgcgggg ggccaccgcg ggcatccact ggtactcgca gctgctctac     1320
caaataggca cctggctcct ggacagcgag gccctgcacc cgctgggcat ggcggtcaag     1380
```

| | |
|---|---:|
| tccagcnnna gccgggggc cggggaggg gcgcgggagg gggcc | 1425 |

<210> SEQ ID NO 7
<211> LENGTH: 1622
<212> TYPE: DNA
<213> ORGANISM: Homo sapiens

<400> SEQUENCE: 7

| | |
|---|---:|
| catcagccca ccaggagacc tcgcccgccg ctcccccggg ctccccggcc atgtctcccg | 60 |
| cccggctccg gccccgactg cacttctgcc tggtcctgtt gctgctgctg gtggtgcccg | 120 |
| cggcatgggg ctgcgggccg ggtcgggtgg tgggcagccg ccggcgaccg ccacgcaaac | 180 |
| tcgtgccgct cgcctacaag cagttcagcc ccaatgtgcc cgagaagacc ctgggcgcca | 240 |
| gcggacgcta tgaaggcaag atcgctcgca gctccgagcg cttcaaggag ctcaccccca | 300 |
| attacaatcc agacatcatc ttcaaggacg aggagaacac aggcgccgac cgcctcatga | 360 |
| cccagcgctg caaggaccgc ctgaactcgc tggctatctc ggtgatgaac cagtggcccg | 420 |
| gtgtgaagct gcgggtgacc gagggctggg acgaggacgg ccaccactca gaggagtccc | 480 |
| tgcattatga gggccgcgcg gtggacatca ccacatcaga ccgcgaccgc aataagtatg | 540 |
| gactgctggc gcgcttggca gtggaggccg gctttgactg ggtgtattac gagtcaaagg | 600 |
| cccacgtgca ttgctccgtc aagtccgagc actcggccgc agccaagacg ggcggctgct | 660 |
| tccctgccgg agcccaggta cgcctggaga gtggggcgcg tgtggccttg tcagccgtga | 720 |
| ggccgggaga ccgtgtgctg gccatggggg aggatgggag ccccaccttc agcgatgtgc | 780 |
| tcatttttcct ggaccgcgag ccccacaggc tgagagcctt ccaggtcatc gagactcagg | 840 |
| acccccacg ccgcctggca ctcacacccg ctcacctgct ctttacggct gacaatcaca | 900 |
| cggagccggc agcccgcttc cgggccacat ttgccagcca cgtgcagcct ggccagtacg | 960 |
| tgctggtggc tggggtgcca ggcctgcagc ctgcccgcgt ggcagctgtc tctacacacg | 1020 |
| tggccctcgg ggcctacgcc ccgctcacaa agcatgggac actggtggtg gaggatgtgg | 1080 |
| tggcatcctg cttcgcggcc gtggctgacc accacctggc tcagttggcc ttctggcccc | 1140 |
| tgagactctt tcacagcttg gcatggggca gctggacccc gggggagggt gtgcattggt | 1200 |
| acccccagct gctctaccgc ctgggcgtc tcctgctaga agagggcagc ttccacccac | 1260 |
| tgggcatgtc cggggcaggg agctgaaagg actccaccgc tgccctcctg gaactgctgt | 1320 |
| actgggtcca gaagcctctc agccaggagg gagctggccc tggaagggac ctgagctggg | 1380 |
| ggacactggc tcctgccatc tcctctgcca tgaagataca ccattgagac ttgactgggc | 1440 |
| aacaccagcg tcccccaccc gcgtcgtggt gtagtcatag agctgcaagc tgagctggcg | 1500 |
| aggggatggt tgttgacccc tctctcctag agaccttgag gctggcacgg cgactcccaa | 1560 |
| ctcagcctgc tctcactacg agttttcata ctctgcctcc cccattggga gggcccattc | 1620 |
| cc | 1622 |

<210> SEQ ID NO 8
<211> LENGTH: 1191
<212> TYPE: DNA
<213> ORGANISM: Homo sapiens

<400> SEQUENCE: 8

| | |
|---|---:|
| atggctctcc tgaccaatct actgcccttg tgctgcttgg cacttctggc gctgccagcc | 60 |
| cagagctgcg gccgggccg ggggccggtt ggccggcgcc gctatgcgcg caagcagctc | 120 |
| gtgccgctac tctacaagca atttgtgccc ggcgtgccag agcggaccct gggcgccagt | 180 |

```
gggccagcgg aggggagggt ggcaaggggc tccgagcgct tccgggacct cgtgcccaac      240
tacaaccccg acatcatctt caaggatgag agaacagtg gagccgaccg cctgatgacc       300
gagcgttgca aggagagggt gaacgctttg gccattgccg tgatgaacat gtggcccgga      360
gtgcgcctac gagtgactga gggctgggac gaggacggcc accacgctca ggattcactc      420
cactacgaag gccgtgcttt ggacatcact acgtctgacc gcgaccgcaa caagtatggg      480
ttgctggcgc gcctcgcagt ggaagccggc ttcgactggg tctactacga gtcccgcaac      540
cacgtccacg tgtcggtcaa agctgataac tcactggcgg tccgggcggg cggctgcttt      600
ccgggaaatg caactgtgcg cctgtggagc ggcgagcgga aagggctgcg ggaactgcac      660
cgcggagact gggttttggc ggccgatgcg tcaggccggg tggtgcccac gccggtgctg      720
ctcttcctgg accgggactt gcagcgccgg gcttcatttg tggctgtgga gaccgagtgg      780
cctccacgca aactgttgct cacgccctgg cacctggtgt ttgccgctcg agggccggcg      840
cccgcgccag gcgactttgc accggtgttc gcgcgccggc tacgcgctgg ggactcggtg      900
ctggcgcccg gcggggatgc gcttcggcca gcgcgcgtgg cccgtgtggc gcggaggaa      960 gccgtgggcg tgttcgcgcc gctcaccgcg cacgggacgc tgctggtgaa cgatgtcctg     1020
gcctcttgct acgcggttct ggagagtcac cagtgggcgc accgcgcttt tgccccttg     1080 agactgctgc acgcgctagg ggcgctgctc cccgcgggg ccgtccagcc gactggcatg      1140
cattggtact ctcggctcct ctaccgctta gcggaggagc tactgggctg a             1191

<210> SEQ ID NO 9
<211> LENGTH: 1251
<212> TYPE: DNA
<213> ORGANISM: Brachydanio rerio

<400> SEQUENCE: 9
atggacgtaa ggctgcatct gaagcaattt gctttactgt gttttatcag cttgcttctg       60
acgccttgtg gattagcctg tggtcctggt agaggttatg gaaaacgaag acacccaaag      120
aaattaaccc cgttggctta caagcaattc atccccaacg ttgctgagaa acgcttgga      180 gccagcggca aatacgaagg caaaatcaca aggaattcag agagatttaa agagctgatt      240
ccgaattata atcccgatat catctttaag gacgaggaaa acacaaacgc tgacaggctg      300
atgaccaagc gctgtaagga caagttaaat tcgttggcca tatccgtcat gaaccactgg      360
cccggcgtga aactgcgcgt cactgaaggc tgggatgagg atggtcacca tttagaagaa      420
tctttgcact atgagggacg ggcagtggac atcactacct cagacaggga taaaagcaag      480
tatgggatgc tatccaggct tgcagtggag gcaggattcg actgggtcta ttatgaatct      540
aaagcccaca tacactgctc tgtcaaagca gaaaattcag tggctgctaa atcaggagga      600 tgtttttcctg gtctggggac ggtgacactt ggtgatggga cgaggaaacc catcaaagat      660
cttaaagtgg gcgaccgggt tttggctgca gacgagaagg gaaatgtctt aataagcgac      720
tttattatgt ttatagacca cgatccgaca acgagaaggc aattcatcgt catcgagacg      780
tcagaacctt tcaccaagct caccctcact gccgcgcacc tagttttcgt tggaaactct      840
tcagcagctt cgggtataac agcaacattt gccagcaacg tgaagcctgg agatacagtt      900
ttagtgtggg aagacacatg cgagagcctc aagagcgtta cagtgaaaag gatttacact      960
gaggagcacg agggctcttt tgcgccagtc accgcgcacg gaaccataat agtggatcag     1020
gtgttggcat cgtgctacgc ggtcattgag aaccacaaat gggcacattg ggcttttgcg     1080
```

-continued

```
aattttcagg aggatggtat ccactggtac tcaaatatgc tgtttcacat cggctcttgg    1200
ctgctggaca gagactcttt ccatccactc gggattttac acttaagttg a             1251
```

<210> SEQ ID NO 10
<211> LENGTH: 425
<212> TYPE: PRT
<213> ORGANISM: Gallus gallus

<400> SEQUENCE: 10

```
Met Val Glu Met Leu Leu Thr Arg Ile Leu Leu Val Gly Phe Ile
 1               5                  10                  15

Cys Ala Leu Leu Val Ser Ser Gly Leu Thr Cys Gly Pro Gly Arg Gly
                20                  25                  30

Ile Gly Lys Arg His Pro Lys Lys Leu Thr Pro Leu Ala Tyr Lys
            35                  40                  45

Gln Phe Ile Pro Asn Val Ala Glu Lys Thr Leu Gly Ala Ser Gly Arg
         50                  55                  60

Tyr Glu Gly Lys Ile Thr Arg Asn Ser Glu Arg Phe Lys Glu Leu Thr
 65                  70                  75                  80

Pro Asn Tyr Asn Pro Asp Ile Ile Phe Lys Asp Glu Glu Asn Thr Gly
                 85                  90                  95

Ala Asp Arg Leu Met Thr Gln Arg Cys Lys Asp Lys Leu Asn Ala Leu
            100                 105                 110

Ala Ile Ser Val Met Asn Gln Trp Pro Gly Val Lys Leu Arg Val Thr
        115                 120                 125

Glu Gly Trp Asp Glu Asp Gly His His Ser Glu Glu Ser Leu His Tyr
130                 135                 140

Glu Gly Arg Ala Val Asp Ile Thr Thr Ser Asp Arg Asp Arg Ser Lys
145                 150                 155                 160

Tyr Gly Met Leu Ala Arg Leu Ala Val Glu Ala Gly Phe Asp Trp Val
                165                 170                 175

Tyr Tyr Glu Ser Lys Ala His Ile His Cys Ser Val Lys Ala Glu Asn
            180                 185                 190

Ser Val Ala Ala Lys Ser Gly Gly Cys Phe Pro Gly Ser Ala Thr Val
        195                 200                 205

His Leu Glu His Gly Gly Thr Lys Leu Val Lys Asp Leu Ser Pro Gly
    210                 215                 220

Asp Arg Val Leu Ala Ala Asp Ala Asp Gly Arg Leu Leu Tyr Ser Asp
225                 230                 235                 240

Phe Leu Thr Phe Leu Asp Arg Met Asp Ser Ser Arg Lys Leu Phe Tyr
                245                 250                 255

Val Ile Glu Thr Arg Gln Pro Arg Ala Arg Leu Leu Leu Thr Ala Ala
            260                 265                 270

His Leu Leu Phe Val Ala Pro Gln His Asn Gln Ser Glu Ala Thr Gly
        275                 280                 285

Ser Thr Ser Gly Gln Ala Leu Phe Ala Ser Asn Val Lys Pro Gly Gln
    290                 295                 300

Arg Val Tyr Val Leu Gly Glu Gly Gly Gln Leu Leu Pro Ala Ser
305                 310                 315                 320

Val His Ser Val Ser Leu Arg Glu Glu Ala Ser Gly Ala Tyr Ala Pro
                325                 330                 335

Leu Thr Ala Gln Gly Thr Ile Leu Ile Asn Arg Val Leu Ala Ser Cys
            340                 345                 350

Tyr Ala Val Ile Glu Glu His Ser Trp Ala His Trp Ala Phe Ala Pro
```

```
                355                 360                 365
Phe Arg Leu Ala Gln Gly Leu Leu Ala Ala Leu Cys Pro Asp Gly Ala
        370                 375                 380
Ile Pro Thr Ala Ala Thr Thr Thr Gly Ile His Trp Tyr Ser Arg
385                 390                 395                 400
Leu Leu Tyr Arg Ile Gly Ser Trp Val Leu Asp Gly Asp Ala Leu His
                405                 410                 415
Pro Leu Gly Met Val Ala Pro Ala Ser
                420                 425

<210> SEQ ID NO 11
<211> LENGTH: 396
<212> TYPE: PRT
<213> ORGANISM: Mus musculus

<400> SEQUENCE: 11

Met Ala Leu Pro Ala Ser Leu Leu Pro Leu Cys Cys Leu Ala Leu Leu
 1               5                  10                  15
Ala Leu Ser Ala Gln Ser Cys Gly Pro Gly Arg Gly Pro Val Gly Arg
                20                  25                  30
Arg Arg Tyr Val Arg Lys Gln Leu Val Pro Leu Leu Tyr Lys Gln Phe
             35                  40                  45
Val Pro Ser Met Pro Glu Arg Thr Leu Gly Ala Ser Gly Pro Ala Glu
     50                  55                  60
Gly Arg Val Thr Arg Gly Ser Glu Arg Phe Arg Asp Leu Val Pro Asn
 65                  70                  75                  80
Tyr Asn Pro Asp Ile Ile Phe Lys Asp Glu Glu Asn Ser Gly Ala Asp
                 85                  90                  95
Arg Leu Met Thr Glu Arg Cys Lys Glu Arg Val Asn Ala Leu Ala Ile
                100                 105                 110
Ala Val Met Asn Met Trp Pro Gly Val Arg Leu Arg Val Thr Glu Gly
            115                 120                 125
Trp Asp Glu Asp Gly His His Ala Gln Asp Ser Leu His Tyr Glu Gly
130                 135                 140
Arg Ala Leu Asp Ile Thr Thr Ser Asp Arg Asp Arg Asn Lys Tyr Gly
145                 150                 155                 160
Leu Leu Ala Arg Leu Ala Val Glu Ala Gly Phe Asp Trp Val Tyr Tyr
                165                 170                 175
Glu Ser Arg Asn His Ile His Val Ser Val Lys Ala Asp Asn Ser Leu
                180                 185                 190
Ala Val Arg Ala Gly Gly Cys Phe Pro Gly Asn Ala Thr Val Arg Leu
            195                 200                 205
Arg Ser Gly Glu Arg Lys Gly Leu Arg Glu Leu His Arg Gly Asp Trp
    210                 215                 220
Val Leu Ala Ala Asp Ala Ala Gly Arg Val Val Pro Thr Pro Val Leu
225                 230                 235                 240
Leu Phe Leu Asp Arg Asp Leu Gln Arg Arg Ala Ser Phe Val Ala Val
                245                 250                 255
Glu Thr Glu Arg Pro Pro Arg Lys Leu Leu Leu Thr Pro Trp His Leu
                260                 265                 270
Val Phe Ala Ala Arg Gly Pro Ala Pro Ala Pro Gly Asp Phe Ala Pro
            275                 280                 285
Val Phe Ala Arg Arg Leu Arg Ala Gly Asp Ser Val Leu Ala Pro Gly
    290                 295                 300
```

```
Gly Asp Ala Leu Gln Pro Ala Arg Val Ala Arg Val Ala Arg Glu Glu
305                 310                 315                 320

Ala Val Gly Val Phe Ala Pro Leu Thr Ala His Gly Thr Leu Leu Val
            325                 330                 335

Asn Asp Val Leu Ala Ser Cys Tyr Ala Val Leu Glu Ser His Gln Trp
            340                 345                 350

Ala His Arg Ala Phe Ala Pro Leu Arg Leu His Ala Leu Gly Ala
            355                 360                 365

Leu Leu Pro Gly Gly Ala Val Gln Pro Thr Gly Met His Trp Tyr Ser
        370                 375                 380

Arg Leu Leu Tyr Arg Leu Ala Glu Glu Leu Met Gly
385                 390                 395
```

<210> SEQ ID NO 12
<211> LENGTH: 411
<212> TYPE: PRT
<213> ORGANISM: Mus musculus

<400> SEQUENCE: 12

```
Met Ser Pro Ala Trp Leu Arg Pro Arg Leu Arg Phe Cys Leu Phe Leu
1               5                   10                  15

Leu Leu Leu Leu Val Pro Ala Ala Arg Gly Cys Gly Pro Gly Arg
            20                  25                  30

Val Val Gly Ser Arg Arg Pro Arg Lys Leu Val Pro Leu Ala
        35                  40                  45

Tyr Lys Gln Phe Ser Pro Asn Val Pro Glu Lys Thr Leu Gly Ala Ser
    50                  55                  60

Gly Arg Tyr Glu Gly Lys Ile Ala Arg Ser Ser Glu Arg Phe Lys Glu
65                  70                  75                  80

Leu Thr Pro Asn Tyr Asn Pro Asp Ile Ile Phe Lys Asp Glu Glu Asn
                85                  90                  95

Thr Gly Ala Asp Arg Leu Met Thr Gln Arg Cys Lys Asp Arg Leu Asn
            100                 105                 110

Ser Leu Ala Ile Ser Val Met Asn Gln Trp Pro Gly Val Lys Leu Arg
        115                 120                 125

Val Thr Glu Gly Arg Asp Glu Asp Gly His His Ser Glu Glu Ser Leu
130                 135                 140

His Tyr Glu Gly Arg Ala Val Asp Ile Thr Thr Ser Asp Arg Asp Arg
145                 150                 155                 160

Asn Lys Tyr Gly Leu Leu Ala Arg Leu Ala Val Glu Ala Gly Phe Asp
                165                 170                 175

Trp Val Tyr Tyr Glu Ser Lys Ala His Val His Cys Ser Val Lys Ser
            180                 185                 190

Glu His Ser Ala Ala Lys Thr Gly Gly Cys Phe Pro Ala Gly Ala
        195                 200                 205

Gln Val Arg Leu Glu Asn Gly Glu Arg Val Ala Leu Ser Ala Val Lys
    210                 215                 220

Pro Gly Asp Arg Val Leu Ala Met Gly Glu Asp Gly Thr Pro Thr Phe
225                 230                 235                 240

Ser Asp Val Leu Ile Phe Leu Asp Arg Glu Pro Asn Arg Leu Arg Ala
                245                 250                 255

Phe Gln Val Ile Glu Thr Gln Asp Pro Pro Arg Arg Leu Ala Leu Thr
            260                 265                 270

Pro Ala His Leu Leu Phe Ile Ala Asp Asn His Thr Glu Pro Ala Ala
        275                 280                 285
```

```
His Phe Arg Ala Thr Phe Ala Ser His Val Gln Pro Gly Gln Tyr Val
    290                 295                 300
Leu Val Ser Gly Val Pro Gly Leu Gln Pro Ala Arg Val Ala Ala Val
305                 310                 315                 320
Ser Thr His Val Ala Leu Gly Ser Tyr Ala Pro Leu Thr Arg His Gly
                325                 330                 335
Thr Leu Val Val Glu Asp Val Val Ala Ser Cys Phe Ala Ala Val Ala
                340                 345                 350
Asp His His Leu Ala Gln Leu Ala Phe Trp Pro Leu Arg Leu Phe Pro
                355                 360                 365
Ser Leu Ala Trp Gly Ser Trp Thr Pro Ser Glu Gly Val His Ser Tyr
    370                 375                 380
Pro Gln Met Leu Tyr Arg Leu Gly Arg Leu Leu Glu Glu Ser Thr
385                 390                 395                 400
Phe His Pro Leu Gly Met Ser Gly Ala Gly Ser
                405                 410

<210> SEQ ID NO 13
<211> LENGTH: 437
<212> TYPE: PRT
<213> ORGANISM: Mus musculus

<400> SEQUENCE: 13

Met Leu Leu Leu Leu Ala Arg Cys Phe Leu Val Ile Leu Ala Ser Ser
  1               5                  10                  15
Leu Leu Val Cys Pro Gly Leu Ala Cys Gly Pro Gly Arg Gly Phe Gly
                 20                  25                  30
Lys Arg Arg His Pro Lys Lys Leu Thr Pro Leu Ala Tyr Lys Gln Phe
             35                  40                  45
Ile Pro Asn Val Ala Glu Lys Thr Leu Gly Ala Ser Gly Arg Tyr Glu
         50                  55                  60
Gly Lys Ile Thr Arg Asn Ser Glu Arg Phe Lys Glu Leu Thr Pro Asn
 65                  70                  75                  80
Tyr Asn Pro Asp Ile Ile Phe Lys Asp Glu Glu Asn Thr Gly Ala Asp
                 85                  90                  95
Arg Leu Met Thr Gln Arg Cys Lys Asp Lys Leu Asn Ala Leu Ala Ile
            100                 105                 110
Ser Val Met Asn Gln Trp Pro Gly Val Arg Leu Arg Val Thr Glu Gly
        115                 120                 125
Trp Asp Glu Asp Gly His His Ser Glu Glu Ser Leu His Tyr Glu Gly
130                 135                 140
Arg Ala Val Asp Ile Thr Thr Ser Asp Arg Asp Arg Ser Lys Tyr Gly
145                 150                 155                 160
Met Leu Ala Arg Leu Ala Val Glu Ala Gly Phe Asp Trp Val Tyr Tyr
                165                 170                 175
Glu Ser Lys Ala His Ile His Cys Ser Val Lys Ala Glu Asn Ser Val
            180                 185                 190
Ala Ala Lys Ser Gly Gly Cys Phe Pro Gly Ser Ala Thr Val His Leu
        195                 200                 205
Glu Gln Gly Gly Thr Lys Leu Val Lys Asp Leu Arg Pro Gly Asp Arg
    210                 215                 220
Val Leu Ala Ala Asp Asp Gln Gly Arg Leu Leu Tyr Ser Asp Phe Leu
225                 230                 235                 240
Thr Phe Leu Asp Arg Asp Glu Gly Ala Lys Lys Val Phe Tyr Val Ile
```

```
                     245                 250                 255
Glu Thr Leu Glu Pro Arg Glu Arg Leu Leu Thr Ala Ala His Leu
                260                 265                 270

Leu Phe Val Ala Pro His Asn Asp Ser Gly Pro Thr Pro Gly Pro Ser
            275                 280                 285

Ala Leu Phe Ala Ser Arg Val Arg Pro Gly Gln Arg Val Tyr Val Val
        290                 295                 300

Ala Glu Arg Gly Gly Asp Arg Arg Leu Leu Pro Ala Ala Val His Ser
305                 310                 315                 320

Val Thr Leu Arg Glu Glu Ala Gly Ala Tyr Ala Pro Leu Thr Ala
                325                 330                 335

His Gly Thr Ile Leu Ile Asn Arg Val Leu Ala Ser Cys Tyr Ala Val
                340                 345                 350

Ile Glu Glu His Ser Trp Ala His Arg Ala Phe Ala Pro Phe Arg Leu
                355                 360                 365

Ala His Ala Leu Leu Ala Ala Leu Ala Pro Ala Arg Thr Asp Gly Gly
        370                 375                 380

Gly Gly Gly Ser Ile Pro Ala Ala Gln Ser Ala Thr Glu Ala Arg Gly
385                 390                 395                 400

Ala Glu Pro Thr Ala Gly Ile His Trp Tyr Ser Gln Leu Leu Tyr His
                405                 410                 415

Ile Gly Thr Trp Leu Leu Asp Ser Glu Thr Met His Pro Leu Gly Met
                420                 425                 430

Ala Val Lys Ser Ser
            435

<210> SEQ ID NO 14
<211> LENGTH: 418
<212> TYPE: PRT
<213> ORGANISM: Brachydanio rerio

<400> SEQUENCE: 14

Met Arg Leu Leu Thr Arg Val Leu Leu Val Ser Leu Leu Thr Leu Ser
 1               5                  10                  15

Leu Val Val Ser Gly Leu Ala Cys Gly Pro Gly Arg Gly Tyr Gly Arg
                20                  25                  30

Arg Arg His Pro Lys Lys Leu Thr Pro Leu Ala Tyr Lys Gln Phe Ile
            35                  40                  45

Pro Asn Val Ala Glu Lys Thr Leu Gly Ala Ser Gly Arg Tyr Glu Gly
        50                  55                  60

Lys Ile Thr Arg Asn Ser Glu Arg Phe Lys Glu Leu Thr Pro Asn Tyr
65                  70                  75                  80

Asn Pro Asp Ile Ile Phe Lys Asp Glu Glu Asn Thr Gly Ala Asp Arg
                85                  90                  95

Leu Met Thr Gln Arg Cys Lys Asp Lys Leu Asn Ser Leu Ala Ile Ser
                100                 105                 110

Val Met Asn His Trp Pro Gly Val Lys Leu Arg Val Thr Glu Gly Trp
            115                 120                 125

Asp Glu Asp Gly His His Phe Glu Glu Ser Leu His Tyr Glu Gly Arg
        130                 135                 140

Ala Val Asp Ile Thr Thr Ser Asp Arg Asp Lys Ser Lys Tyr Gly Thr
145                 150                 155                 160

Leu Ser Arg Leu Ala Val Glu Ala Gly Phe Asp Trp Val Tyr Tyr Glu
                165                 170                 175
```

-continued

```
Ser Lys Ala His Ile His Cys Ser Val Lys Ala Glu Asn Ser Val Ala
            180                 185                 190

Ala Lys Ser Gly Gly Cys Phe Pro Gly Ser Ala Leu Val Ser Leu Gln
        195                 200                 205

Asp Gly Gly Gln Lys Ala Val Lys Asp Leu Asn Pro Gly Asp Lys Val
    210                 215                 220

Leu Ala Ala Asp Ser Ala Gly Asn Leu Val Phe Ser Asp Phe Ile Met
225                 230                 235                 240

Phe Thr Asp Arg Asp Ser Thr Thr Arg Arg Val Phe Tyr Val Ile Glu
                245                 250                 255

Thr Gln Glu Pro Val Glu Lys Ile Thr Leu Thr Ala Ala His Leu Leu
            260                 265                 270

Phe Val Leu Asp Asn Ser Thr Glu Asp Leu His Thr Met Thr Ala Ala
        275                 280                 285

Tyr Ala Ser Ser Val Arg Ala Gly Gln Lys Val Met Val Val Asp Asp
    290                 295                 300

Ser Gly Gln Leu Lys Ser Val Ile Val Gln Arg Ile Tyr Thr Glu Glu
305                 310                 315                 320

Gln Arg Gly Ser Phe Ala Pro Val Thr Ala His Gly Thr Ile Val Val
                325                 330                 335

Asp Arg Ile Leu Ala Ser Cys Tyr Ala Val Ile Glu Asp Gln Gly Leu
            340                 345                 350

Ala His Leu Ala Phe Ala Pro Ala Arg Leu Tyr Tyr Tyr Val Ser Ser
        355                 360                 365

Phe Leu Ser Pro Lys Thr Pro Ala Val Gly Pro Met Arg Leu Tyr Asn
    370                 375                 380

Arg Arg Gly Ser Thr Gly Thr Pro Gly Ser Cys His Gln Met Gly Thr
385                 390                 395                 400

Trp Leu Leu Asp Ser Asn Met Leu His Pro Leu Gly Met Ser Val Asn
                405                 410                 415

Ser Ser
```

<210> SEQ ID NO 15
<211> LENGTH: 475
<212> TYPE: PRT
<213> ORGANISM: Homo sapiens
<220> FEATURE:
<221> NAME/KEY: SITE
<222> LOCATION: (463)
<223> OTHER INFORMATION: Xaa=unknown amino acid residue

<400> SEQUENCE: 15

```
Met Leu Leu Leu Ala Arg Cys Leu Leu Leu Val Leu Val Ser Ser Leu
  1               5                  10                  15

Leu Val Cys Ser Gly Leu Ala Cys Gly Pro Gly Arg Gly Phe Gly Lys
                 20                  25                  30

Arg Arg His Pro Lys Lys Leu Thr Pro Leu Ala Tyr Lys Gln Phe Ile
             35                  40                  45

Pro Asn Val Ala Glu Lys Thr Leu Gly Ala Ser Gly Arg Tyr Glu Gly
         50                  55                  60

Lys Ile Ser Arg Asn Ser Glu Arg Phe Lys Glu Leu Thr Pro Asn Tyr
 65                  70                  75                  80

Asn Pro Asp Ile Ile Phe Lys Asp Glu Glu Asn Thr Gly Ala Asp Arg
                 85                  90                  95

Leu Met Thr Gln Arg Cys Lys Asp Lys Leu Asn Ala Leu Ala Ile Ser
            100                 105                 110
```

```
Val Met Asn Gln Trp Pro Gly Val Lys Leu Arg Val Thr Glu Gly Trp
    115                 120                 125
Asp Glu Asp Gly His His Ser Glu Glu Ser Leu His Tyr Glu Gly Arg
130                 135                 140
Ala Val Asp Ile Thr Thr Ser Asp Arg Asp Ser Lys Tyr Gly Met
145                 150                 155                 160
Leu Ala Arg Leu Ala Val Glu Ala Gly Phe Asp Trp Val Tyr Tyr Glu
                165                 170                 175
Ser Lys Ala His Ile His Cys Ser Val Lys Ala Glu Asn Ser Val Ala
            180                 185                 190
Ala Lys Ser Gly Gly Cys Phe Pro Gly Ser Ala Thr Val His Leu Glu
        195                 200                 205
Gln Gly Gly Thr Lys Leu Val Lys Asp Leu Ser Pro Gly Asp Arg Val
    210                 215                 220
Leu Ala Ala Asp Asp Gln Gly Arg Leu Leu Tyr Ser Asp Phe Leu Thr
225                 230                 235                 240
Phe Leu Asp Arg Asp Asp Gly Ala Lys Lys Val Phe Tyr Val Ile Glu
                245                 250                 255
Thr Arg Glu Pro Arg Glu Arg Leu Leu Leu Thr Ala Ala His Leu Leu
            260                 265                 270
Phe Val Ala Pro His Asn Asp Ser Ala Thr Gly Glu Pro Glu Ala Ser
        275                 280                 285
Ser Gly Ser Gly Pro Pro Ser Gly Gly Ala Leu Gly Pro Arg Ala Leu
    290                 295                 300
Phe Ala Ser Arg Val Arg Pro Gly Gln Arg Val Tyr Val Val Ala Glu
305                 310                 315                 320
Arg Asp Gly Asp Arg Arg Leu Leu Pro Ala Ala Val His Ser Val Thr
                325                 330                 335
Leu Ser Glu Glu Ala Ala Gly Ala Tyr Ala Pro Leu Thr Ala Gln Gly
            340                 345                 350
Thr Ile Leu Ile Asn Arg Val Leu Ala Ser Cys Tyr Ala Val Ile Glu
        355                 360                 365
Glu His Ser Trp Ala His Arg Ala Phe Ala Pro Phe Arg Leu Ala His
    370                 375                 380
Ala Leu Leu Ala Ala Leu Ala Pro Ala Arg Thr Asp Arg Gly Gly Asp
385                 390                 395                 400
Ser Gly Gly Gly Asp Arg Gly Gly Gly Gly Arg Val Ala Leu Thr
                405                 410                 415
Ala Pro Gly Ala Ala Asp Ala Pro Gly Ala Gly Ala Thr Ala Gly Ile
                420                 425                 430
His Trp Tyr Ser Gln Leu Leu Tyr Gln Ile Gly Thr Trp Leu Leu Asp
            435                 440                 445
Ser Glu Ala Leu His Pro Leu Gly Met Ala Val Lys Ser Ser Xaa Ser
    450                 455                 460
Arg Gly Ala Gly Gly Gly Ala Arg Glu Gly Ala
465                 470                 475

<210> SEQ ID NO 16
<211> LENGTH: 411
<212> TYPE: PRT
<213> ORGANISM: Homo sapiens

<400> SEQUENCE: 16

Met Ser Pro Ala Arg Leu Arg Pro Arg Leu His Phe Cys Leu Val Leu
```

-continued

```
  1               5               10              15
Leu Leu Leu Leu Val Val Pro Ala Ala Trp Gly Cys Gly Pro Gly Arg
                20                  25                  30

Val Val Gly Ser Arg Arg Pro Arg Lys Leu Val Pro Leu Ala
        35                  40                  45

Tyr Lys Gln Phe Ser Pro Asn Val Pro Glu Lys Thr Leu Gly Ala Ser
                50                  55                  60

Gly Arg Tyr Glu Gly Lys Ile Ala Arg Ser Ser Glu Arg Phe Lys Glu
65                  70                  75                  80

Leu Thr Pro Asn Tyr Asn Pro Asp Ile Ile Phe Lys Asp Glu Glu Asn
                85                  90                  95

Thr Gly Ala Asp Arg Leu Met Thr Gln Arg Cys Lys Asp Arg Leu Asn
                100                 105                 110

Ser Leu Ala Ile Ser Val Met Asn Gln Trp Pro Gly Val Lys Leu Arg
                115                 120                 125

Val Thr Glu Gly Trp Asp Glu Asp Gly His His Ser Glu Glu Ser Leu
                130                 135                 140

His Tyr Glu Gly Arg Ala Val Asp Ile Thr Thr Ser Asp Arg Asp Arg
145                 150                 155                 160

Asn Lys Tyr Gly Leu Leu Ala Arg Leu Ala Val Glu Ala Gly Phe Asp
                165                 170                 175

Trp Val Tyr Tyr Glu Ser Lys Ala His Val His Cys Ser Val Lys Ser
                180                 185                 190

Glu His Ser Ala Ala Lys Thr Gly Gly Cys Phe Pro Ala Gly Ala
                195                 200                 205

Gln Val Arg Leu Glu Ser Gly Ala Arg Val Ala Leu Ser Ala Val Arg
                210                 215                 220

Pro Gly Asp Arg Val Leu Ala Met Gly Glu Asp Gly Ser Pro Thr Phe
225                 230                 235                 240

Ser Asp Val Leu Ile Phe Leu Asp Arg Glu Pro His Arg Leu Arg Ala
                245                 250                 255

Phe Gln Val Ile Glu Thr Gln Asp Pro Pro Arg Arg Leu Ala Leu Thr
                260                 265                 270

Pro Ala His Leu Leu Phe Thr Ala Asp Asn His Thr Glu Pro Ala Ala
                275                 280                 285

Arg Phe Arg Ala Thr Phe Ala Ser His Val Gln Pro Gly Gln Tyr Val
                290                 295                 300

Leu Val Ala Gly Val Pro Gly Leu Gln Pro Ala Arg Val Ala Ala Val
305                 310                 315                 320

Ser Thr His Val Ala Leu Gly Ala Tyr Ala Pro Leu Thr Lys His Gly
                325                 330                 335

Thr Leu Val Val Glu Asp Val Val Ala Ser Cys Phe Ala Ala Val Ala
                340                 345                 350

Asp His His Leu Ala Gln Leu Ala Phe Trp Pro Leu Arg Leu Phe His
                355                 360                 365

Ser Leu Ala Trp Gly Ser Trp Thr Pro Gly Glu Gly Val His Trp Tyr
370                 375                 380

Pro Gln Leu Leu Tyr Arg Leu Gly Arg Leu Leu Glu Glu Gly Ser
385                 390                 395                 400

Phe His Pro Leu Gly Met Ser Gly Ala Gly Ser
                405                 410
```

<210> SEQ ID NO 17

-continued

```
<211> LENGTH: 396
<212> TYPE: PRT
<213> ORGANISM: Homo sapiens

<400> SEQUENCE: 17

Met Ala Leu Leu Thr Asn Leu Leu Pro Leu Cys Cys Leu Ala Leu Leu
 1               5                  10                  15

Ala Leu Pro Ala Gln Ser Cys Gly Pro Gly Arg Gly Pro Val Gly Arg
            20                  25                  30

Arg Tyr Ala Arg Lys Gln Leu Val Pro Leu Leu Tyr Lys Gln Phe
        35                  40                  45

Val Pro Gly Val Pro Glu Arg Thr Leu Gly Ala Ser Gly Pro Ala Glu
    50                  55                  60

Gly Arg Val Ala Arg Gly Ser Glu Arg Phe Arg Asp Leu Val Pro Asn
65                  70                  75                  80

Tyr Asn Pro Asp Ile Ile Phe Lys Asp Glu Glu Asn Ser Gly Ala Asp
                85                  90                  95

Arg Leu Met Thr Glu Arg Cys Lys Glu Arg Val Asn Ala Leu Ala Ile
            100                 105                 110

Ala Val Met Asn Met Trp Pro Gly Val Arg Leu Arg Val Thr Glu Gly
        115                 120                 125

Trp Asp Glu Asp Gly His His Ala Gln Asp Ser Leu His Tyr Glu Gly
    130                 135                 140

Arg Ala Leu Asp Ile Thr Thr Ser Asp Arg Asp Arg Asn Lys Tyr Gly
145                 150                 155                 160

Leu Leu Ala Arg Leu Ala Val Glu Ala Gly Phe Asp Trp Val Tyr Tyr
                165                 170                 175

Glu Ser Arg Asn His Val His Val Ser Val Lys Ala Asp Asn Ser Leu
            180                 185                 190

Ala Val Arg Ala Gly Gly Cys Phe Pro Gly Asn Ala Thr Val Arg Leu
        195                 200                 205

Trp Ser Gly Glu Arg Lys Gly Leu Arg Glu Leu His Arg Gly Asp Trp
    210                 215                 220

Val Leu Ala Ala Asp Ala Ser Gly Arg Val Val Pro Thr Pro Val Leu
225                 230                 235                 240

Leu Phe Leu Asp Arg Asp Leu Gln Arg Arg Ala Ser Phe Val Ala Val
                245                 250                 255

Glu Thr Glu Trp Pro Pro Arg Lys Leu Leu Leu Thr Pro Trp His Leu
            260                 265                 270

Val Phe Ala Ala Arg Gly Pro Ala Pro Ala Pro Gly Asp Phe Ala Pro
        275                 280                 285

Val Phe Ala Arg Arg Leu Arg Ala Gly Asp Ser Val Leu Ala Pro Gly
    290                 295                 300

Gly Asp Ala Leu Arg Pro Ala Arg Val Ala Arg Val Ala Arg Glu Glu
305                 310                 315                 320

Ala Val Gly Val Phe Ala Pro Leu Thr Ala His Gly Thr Leu Leu Val
                325                 330                 335

Asn Asp Val Leu Ala Ser Cys Tyr Ala Val Leu Glu Ser His Gln Trp
            340                 345                 350

Ala His Arg Ala Phe Ala Pro Leu Arg Leu Leu His Ala Leu Gly Ala
        355                 360                 365

Leu Leu Pro Gly Gly Ala Val Gln Pro Thr Gly Met His Trp Tyr Ser
    370                 375                 380

Arg Leu Leu Tyr Arg Leu Ala Glu Glu Leu Leu Gly
```

```
385                 390                 395
```

<210> SEQ ID NO 18
<211> LENGTH: 416
<212> TYPE: PRT
<213> ORGANISM: Brachydanio rerio

<400> SEQUENCE: 18

```
Met Asp Val Arg Leu His Leu Lys Gln Phe Ala Leu Leu Cys Phe Ile
 1               5                   10                  15

Ser Leu Leu Thr Pro Cys Gly Leu Ala Cys Gly Pro Gly Arg Gly
            20                  25                  30

Tyr Gly Lys Arg Arg His Pro Lys Lys Leu Thr Pro Leu Ala Tyr Lys
            35                  40                  45

Gln Phe Ile Pro Asn Val Ala Glu Lys Thr Leu Gly Ala Ser Gly Lys
    50                  55                  60

Tyr Glu Gly Lys Ile Thr Arg Asn Ser Glu Arg Phe Lys Glu Leu Ile
 65                  70                  75                  80

Pro Asn Tyr Asn Pro Asp Ile Ile Phe Lys Asp Glu Glu Asn Thr Asn
                85                  90                  95

Ala Asp Arg Leu Met Thr Lys Arg Cys Lys Asp Lys Leu Asn Ser Leu
            100                 105                 110

Ala Ile Ser Val Met Asn His Trp Pro Gly Val Lys Leu Arg Val Thr
            115                 120                 125

Glu Gly Trp Asp Glu Asp Gly His His Leu Glu Glu Ser Leu His Tyr
            130                 135                 140

Glu Gly Arg Ala Val Asp Ile Thr Thr Ser Asp Arg Asp Lys Ser Lys
145                 150                 155                 160

Tyr Gly Met Leu Ser Arg Leu Ala Val Glu Ala Gly Phe Asp Trp Val
                165                 170                 175

Tyr Tyr Glu Ser Lys Ala His Ile His Cys Ser Val Lys Ala Glu Asn
            180                 185                 190

Ser Val Ala Ala Lys Ser Gly Gly Cys Phe Pro Gly Ser Gly Thr Val
            195                 200                 205

Thr Leu Gly Asp Gly Thr Arg Lys Pro Ile Lys Asp Leu Lys Val Gly
    210                 215                 220

Asp Arg Val Leu Ala Ala Asp Glu Lys Gly Asn Val Leu Ile Ser Asp
225                 230                 235                 240

Phe Ile Met Phe Ile Asp His Asp Pro Thr Thr Arg Arg Gln Phe Ile
                245                 250                 255

Val Ile Glu Thr Ser Glu Pro Phe Thr Lys Leu Thr Leu Thr Ala Ala
            260                 265                 270

His Leu Val Phe Val Gly Asn Ser Ala Ala Ser Gly Ile Thr Ala
            275                 280                 285

Thr Phe Ala Ser Asn Val Lys Pro Gly Asp Thr Val Leu Val Trp Glu
    290                 295                 300

Asp Thr Cys Glu Ser Leu Lys Ser Val Thr Val Lys Arg Ile Tyr Thr
305                 310                 315                 320

Glu Glu His Glu Gly Ser Phe Ala Pro Val Thr Ala His Gly Thr Ile
                325                 330                 335

Ile Val Asp Gln Val Leu Ala Ser Cys Tyr Ala Val Ile Glu Asn His
            340                 345                 350

Lys Trp Ala His Trp Ala Phe Ala Pro Val Arg Leu Cys His Lys Leu
            355                 360                 365
```

-continued

```
Met Thr Trp Leu Phe Pro Ala Arg Glu Ser Asn Val Asn Phe Gln Glu
        370                 375                 380

Asp Gly Ile His Trp Tyr Ser Asn Met Leu Phe His Ile Gly Ser Trp
385                 390                 395                 400

Leu Leu Asp Arg Asp Ser Phe His Pro Leu Gly Ile Leu His Leu Ser
                405                 410                 415

<210> SEQ ID NO 19
<211> LENGTH: 1416
<212> TYPE: DNA
<213> ORGANISM: Drosophila melanogaster
<220> FEATURE:
<221> NAME/KEY: CDS
<222> LOCATION: (1)..(1413)

<400> SEQUENCE: 19 atg gat aac cac agc tca gtg cct tgg gcc agt gcc gcc agt gtc acc      48
Met Asp Asn His Ser Ser Val Pro Trp Ala Ser Ala Ala Ser Val Thr
  1               5                  10                  15 tgt ctc tcc ctg gga tgc caa atg cca cag ttc cag ttc cag ttc cag      96
Cys Leu Ser Leu Gly Cys Gln Met Pro Gln Phe Gln Phe Gln Phe Gln
             20                  25                  30 ctc caa atc cgc agc gag ctc cat ctc cgc aag ccc gca aga aga acg     144
Leu Gln Ile Arg Ser Glu Leu His Leu Arg Lys Pro Ala Arg Arg Thr
         35                  40                  45 caa acg atg cgc cac att gcg cat acg cag cgt tgc ctc agc agg ctg     192
Gln Thr Met Arg His Ile Ala His Thr Gln Arg Cys Leu Ser Arg Leu
     50                  55                  60 acc tct ctg gtg gcc ctg ctg ctg atc gtc ttg ccg atg gtc ttt agc     240
Thr Ser Leu Val Ala Leu Leu Leu Ile Val Leu Pro Met Val Phe Ser
 65                  70                  75                  80 ccg gct cac agc tgc ggt cct ggc cga gga ttg ggt cgt cat agg gcg     288
Pro Ala His Ser Cys Gly Pro Gly Arg Gly Leu Gly Arg His Arg Ala
                 85                  90                  95 cgc aac ctg tat ccg ctg gtc ctc aag cag aca att ccc aat cta tcc     336
Arg Asn Leu Tyr Pro Leu Val Leu Lys Gln Thr Ile Pro Asn Leu Ser
            100                 105                 110 gag tac acg aac agc gcc tcc gga cct ctg gag ggt gtg atc cgt cgg     384
Glu Tyr Thr Asn Ser Ala Ser Gly Pro Leu Glu Gly Val Ile Arg Arg
        115                 120                 125 gat tcg ccc aaa ttc aag gac ctc gtg ccc aac tac aac agg gac atc     432
Asp Ser Pro Lys Phe Lys Asp Leu Val Pro Asn Tyr Asn Arg Asp Ile
    130                 135                 140 ctt ttc cgt gac gag gaa ggc acc gga gcg gat ggc ttg atg agc aag     480
Leu Phe Arg Asp Glu Glu Gly Thr Gly Ala Asp Gly Leu Met Ser Lys
145                 150                 155                 160 cgc tgc aag gag aag cta aac gtg ctg gcc tac tcg gtg atg aac gaa     528
Arg Cys Lys Glu Lys Leu Asn Val Leu Ala Tyr Ser Val Met Asn Glu
                165                 170                 175 tgg ccc ggc atc cgg ctg ctg gtc acc gag agc tgg gac gag gac tac     576
Trp Pro Gly Ile Arg Leu Leu Val Thr Glu Ser Trp Asp Glu Asp Tyr
            180                 185                 190 cat cac ggc cag gag tcg ctc cac tac gag ggc cga gcg gtg acc att     624
His His Gly Gln Glu Ser Leu His Tyr Glu Gly Arg Ala Val Thr Ile
        195                 200                 205 gcc acc tcc gat cgc gac cag tcc aaa tac ggc atg ctc gct cgc ctg     672
Ala Thr Ser Asp Arg Asp Gln Ser Lys Tyr Gly Met Leu Ala Arg Leu
    210                 215                 220 gcc gtc gag gct gga ttc gat tgg gtc tcc tac gtc agc agg cgc cac     720
Ala Val Glu Ala Gly Phe Asp Trp Val Ser Tyr Val Ser Arg Arg His
225                 230                 235                 240
```

```
atc tac tgc tcc gtc aag tca gat tcg tcg atc agt tcc cac gtg cac    768
Ile Tyr Cys Ser Val Lys Ser Asp Ser Ser Ile Ser Ser His Val His
            245                 250                 255 ggc tgc ttc acg ccg gag agc aca gcg ctg ctg gag agt gga gtc cgg    816
Gly Cys Phe Thr Pro Glu Ser Thr Ala Leu Leu Glu Ser Gly Val Arg
        260                 265                 270 aag ccg ctc ggc gag ctc tct atc gga gat cgt gtt ttg agc atg acc    864
Lys Pro Leu Gly Glu Leu Ser Ile Gly Asp Arg Val Leu Ser Met Thr
    275                 280                 285 gcc aac gga cag gcc gtc tac agc gaa gtg atc ctc ttc atg gac cgc    912
Ala Asn Gly Gln Ala Val Tyr Ser Glu Val Ile Leu Phe Met Asp Arg
290                 295                 300 aac ctc gag cag atg caa aac ttt gtg cag ctg cac acg gac ggt gga    960
Asn Leu Glu Gln Met Gln Asn Phe Val Gln Leu His Thr Asp Gly Gly
305                 310                 315                 320 gca gtg ctc acg gtg acg ccg gct cac ctg gtt agc gtt tgg cag ccg    1008
Ala Val Leu Thr Val Thr Pro Ala His Leu Val Ser Val Trp Gln Pro
                325                 330                 335 gag agc cag aag ctc acg ttt gtg ttt gcg cat cgc atc gag gag aag    1056
Glu Ser Gln Lys Leu Thr Phe Val Phe Ala His Arg Ile Glu Glu Lys
            340                 345                 350 aac cag gtg ctc gta cgg gat gtg gag acg ggc gag ctg agg ccc cag    1104
Asn Gln Val Leu Val Arg Asp Val Glu Thr Gly Glu Leu Arg Pro Gln
        355                 360                 365 cga gtg gtc aag ttg ggc agt gtg cgc agt aag ggc gtg gtc gcg ccg    1152
Arg Val Val Lys Leu Gly Ser Val Arg Ser Lys Gly Val Val Ala Pro
    370                 375                 380 ctg acc cgc gag ggc acc att gtg gtc aac tcg gtg gcc gcc agt tgc    1200
Leu Thr Arg Glu Gly Thr Ile Val Val Asn Ser Val Ala Ala Ser Cys
385                 390                 395                 400 tat gcg gtg atc aac agt cag tcg ctg gcc cac tgg gga ctg gct ccc    1248
Tyr Ala Val Ile Asn Ser Gln Ser Leu Ala His Trp Gly Leu Ala Pro
                405                 410                 415 atg cgc ctg ctg tcc acg ctg gag gcg tgg ctg ccc gcc aag gag cag    1296
Met Arg Leu Leu Ser Thr Leu Glu Ala Trp Leu Pro Ala Lys Glu Gln
            420                 425                 430 ttg cac agt tcg ccg aag gtg gtg agc tcg gcg cag cag cag aat ggc    1344
Leu His Ser Ser Pro Lys Val Val Ser Ser Ala Gln Gln Gln Asn Gly
        435                 440                 445 atc cat tgg tat gcc aat gcg ctc tac aag gtc aag gac tac gtg ctg    1392
Ile His Trp Tyr Ala Asn Ala Leu Tyr Lys Val Lys Asp Tyr Val Leu
    450                 455                 460 ccg cag agc tgg cgc cac gat tga                                     1416
Pro Gln Ser Trp Arg His Asp
465                 470

<210> SEQ ID NO 20
<211> LENGTH: 471
<212> TYPE: PRT
<213> ORGANISM: Drosophila melanogaster

<400> SEQUENCE: 20

Met Asp Asn His Ser Ser Val Pro Trp Ala Ser Ala Ala Ser Val Thr
  1               5                  10                  15

Cys Leu Ser Leu Gly Cys Gln Met Pro Gln Phe Gln Phe Gln Phe Gln
             20                  25                  30

Leu Gln Ile Arg Ser Glu Leu His Leu Arg Lys Pro Ala Arg Arg Thr
         35                  40                  45

Gln Thr Met Arg His Ile Ala His Thr Gln Arg Cys Leu Ser Arg Leu
```

```
            50                  55                  60
Thr Ser Leu Val Ala Leu Leu Ile Val Leu Pro Met Val Phe Ser
 65                  70                  75                  80

Pro Ala His Ser Cys Gly Pro Gly Arg Gly Leu Gly Arg His Arg Ala
                 85                  90                  95

Arg Asn Leu Tyr Pro Leu Val Leu Lys Gln Thr Ile Pro Asn Leu Ser
                100                 105                 110

Glu Tyr Thr Asn Ser Ala Ser Gly Pro Leu Glu Gly Val Ile Arg Arg
                115                 120                 125

Asp Ser Pro Lys Phe Lys Asp Leu Val Pro Asn Tyr Asn Arg Asp Ile
130                 135                 140

Leu Phe Arg Asp Glu Glu Gly Thr Gly Ala Asp Gly Leu Met Ser Lys
145                 150                 155                 160

Arg Cys Lys Glu Lys Leu Asn Val Leu Ala Tyr Ser Val Met Asn Glu
                165                 170                 175

Trp Pro Gly Ile Arg Leu Leu Val Thr Glu Ser Trp Asp Glu Asp Tyr
                180                 185                 190

His His Gly Gln Glu Ser Leu His Tyr Glu Gly Arg Ala Val Thr Ile
                195                 200                 205

Ala Thr Ser Asp Arg Asp Gln Ser Lys Tyr Gly Met Leu Ala Arg Leu
210                 215                 220

Ala Val Glu Ala Gly Phe Asp Trp Val Ser Tyr Val Ser Arg Arg His
225                 230                 235                 240

Ile Tyr Cys Ser Val Lys Ser Asp Ser Ser Ile Ser Ser His Val His
                245                 250                 255

Gly Cys Phe Thr Pro Glu Ser Thr Ala Leu Leu Glu Ser Gly Val Arg
                260                 265                 270

Lys Pro Leu Gly Glu Leu Ser Ile Gly Asp Arg Val Leu Ser Met Thr
                275                 280                 285

Ala Asn Gly Gln Ala Val Tyr Ser Glu Val Ile Leu Phe Met Asp Arg
290                 295                 300

Asn Leu Glu Gln Met Gln Asn Phe Val Gln Leu His Thr Asp Gly Gly
305                 310                 315                 320

Ala Val Leu Thr Val Thr Pro Ala His Leu Val Ser Val Trp Gln Pro
                325                 330                 335

Glu Ser Gln Lys Leu Thr Phe Val Phe Ala His Arg Ile Glu Glu Lys
                340                 345                 350

Asn Gln Val Leu Val Arg Asp Val Glu Thr Gly Glu Leu Arg Pro Gln
                355                 360                 365

Arg Val Val Lys Leu Gly Ser Val Arg Ser Lys Gly Val Val Ala Pro
370                 375                 380

Leu Thr Arg Glu Gly Thr Ile Val Val Asn Ser Val Ala Ala Ser Cys
385                 390                 395                 400

Tyr Ala Val Ile Asn Ser Gln Ser Leu Ala His Trp Gly Leu Ala Pro
                405                 410                 415

Met Arg Leu Leu Ser Thr Leu Glu Ala Trp Leu Pro Ala Lys Glu Gln
                420                 425                 430

Leu His Ser Ser Pro Lys Val Val Ser Ala Gln Gln Gln Asn Gly
                435                 440                 445

Ile His Trp Tyr Ala Asn Ala Leu Tyr Lys Val Lys Asp Tyr Val Leu
                450                 455                 460

Pro Gln Ser Trp Arg His Asp
465                 470
```

```
<210> SEQ ID NO 21
<211> LENGTH: 221
<212> TYPE: PRT
<213> ORGANISM: Artificial Sequence
<220> FEATURE:
<223> OTHER INFORMATION: Description of Artificial Sequence: Degenerate
      Shh polypeptide general formula
<220> FEATURE:
<221> NAME/KEY: SITE
<222> LOCATION: (7)
<223> OTHER INFORMATION: Xaa=Gly, Ala, Val, Leu, Ile, Phe, Tyr, or Trp
<220> FEATURE:
<221> NAME/KEY: SITE
<222> LOCATION: (9)
<223> OTHER INFORMATION: Xaa=Arg, His or Lys
<220> FEATURE:
<221> NAME/KEY: SITE
<222> LOCATION: (44)
<223> OTHER INFORMATION: Xaa=Gly, Ala, Val, Leu, Ile, Ser. or Thr
<220> FEATURE:
<221> NAME/KEY: SITE
<222> LOCATION: (85)
<223> OTHER INFORMATION: Xaa=Gly, Ala, Val, Leu, Ile, Ser, or Thr
<220> FEATURE:
<221> NAME/KEY: SITE
<222> LOCATION: (93)
<223> OTHER INFORMATION: Xaa=Lys, Arg, His, Asn, or Gln
<220> FEATURE:
<221> NAME/KEY: SITE
<222> LOCATION: (98)
<223> OTHER INFORMATION: Xaa=Lys, Arg or His
<220> FEATURE:
<221> NAME/KEY: SITE
<222> LOCATION: (112)
<223> OTHER INFORMATION: Xaa=Ser, Thr, Tyr, Trp, or Phe
<220> FEATURE:
<221> NAME/KEY: SITE
<222> LOCATION: (132)
<223> OTHER INFORMATION: Xaa=Lys, Arg or His
<220> FEATURE:
<221> NAME/KEY: SITE
<222> LOCATION: (137)
<223> OTHER INFORMATION: Xaa=Met, Cys, Ser, or Thr
<220> FEATURE:
<221> NAME/KEY: SITE
<222> LOCATION: (139)
<223> OTHER INFORMATION: Xaa=Gly, Ala, Val, Leu, Ile, Ser, or Thr
<220> FEATURE:
<221> NAME/KEY: SITE
<222> LOCATION: (181)
<223> OTHER INFORMATION: Xaa=Leu, Val, Met, Thr, or Ser
<220> FEATURE:
<221> NAME/KEY: SITE
<222> LOCATION: (183)
<223> OTHER INFORMATION: Xaa=His, Phe, Tyr, Ser, Thr, Met, or Cys
<220> FEATURE:
<221> NAME/KEY: SITE
<222> LOCATION: (185)
<223> OTHER INFORMATION: Xaa=Gln, Asn, Glu, or Asp
<220> FEATURE:
<221> NAME/KEY: SITE
<222> LOCATION: (186)
<223> OTHER INFORMATION: Xaa=His, Phe, Tyr, Thr, Gln, Asn, Glu, or Asp
<220> FEATURE:
<221> NAME/KEY: SITE
<222> LOCATION: (189)
<223> OTHER INFORMATION: Xaa=Gln, Asn, Glu, Asp, Thr, Ser, Met, or Cys
<220> FEATURE:
<221> NAME/KEY: SITE
<222> LOCATION: (191)
<223> OTHER INFORMATION: Xaa=Ala, Gly, Cys, Leu, Val, or Met
<220> FEATURE:
<221> NAME/KEY: SITE
<222> LOCATION: (196)
<223> OTHER INFORMATION: Xaa=Arg, Lys, Met, Ile, Asn, Asp, Glu, Gln,
      Ser, Thr, or Cys
<220> FEATURE:
```

```
<221> NAME/KEY: SITE
<222> LOCATION: (200)
<223> OTHER INFORMATION: Xaa=Arg, Lys, Met, or Ile
<220> FEATURE:
<221> NAME/KEY: SITE
<222> LOCATION: (206)
<223> OTHER INFORMATION: Xaa=Ala, Gly, Cys, Asp, Glu, Gln, Asn, Ser,
      Thr, or Met
<220> FEATURE:
<221> NAME/KEY: SITE
<222> LOCATION: (207)
<223> OTHER INFORMATION: Xaa=Ala, Gly, Cys, Asp, Asn, Glu, or Gln
<220> FEATURE:
<221> NAME/KEY: SITE
<222> LOCATION: (209)
<223> OTHER INFORMATION: Xaa=Arg, Lys, Met, Ile, Asn, Asp, or Glu
<220> FEATURE:
<221> NAME/KEY: SITE
<222> LOCATION: (211)
<223> OTHER INFORMATION: Xaa=Leu, Val, Met, or Ile
<220> FEATURE:
<221> NAME/KEY: SITE
<222> LOCATION: (212)
<223> OTHER INFORMATION: Xaa=Phe, Tyr, Thr, His, or Trp
<220> FEATURE:
<221> NAME/KEY: SITE
<222> LOCATION: (216)
<223> OTHER INFORMATION: Xaa=Ile, Val, Leu, or Met
<220> FEATURE:
<221> NAME/KEY: SITE
<222> LOCATION: (217)
<223> OTHER INFORMATION: Xaa=Met, Cys, Ile, Leu, Val, Thr, or Ser
<220> FEATURE:
<221> NAME/KEY: SITE
<222> LOCATION: (219)
<223> OTHER INFORMATION: Xaa=Leu, Val, Met, Thr, or Ser

<400> SEQUENCE: 21

Cys Gly Pro Gly Arg Gly Xaa Gly Xaa Arg Arg His Pro Lys Lys Leu
  1               5                  10                  15

Thr Pro Leu Ala Tyr Lys Gln Phe Ile Pro Asn Val Ala Glu Lys Thr
                 20                  25                  30

Leu Gly Ala Ser Gly Arg Tyr Glu Gly Lys Ile Xaa Arg Asn Ser Glu
             35                  40                  45

Arg Phe Lys Glu Leu Thr Pro Asn Tyr Asn Pro Asp Ile Ile Phe Lys
 50                  55                  60

Asp Glu Asn Thr Gly Ala Asp Arg Leu Met Thr Gln Arg Cys Lys
 65                  70                  75                  80

Asp Lys Leu Asn Xaa Leu Ala Ile Ser Val Met Asn Xaa Trp Pro Gly
                 85                  90                  95

Val Xaa Leu Arg Val Thr Glu Gly Trp Asp Glu Asp Gly His His Xaa
            100                 105                 110

Glu Glu Ser Leu His Tyr Glu Gly Arg Ala Val Asp Ile Thr Thr Ser
            115                 120                 125

Asp Arg Asp Xaa Ser Lys Tyr Gly Xaa Leu Xaa Arg Leu Ala Val Glu
130                 135                 140

Ala Gly Phe Asp Trp Val Tyr Tyr Glu Ser Lys Ala His Ile His Cys
145                 150                 155                 160

Ser Val Lys Ala Glu Asn Ser Val Ala Lys Ser Gly Gly Cys Phe
                165                 170                 175

Pro Gly Ser Ala Xaa Val Xaa Leu Xaa Xaa Gly Gly Xaa Lys Xaa Val
            180                 185                 190

Lys Asp Leu Xaa Pro Gly Asp Xaa Val Leu Ala Ala Asp Xaa Xaa Gly
            195                 200                 205

Xaa Leu Xaa Xaa Ser Asp Phe Xaa Xaa Phe Xaa Asp Arg
```

```
                 210                 215                 220
```

<210> SEQ ID NO 22
<211> LENGTH: 167
<212> TYPE: PRT
<213> ORGANISM: Artificial Sequence
<220> FEATURE:
<223> OTHER INFORMATION: Description of Artificial Sequence: Degenerate
      hedgehog polypeptide general formula
<220> FEATURE:
<221> NAME/KEY: SITE
<222> LOCATION: (7)
<223> OTHER INFORMATION: Xaa=Gly, Ala, Val, Leu, Ile, Pro, Phe, or Tyr
<220> FEATURE:
<221> NAME/KEY: SITE
<222> LOCATION: (8)
<223> OTHER INFORMATION: Xaa=Gly, Ala, Val, Leu, or Ile
<220> FEATURE:
<221> NAME/KEY: SITE
<222> LOCATION: (9)
<223> OTHER INFORMATION: Xaa=Gly, Ala, Val, Leu, Ile, Lys, His, or Arg
<220> FEATURE:
<221> NAME/KEY: SITE
<222> LOCATION: (12)
<223> OTHER INFORMATION: Xaa=Lys, Arg or His
<220> FEATURE:
<221> NAME/KEY: SITE
<222> LOCATION: (13)
<223> OTHER INFORMATION: Xaa=Phe, Trp or Tyr or an amino acid gap
<220> FEATURE:
<221> NAME/KEY: SITE
<222> LOCATION: (14)
<223> OTHER INFORMATION: Xaa=Gly, Ala, Val, Leu, or Ile or an amino acid
      gap
<220> FEATURE:
<221> NAME/KEY: SITE
<222> LOCATION: (17)
<223> OTHER INFORMATION: Xaa=Asn, Gln, His, Arg, or Lys
<220> FEATURE:
<221> NAME/KEY: SITE
<222> LOCATION: (19)
<223> OTHER INFORMATION: Xaa=Gly, Ala, Val, Leu, Ile, Ser, or Thr
<220> FEATURE:
<221> NAME/KEY: SITE
<222> LOCATION: (22)
<223> OTHER INFORMATION: Xaa=Gly, Ala, Val, Leu, Ile, Ser, or Thr
<220> FEATURE:
<221> NAME/KEY: SITE
<222> LOCATION: (27)
<223> OTHER INFORMATION: Xaa=Gly, Ala, Val, Leu, Ile, Ser, or Thr
<220> FEATURE:
<221> NAME/KEY: SITE
<222> LOCATION: (29)
<223> OTHER INFORMATION: Xaa=Ser, Thr, Gln, or Asn
<220> FEATURE:
<221> NAME/KEY: SITE
<222> LOCATION: (30)
<223> OTHER INFORMATION: Xaa=Met, Cys, Gly, Ala, Val, Leu, Ile, Ser, or
      Thr
<220> FEATURE:
<221> NAME/KEY: SITE
<222> LOCATION: (31)
<223> OTHER INFORMATION: Xaa=Gly, Alka, Val, Leu, Ile, or Pro
<220> FEATURE:
<221> NAME/KEY: SITE
<222> LOCATION: (33)
<223> OTHER INFORMATION: Xaa=Arg, His or Lys
<220> FEATURE:
<221> NAME/KEY: SITE
<222> LOCATION: (40)
<223> OTHER INFORMATION: Xaa=Gly, Ala, Val, Leu, Ile, Pro Arg, His, or
      Lys
<220> FEATURE:
<221> NAME/KEY: SITE
<222> LOCATION: (41)
<223> OTHER INFORMATION: Xaa=Gly, Ala, Val, Leu, Ile, Phe, or Tyr
<220> FEATURE:
<221> NAME/KEY: SITE

```
<222> LOCATION: (44)
<223> OTHER INFORMATION: Xaa=Arg, His or Lys
<220> FEATURE:
<221> NAME/KEY: SITE
<222> LOCATION: (45)
<223> OTHER INFORMATION: Xaa=Gly, Ala, Val, Leu, Ile, Ser, or Thr
<220> FEATURE:
<221> NAME/KEY: SITE
<222> LOCATION: (46)
<223> OTHER INFORMATION: Xaa=Thr or Ser
<220> FEATURE:
<221> NAME/KEY: SITE
<222> LOCATION: (48)
<223> OTHER INFORMATION: Xaa=Gly, Ala, Val, Leu, Ile, Asn, or Gln
<220> FEATURE:
<221> NAME/KEY: SITE
<222> LOCATION: (53)
<223> OTHER INFORMATION: Xaa=Arg, His or Lys
<220> FEATURE:
<221> NAME/KEY: SITE
<222> LOCATION: (54)
<223> OTHER INFORMATION: Xaa=Asp or Glu
<220> FEATURE:
<221> NAME/KEY: SITE
<222> LOCATION: (71)
<223> OTHER INFORMATION: Xaa=Ser or Thr
<220> FEATURE:
<221> NAME/KEY: SITE
<222> LOCATION: (79)
<223> OTHER INFORMATION: Xaa=Glu, Asp, Gln, or Asn
<220> FEATURE:
<221> NAME/KEY: SITE
<222> LOCATION: (83)
<223> OTHER INFORMATION: Xaa=Glu or Asp
<220> FEATURE:
<221> NAME/KEY: SITE
<222> LOCATION: (84)
<223> OTHER INFORMATION: Xaa=Arg, His or Lys
<220> FEATURE:
<221> NAME/KEY: SITE
<222> LOCATION: (85)
<223> OTHER INFORMATION: Xaa=Gly, Ala, Val, Leu, or Ile
<220> FEATURE:
<221> NAME/KEY: SITE
<222> LOCATION: (87)
<223> OTHER INFORMATION: Xaa=Gly, Ala, Val, Leu, Ile, Thr, or Ser
<220> FEATURE:
<221> NAME/KEY: SITE
<222> LOCATION: (95)
<223> OTHER INFORMATION: Xaa=Met, Cys, Gln, Asn, Arg, Lys, or His
<220> FEATURE:
<221> NAME/KEY: SITE
<222> LOCATION: (100)
<223> OTHER INFORMATION: Xaa=Arg, His or Lys
<220> FEATURE:
<221> NAME/KEY: SITE
<222> LOCATION: (107)
<223> OTHER INFORMATION: Xaa=Trp, Phe, Tyr, Arg, His, or Lys
<220> FEATURE:
<221> NAME/KEY: SITE
<222> LOCATION: (114)
<223> OTHER INFORMATION: Xaa=Gly, Ala, Val, Leu, Ile, Ser, Thr, Tyr, or
      Phe
<220> FEATURE:
<221> NAME/KEY: SITE
<222> LOCATION: (115)
<223> OTHER INFORMATION: Xaa=Gln, Asn, Asp, or Glu
<220> FEATURE:
<221> NAME/KEY: SITE
<222> LOCATION: (116)
<223> OTHER INFORMATION: Xaa=Asp or Glu
<220> FEATURE:
<221> NAME/KEY: SITE
<222> LOCATION: (125)
<223> OTHER INFORMATION: Xaa=Gly, Ala, Val, Leu, or Ile
<220> FEATURE:
<221> NAME/KEY: SITE
<222> LOCATION: (134)
<223> OTHER INFORMATION: Xaa=Arg, His or Lys
```

```
<220> FEATURE:
<221> NAME/KEY: SITE
<222> LOCATION: (135)
<223> OTHER INFORMATION: Xaa=Asn, Gln, Thr, or Ser
<220> FEATURE:
<221> NAME/KEY: SITE
<222> LOCATION: (139)
<223> OTHER INFORMATION: Xaa=Gly, Ala, Val, Leu, Ile, Ser, Thr, Met, or
      Cys
<220> FEATURE:
<221> NAME/KEY: SITE
<222> LOCATION: (141)
<223> OTHER INFORMATION: Xaa=Gly, Ala, Val, Leu, Ile, Thr, or Ser
<220> FEATURE:
<221> NAME/KEY: SITE
<222> LOCATION: (157)
<223> OTHER INFORMATION: Xaa=Arg, His or Lys
<220> FEATURE:
<221> NAME/KEY: SITE
<222> LOCATION: (158)
<223> OTHER INFORMATION: Xaa=Asn, Gln, Gly, Ala, Val, Leu, or Ile
<220> FEATURE:
<221> NAME/KEY: SITE
<222> LOCATION: (160)
<223> OTHER INFORMATION: Xaa=Gly, Ala, Val, Leu, or Ile
<220> FEATURE:
<221> NAME/KEY: SITE
<222> LOCATION: (162)..(162)
<223> OTHER INFORMATION: Xaa=Gly, Ala, Val, Leu, Ile, Ser, Thr, or Cys
<220> FEATURE:
<221> NAME/KEY: SITE
<222> LOCATION: (166)
<223> OTHER INFORMATION: Xaa=Gly, Ala, Val, Leu, Ile, Thr, or Ser
<220> FEATURE:
<221> NAME/KEY: SITE
<222> LOCATION: (167)
<223> OTHER INFORMATION: Xaa=Asp or Glu

<400> SEQUENCE: 22

Cys Gly Pro Gly Arg Gly Xaa Xaa Xaa Arg Xaa Xaa Xaa Pro Lys
  1               5                  10                  15

Xaa Leu Xaa Pro Leu Xaa Tyr Lys Gln Phe Xaa Pro Xaa Xaa Xaa Glu
             20                  25                  30

Xaa Thr Leu Gly Ala Ser Gly Xaa Xaa Glu Gly Xaa Xaa Xaa Arg Xaa
         35                  40                  45

Ser Glu Arg Phe Xaa Xaa Leu Thr Pro Asn Tyr Asn Pro Asp Ile Ile
     50                  55                  60

Phe Lys Asp Glu Glu Asn Xaa Gly Ala Asp Arg Leu Met Thr Xaa Arg
 65                  70                  75                  80

Cys Lys Xaa Xaa Xaa Asn Xaa Leu Ala Ile Ser Val Met Asn Xaa Trp
             85                  90                  95

Pro Gly Val Xaa Leu Arg Val Thr Glu Gly Xaa Asp Glu Asp Gly His
            100                 105                 110

His Xaa Xaa Xaa Ser Leu His Tyr Glu Gly Arg Ala Xaa Asp Ile Thr
        115                 120                 125

Thr Ser Asp Arg Asp Xaa Xaa Lys Tyr Gly Xaa Leu Xaa Arg Leu Ala
    130                 135                 140

Val Glu Ala Gly Phe Asp Trp Val Tyr Tyr Glu Ser Xaa Xaa His Xaa
145                 150                 155                 160

His Xaa Ser Val Lys Xaa Xaa
            165

<210> SEQ ID NO 23
<211> LENGTH: 74
<212> TYPE: DNA
<213> ORGANISM: Artificial Sequence
<220> FEATURE:
```

<223> OTHER INFORMATION: primer

<400> SEQUENCE: 23

| gcgcgcttcg aagcgaggca gccagcgagg gagagagcga gcgggcgagc cggagcgagg | 60 |
| aaatcgatgc gcgc | 74 |

<210> SEQ ID NO 24
<211> LENGTH: 74
<212> TYPE: DNA
<213> ORGANISM: Artificial Sequence
<220> FEATURE:
<223> OTHER INFORMATION: primer

<400> SEQUENCE: 24

| gcgcgcagat ctgggaaagc gcaagagaga gcgcacacgc acacacccgc cgcgcgcact | 60 |
| cgggatccgc gcgc | 74 |

<210> SEQ ID NO 25
<211> LENGTH: 996
<212> TYPE: DNA
<213> ORGANISM: Artificial Sequence
<220> FEATURE:
<223> OTHER INFORMATION: gene activation construct

<400> SEQUENCE: 25

| cgaagcgagg cagccagcga gggagagagc gagcgggcga gccggagcga ggaaatcgaa | 60 |
| ggttcgaatc cttcccccac caccatcact ttcaaaagtc cgaaagaatc tgctccctgc | 120 |
| ttgtgtgttg gaggtcgctg agtagtgcgc gagtaaaatt taagctacaa caaggcaagg | 180 |
| cttgaccgac aattgcatga agaatctgct tagggttagg cgttttgcgc tgcttcgcga | 240 |
| tgtacgggcc agatatacgc gttgacattg attattgact agttattaat agtaatcaat | 300 |
| tacgggtca ttagttcata gcccatatat ggagttccgc gttacataac ttacggtaaa | 360 |
| tggcccgcct ggctgaccgc ccaacgaccc ccgcccattg acgtcaataa tgacgtatgt | 420 |
| tcccatagta acgccaatag ggactttcca ttgacgtcaa tgggtggact atttacggta | 480 |
| aactgcccac ttggcagtac atcaagtgta tcatatgcca agtacgcccc ctattgacgt | 540 |
| caatgacggt aaatggcccg cctggcatta tgcccagtac atgaccttat gggactttcc | 600 |
| tacttggcag tacatctacg tattagtcat cgctattacc atggtgatgc ggttttggca | 660 |
| gtacatcaat gggcgtggat agcggtttga ctcacgggga tttccaagtc tccaccccat | 720 |
| tgacgtcaat gggagtttgt tttggcacca aaatcaacgg gactttccaa aatgtcgtaa | 780 |
| caactccgcc ccattgacgc aaatgggcgg taggcgtgta cggtgggagg tctatataag | 840 |
| cagagctctc tggctaacta gagaacccac tgcttactgg cttatcgaaa ttaatacgac | 900 |
| tcactatagg gagacccaag cttggtaccg agctcggatc gatctgggaa agcgcaagag | 960 |
| agagcgcaca cgcacacacc cgccgcgcgc actcgg | 996 |

<210> SEQ ID NO 26
<211> LENGTH: 26
<212> TYPE: DNA
<213> ORGANISM: Artificial Sequence
<220> FEATURE:
<223> OTHER INFORMATION: primer

<400> SEQUENCE: 26

| gtcctggcgc cgccgccgcc gtcgcc | 26 |

-continued

```
<210> SEQ ID NO 27
<211> LENGTH: 26
<212> TYPE: DNA
<213> ORGANISM: Artificial Sequence
<220> FEATURE:
<223> OTHER INFORMATION: primer

<400> SEQUENCE: 27
ttccgatgac cggcctttcg cggtga                                      26

<210> SEQ ID NO 28
<211> LENGTH: 26
<212> TYPE: DNA
<213> ORGANISM: Artificial Sequence
<220> FEATURE:
<223> OTHER INFORMATION: primer

<400> SEQUENCE: 28
gtgcacggaa aggtgcaggc cacact                                      26
```